United States Patent
Hochradl et al.

(10) Patent No.: US 11,926,651 B2
(45) Date of Patent: Mar. 12, 2024

(54) POLYPEPTIDE CONSTRUCT COMPRISING FRAGMENTS OF ALLERGENS

(71) Applicant: WORG PHARMACEUTICALS (ZHEJIANG) CO., LTD., Huzhou (CN)

(72) Inventors: Monika Hochradl, Vienna (AT); Frank Stolz, Vienna (AT); Angela Neubauer, Vienna (AT); Rainer Henning, Vienna (AT); Elijahu Babaev, Vienna (AT)

(73) Assignee: WORG PHARMACEUTICALS (ZHEJIANG) CO., LTD., Huzhou (CN)

( * ) Notice: Subject to any disclaimer, the term of this patent is extended or adjusted under 35 U.S.C. 154(b) by 678 days.

(21) Appl. No.: 16/335,022

(22) PCT Filed: Sep. 20, 2017

(86) PCT No.: PCT/EP2017/073808
§ 371 (c)(1),
(2) Date: Mar. 20, 2019

(87) PCT Pub. No.: WO2018/054993
PCT Pub. Date: Mar. 29, 2018

(65) Prior Publication Data
US 2019/0248844 A1 Aug. 15, 2019

(30) Foreign Application Priority Data
Sep. 20, 2016 (EP) ..................... 16189774

(51) Int. Cl.
| | |
|---|---|
| C07K 14/415 | (2006.01) |
| A61K 39/00 | (2006.01) |
| A61K 39/36 | (2006.01) |
| A61P 37/08 | (2006.01) |
| C07K 14/005 | (2006.01) |
| C12N 5/10 | (2006.01) |
| C12N 15/00 | (2006.01) |
| C12N 15/64 | (2006.01) |
| C12N 15/66 | (2006.01) |

(52) U.S. Cl.
CPC ............ *C07K 14/415* (2013.01); *A61K 39/36* (2013.01); *A61P 37/08* (2018.01); *C07K 14/005* (2013.01); *C12N 5/10* (2013.01); *C12N 15/00* (2013.01); *C12N 15/64* (2013.01); *C12N 15/66* (2013.01); *A61K 2039/575* (2013.01); *A61K 2039/6075* (2013.01); *C07K 2319/00* (2013.01); *C07K 2319/21* (2013.01); *C12N 2511/00* (2013.01); *C12N 2523/00* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS 5,057,540 A  10/1991  Kensil

FOREIGN PATENT DOCUMENTS

| WO | 88/09336 A1 | 12/1988 |
|---|---|---|
| WO | 93/00077 A1 | 1/1993 |
| WO | 96/11711 A1 | 4/1996 |
| WO | 96/013589 A1 | 5/1996 |
| WO | 96/33739 A1 | 10/1996 |
| WO | 01/035991 A2 | 5/2001 |
| WO | 2004/000351 A1 | 12/2003 |
| WO | 2006/096497 A2 | 9/2006 |
| WO | 2008/098749 A2 | 8/2008 |
| WO | 2010/018378 A2 | 2/2010 |
| WO | 2012/168487 A1 | 12/2012 |
| WO | 2013/001362 A2 | 1/2013 |

OTHER PUBLICATIONS

Griffith et al. 1991. Sequence polymorphism of Amb a I and Amb a II, the major allergens in *Ambrosia artemisiifolia* (short ragweed). Int. Arch. Allergy Appl. Immunol. 96:296-304.*
Kristiansen et al. 'Allergen immunotherapy for the prevention of allergy: A systematic review and meta-analysis.' Pediatr Allergy Immunol. Feb. 2017;28(1): 18-29. doi: 10.1111/pai.12661. Epub Dec. 12, 2016.*
Martignago et al. 'Preventive actions of allergen immunotherapy: the facts and the effects in search of evidence.' Clin Mol. Allergy 2017; 15: 13. Published online Jun. 15, 2017. doi: 10.1186/s12948-017-0070-7.*
Kuby Immunology, 4th Edition, Chapter 18, "Vaccines," pp. 449-465 (2001).*
Sailer et al. 'Molecular ensembles makle evolution unpredictable.' PNAS 114(45): 11938-11943, 2017.*
Björklund et al., Supervised identification of allergen-representative peptides for in silico detection of potentially allergenic proteins, Bioinformatics, 21:39-50 (2005).
Rafnar et al., Expression and Analysis of Recombinant Amb a V and Amb t V Allergens, The Journal of Biological Chemistry, 267:21119-21123 (1992).

(Continued)

*Primary Examiner* — Nora M Rooney
(74) *Attorney, Agent, or Firm* — Nevrivy Patent Law Group P.L.L.C.

(57) ABSTRACT

The present invention relates to a polypeptide construct comprising at least two fragments of an allergen from the Amb a 1 family of allergens from *Ambrosia atermisiifolia* or variants of said at least two fragments, wherein each of the at least two fragments consist of 20 to 50 amino acid residues and wherein at least one fragment is derived from amino acid residues 1 to 50 of the mature allergen and at least one fragment is derived from amino acid residues 240 and ending at the C-terminal end of the mature allergen.

23 Claims, 13 Drawing Sheets

Specification includes a Sequence Listing.

(56) References Cited

OTHER PUBLICATIONS

Altschul et al., Basic Local Alignment Search Tool, J. Mol. Biol., 215:403-410 (1990).
Bendtsen et al., Improved Prediction of Signal Peptides: SignalP 3.0, J. Mol, Biol., 340: 783-795 (2004).
International Search Report from Appl. No. PCT/EP2017/073808, dated Feb. 5, 2018.
Rafnar et al., Cloning of Amb a I (Antigen E), the Major Allergen Family of Short Ragweed Pollen, J. Biol. Chem., 266:1229-1236 (1991).
Jahn-Schmid et al., The T-cell response to Amb a 1 is characterized by 3 dominant epitopes and multiple MHC restriction elements, Journal of Allergy and Clinical Immunology, 126:1068-1071 (2010).
Wolf et al., Amb a 1 isoforms show distinct IgE-binding properties, Allergy, 71:458-459 (2016).
Wolf et al., Amb a 1 isoforms: Unequal siblings with distinct immunological features, Allergy, 72:1874-1882 (2017).
Wopfner et al., The alpha and beta subchain of Amb a 1, the major ragweed-pollen allergen show divergent reactivity at the IgE and T-cell level, Molecular Immunology, 46:2090-2097 (2009).

\* cited by examiner

FIG. 1

AEGVGEILPSVNETRSLQACEAVNIIDKCWRGKADWENNRQALADCAQGFAKGTYGGKW
AEGVGEILPSVNETRSLQACEAVNIIDK
Peptid 1 (1-27)

WRGKADWENNRQALADCAQGFAKGTYGGKW
Peptid 2 (29-59)

GDVYTVFSNLDDDVANPKEGTLRFAAAQNRPLWIIFKNDMVINLNQELVVNSDKTIDGRGVKVEINGGLTLMNVKNIIHNINIHDV
GDVYTVFSNLDDDVANPKEGTLRFAAAQNRC
Peptid 3 (60-89)

PLWIIFKNDMVINLNQELVVNSDKTIDGRGC
Peptid 4 (90-119)

VKVEINGGLTLMNVKNIIHNINIHDV
Peptid 5 (120-132)

KVLPGGMIKSNDGPPILRQASDGDTINVAGSSQIWIDHCSLSKSFDGLVDVTLGSTHVTISNCKFTQQSKAILLG
KVLPGC
CMIKSNDGPPILRQASDGDTINVAGSSQIWIDHC
Peptid 6 (153-186)

CDGLVDVTLGSTHVTISNCKFTQQSKAILLG
Peptid 7 (197-227)

ADDTHVQDKGMLATVAFNMFTDNVDQRMPRCRFGFFQVVNNNYDRWGTYAIGGSSAPTILCQGNRFLAPDDQIKKNVLA
CADDTHVQDKGMLATVAFNMFTDNVDQRMPR
Peptid 8 (229-252)

CRFGFFQVVNNNYDRWGTYAIGGSSAPTIL
Peptid 9 (253-282)

CQGNRFLAPDDQIKKNVLA
Peptid 10 (283-297)

RTGTGAAESMAWNWRSDKDLLENGAIFVTSGSDPVLTPVQSAGMIPAEPGEAAI KLTSSAGVLSCRPGAPC
RTGTGAAESMAWNWRS
SDPVLTPVQSAGMIPAEPGEAAIKLTSSAGVLSC
Peptid 11 (333-366)

IgE reactivity of peptides

Fig. 2

IgE reactivity of Amb a 1 fusion proteins

Fig. 8

Levels of Amb a 1-specific IgG after immunization with Amb a 1 derived peptides or wild-type Amb a 1

Fig. 3A

Levels of Amb a 1-specific IgG after immunization with Amb a 1 derived peptides or wild-type Amb a 1

Amb a 1 K1 (9/9/9/9/preS/11/11/11/11)

N- | Amb a 1 P9 | Amb a 1 P9 | Amb a 1 P9 | Amb a 1 P9 | Pre S | Amb a 1 P11 | Amb a 1 P11 | Amb a 1 P11 | Amb a 1 P11 | -C

Amb a 1 K2 (9/9/9/9/preS/11/11/11/11)

N- | Amb a 1 P9 | Amb a 1 P9 | Pre S | Amb a 1 P11 | Amb a 1 P11 | -C

Amb a 1 K3 (11/11/11/11/preS/9/9/9/9)

N- | Amb a 1 P11 | Amb a 1 P11 | Pre S | Amb a 1 P9 | Amb a 1

FIG. 4B

Amb a 1 K4 (9/9/1/1/11/11/preS/11/1/1/9/9)

N-

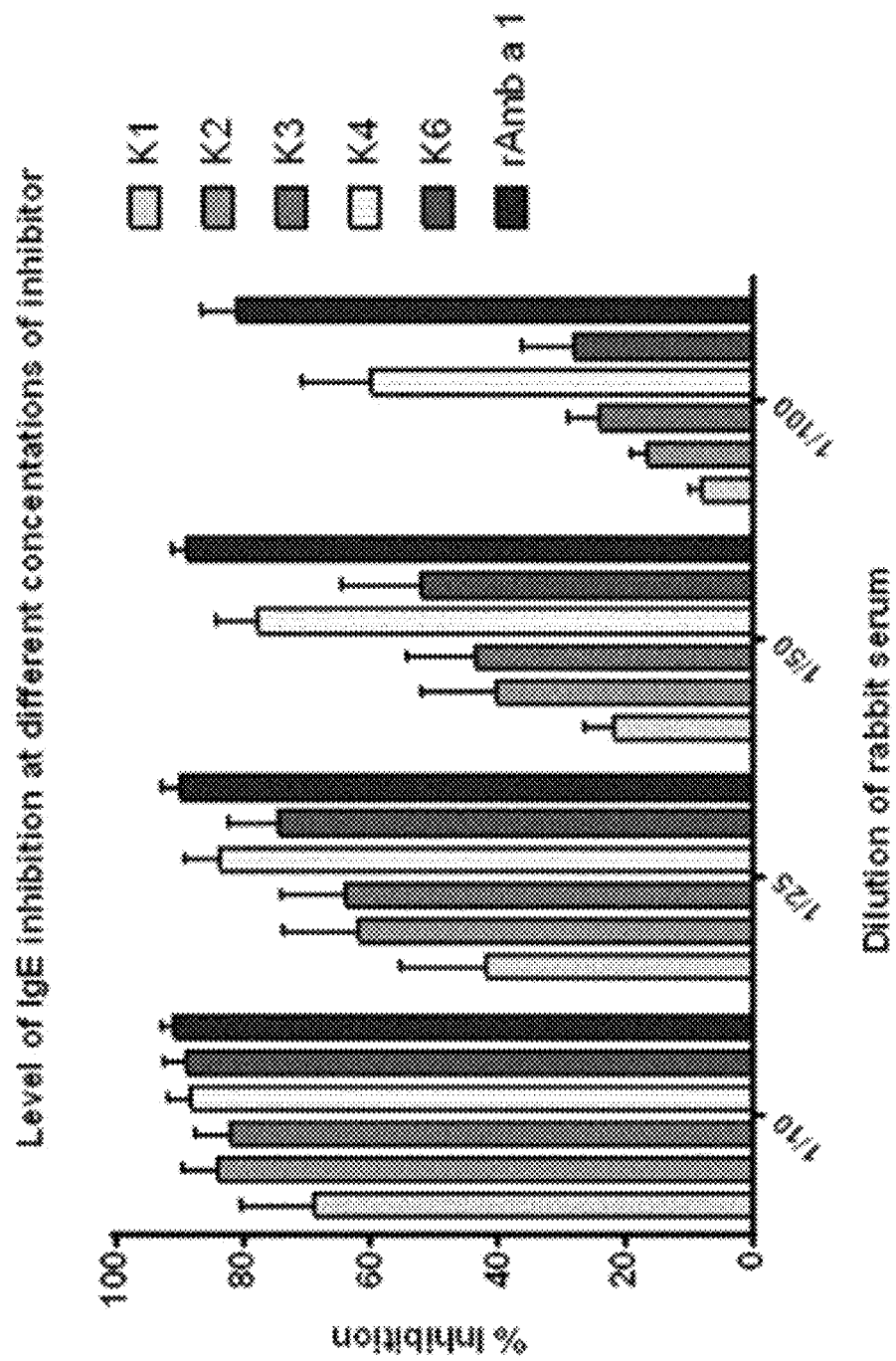

Basophil Activation Assay
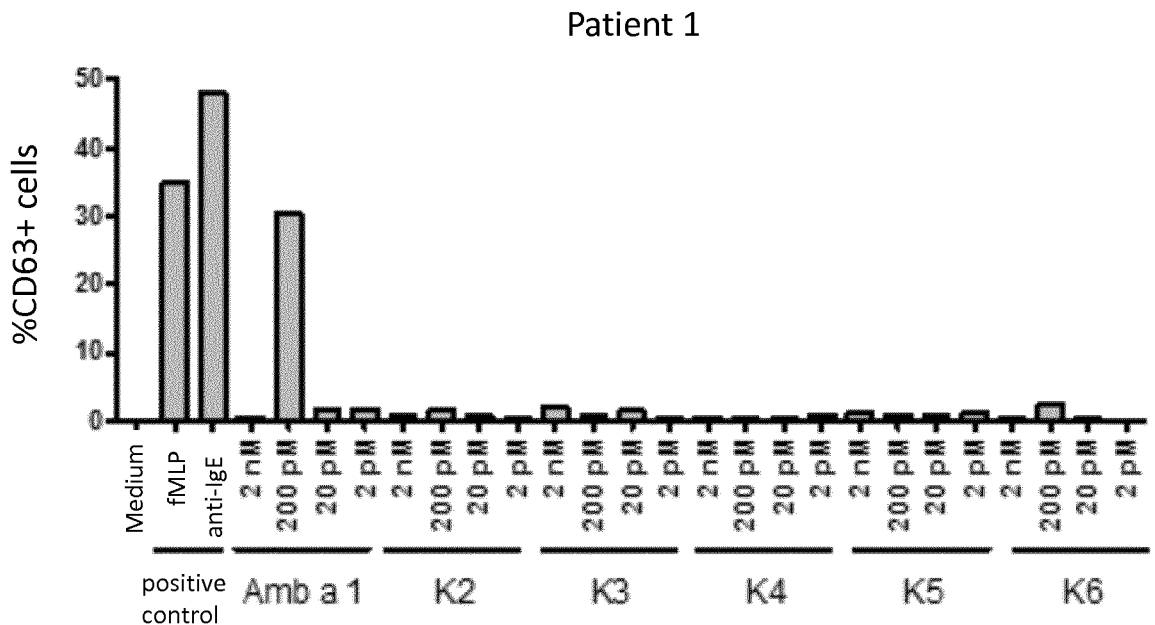
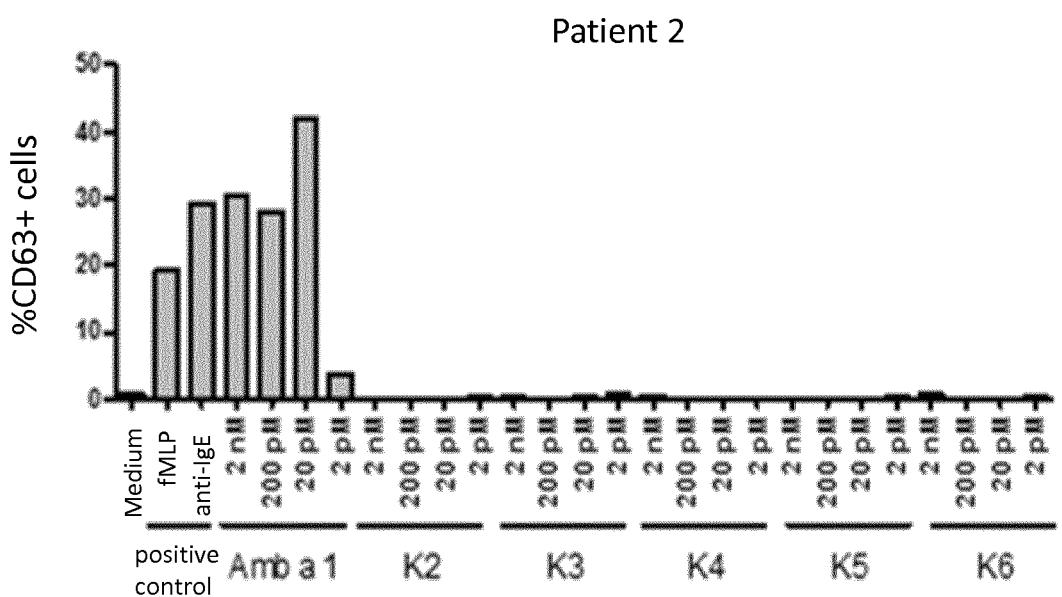
Fig. 10

FIG. 11A

Inhibition of patients' IgE-binding to wildtype Amb a 1 by single Peptide-Anti sera

Fig. 11B

Inhibition of patients' IgE-binding to wildtype Amb a 1 by Mixes of Peptide-Antisera

Fig. 11C

SEQUENCE LISTING

<160> NUMBER OF SEQ ID NOS: 70

<210> SEQ ID NO 1
<211> LENGTH: 372
<212> TYPE: PRT
<213> ORGANISM: Ambrosia artemisiifolia

<400> SEQUENCE: 1

```
Ala Glu Gly Val Gly Glu Ile Leu Pro Ser Val Asn Glu Thr Arg Ser
1               5                   10                  15

Leu Gln Ala Cys Glu Ala Tyr Asn Ile Ile Asp Lys Cys Trp Arg Gly
            20                  25                  30

Lys Ala Asp Trp Glu Asn Asn Arg Gln Ala Leu Ala Asp Cys Ala Gln
        35                  40                  45

Gly Phe Ala Lys Gly Thr Tyr Gly Gly Lys Trp Gly Asp Val Tyr Thr
    50                  55                  60

Val Thr Ser Asn Leu Asp Asp Val Ala Asn Pro Lys Glu Gly Thr
65                  70                  75                  80

Leu Arg Phe Ala Ala Ala Gln Asn Arg Pro Leu Trp Ile Ile Phe Lys
                85                  90                  95

Asn Asp Met Val Ile Asn Leu Asn Gln Glu Leu Val Val Asn Ser Asp
            100                 105                 110

Lys Thr Ile Asp Gly Arg Gly Val Lys Val Glu Ile Ile Asn Gly Gly
        115                 120                 125

Leu Thr Leu Met Asn Val Lys Asn Ile Ile Ile His Asn Ile Asn Ile
    130                 135                 140

His Asp Val Lys Val Leu Pro Gly Gly Met Ile Lys Ser Asn Asp Gly
145                 150                 155                 160

Pro Pro Ile Leu Arg Gln Ala Ser Asp Gly Asp Thr Ile Asn Val Ala
                165                 170                 175

Gly Ser Ser Gln Ile Trp Ile Asp His Cys Ser Leu Ser Lys Ser Phe
            180                 185                 190

Asp Gly Leu Val Asp Val Thr Leu Gly Ser Thr His Val Thr Ile Ser
        195                 200                 205

Asn Cys Lys Phe Thr Gln Gln Ser Lys Ala Ile Leu Leu Gly Ala Asp
    210                 215                 220
```

```
Asp Thr His Val Gln Asp Lys Gly Met Leu Ala Thr Val Ala Phe Asn
225                 230                 235                 240

Met Phe Thr Asp Asn Val Asp Gln Arg Met Pro Arg Cys Arg Phe Gly
            245                 250                 255

Phe Phe Gln Val Val Asn Asn Asn Tyr Asp Arg Trp Gly Thr Tyr Ala
        260                 265                 270

Ile Gly Gly Ser Ser Ala Pro Thr Ile Leu Cys Gln Gly Asn Arg Phe
    275                 280                 285

Leu Ala Pro Asp Asp Gln Ile Lys Lys Asn Val Leu Ala Arg Thr Gly
290                 295                 300

Thr Gly Ala Ala Glu Ser Met Ala Trp Asn Trp Arg Ser Asp Lys Asp
305                 310                 315                 320

Leu Leu Glu Asn Gly Ala Ile Phe Val Thr Ser Gly Ser Asp Pro Val
            325                 330                 335

Leu Thr Pro Val Gln Ser Ala Gly Met Ile Pro Ala Glu Pro Gly Glu
        340                 345                 350

Ala Ala Ile Lys Leu Thr Ser Ser Ala Gly Val Leu Ser Cys Arg Pro
    355                 360                 365

Gly Ala Pro Cys
    370

<210> SEQ ID NO 2
<211> LENGTH: 28
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (28)..(28)
<223> OTHER INFORMATION: Xaa is cysteine, serine or no amino acid
      residue

<400> SEQUENCE: 2

Ala Glu Asp Leu Gln Glu Ile Leu Pro Val Asn Glu Thr Arg Arg Leu
1               5                   10                  15

Thr Thr Ser Gly Ala Tyr Asn Ile Ile Asp Gly Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (20)..(20)
<223> OTHER INFORMATION: Xaa is cysteine or serine
<220> FEATURE:
<221> NAME/KEY: MISC_FEATURE
<222> LOCATION: (29)..(29)
<223> OTHER INFORMATION: Xaa is cysteine, serine or no amino acid
      residue

<400> SEQUENCE: 3

Ala Glu Asp Leu Gln Gln Ile Leu Pro Ser Ala Asn Glu Thr Arg Ser
1               5                   10                  15

Leu Thr Thr Xaa Gly Thr Tyr Asn Ile Ile Asp Gly Xaa
            20                  25

<210> SEQ ID NO 4
```

```
<211> LENGTH: 29
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (20)..(20)
<223> OTHER INFORMATION: Xaa is cysteine or serine
<220> FEATURE:
<221> NAME/KEY: MISC_FEATURE
<222> LOCATION: (29)..(29)
<223> OTHER INFORMATION: Xaa is cysteine, serine or no amino acid
      residue

<400> SEQUENCE: 4

Ala Glu Gly Val Gly Glu Ile Leu Pro Ser Val Asn Glu Thr Arg Ser
1               5                   10                  15

Leu Gln Ala Xaa Glu Ala Tyr Asn Ile Ile Asp Lys Xaa
            20                  25

<210> SEQ ID NO 5
<211> LENGTH: 30
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (21)..(21)
<223> OTHER INFORMATION: Xaa is cysteine or serine
<220> FEATURE:
<221> NAME/KEY: MISC_FEATURE
<222> LOCATION: (30)..(30)
<223> OTHER INFORMATION: Xaa is cysteine, serine or no amino acid
      residue

<400> SEQUENCE: 5

Ala Glu Asp Val Glu Glu Phe Leu Pro Ser Ala Asn Glu Thr Arg Arg
1               5                   10                  15

Ser Leu Lys Ala Xaa Glu Ala His Asn Ile Ile Asp Lys Xaa
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (1)..(1)
<223> OTHER INFORMATION: Xaa is cysteine, serine, leucine or no amino
      acid residue
<220> FEATURE:
<221> NAME/KEY: MISC_FEATURE
<222> LOCATION: (3)..(3)
<223> OTHER INFORMATION: Xaa is histidine or phenylalanine
<220> FEATURE:
<221> NAME/KEY: MISC_FEATURE
<222> LOCATION: (6)..(6)
<223> OTHER INFORMATION: Xaa is phenylalanine or valine
<220> FEATURE:
<221> NAME/KEY: MISC_FEATURE
<222> LOCATION: (14)..(14)
<223> OTHER INFORMATION: Xaa is aspartic acid or glutamic acid
<220> FEATURE:
<221> NAME/KEY: MISC_FEATURE
<222> LOCATION: (15)..(15)
<223> OTHER INFORMATION: Xaa is arginine or lysine
<220> FEATURE:
<221> NAME/KEY: MISC_FEATURE
<222> LOCATION: (18)..(18)
```

```
<223> OTHER INFORMATION: Xaa is threonine or serine
<220> FEATURE:
<221> NAME/KEY: MISC_FEATURE
<222> LOCATION: (21)..(21)
<223> OTHER INFORMATION: Xaa is isoleucine or leucine
<220> FEATURE:
<221> NAME/KEY: MISC_FEATURE
<222> LOCATION: (25)..(25)
<223> OTHER INFORMATION: Xaa is serine or alanine
<220> FEATURE:
<221> NAME/KEY: MISC_FEATURE
<222> LOCATION: (26)..(26)
<223> OTHER INFORMATION: Xaa is glycine, serine or alanine

<400> SEQUENCE: 6

Xaa Arg Xaa Gly Phe Xaa Gln Val Val Asn Asn Asn Tyr Xaa Xaa Trp
1               5                   10                  15

Gly Xaa Tyr Ala Xaa Gly Gly Ser Xaa Xaa Pro Thr Ile Leu
            20                  25                  30

<210> SEQ ID NO 7
<211> LENGTH: 34
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (1)..(1)
<223> OTHER INFORMATION: Xaa is serine or valine
<220> FEATURE:
<221> NAME/KEY: MISC_FEATURE
<222> LOCATION: (8)..(8)
<223> OTHER INFORMATION: Xaa is valine or glutamic acid
<220> FEATURE:
<221> NAME/KEY: MISC_FEATURE
<222> LOCATION: (10)..(10)
<223> OTHER INFORMATION: Xaa is serine, lysine or asparagine
<220> FEATURE:
<221> NAME/KEY: MISC_FEATURE
<222> LOCATION: (21)..(21)
<223> OTHER INFORMATION: Xaa is alanine or serine
<220> FEATURE:
<221> NAME/KEY: MISC_FEATURE
<222> LOCATION: (22)..(22)
<223> OTHER INFORMATION: Xaa is valine or alanine
<220> FEATURE:
<221> NAME/KEY: MISC_FEATURE
<222> LOCATION: (23)..(23)
<223> OTHER INFORMATION: Xaa is leucine or isoleucine
<220> FEATURE:
<221> NAME/KEY: MISC_FEATURE
<222> LOCATION: (24)..(24)
<223> OTHER INFORMATION: Xaa is serine, lysine or arginine
<220> FEATURE:
<221> NAME/KEY: MISC_FEATURE
<222> LOCATION: (34)..(34)
<223> OTHER INFORMATION: Xaa is cysteine, serine or no amino acid
      residue

<400> SEQUENCE: 7

Xaa Asp Pro Val Leu Thr Pro Xaa Gln Xaa Ala Gly Met Ile Pro Ala
1               5                   10                  15

Glu Pro Gly Glu Xaa Xaa Xaa Xaa Leu Thr Ser Ser Ala Gly Val Leu
            20                  25                  30

Ser Xaa

<210> SEQ ID NO 8
<211> LENGTH: 30
<212> TYPE: PRT
<213> ORGANISM: Artificial Sequence
<220> FEATURE:
```

<223> OTHER INFORMATION: Amb a 1 fragment
<220> FEATURE:
<221> NAME/KEY: MISC_FEATURE
<222> LOCATION: (1)..(1)
<223> OTHER INFORMATION: Xaa is cysteine, leucine, serine or no amino
      acid residue

<400> SEQUENCE: 8

Xaa Arg His Gly Phe Phe Gln Val Val Asn Asn Asn Tyr Asp Lys Trp
1               5                   10                  15

Gly Ser Tyr Ala Ile Gly Gly Ser Ala Ser Pro Thr Ile Leu
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (1)..(1)
<223> OTHER INFORMATION: Xaa is cysteine, leucine, serine or no amino
      acid residue

<400> SEQUENCE: 9

Xaa Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu
            20                  25                  30

<210> SEQ ID NO 10
<211> LENGTH: 34
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (34)..(34)
<223> OTHER INFORMATION: Xaa is cysteine, serine or no amino acid
      residue

<400> SEQUENCE: 10

Val Asp Pro Val Leu Thr Pro Glu Gln Ser Ala Gly Met Ile Pro Ala
1               5                   10                  15

Glu Pro Gly Glu Ser Ala Leu Ser Leu Thr Ser Ser Ala Gly Val Leu
            20                  25                  30

Ser Xaa

<210> SEQ ID NO 11
<211> LENGTH: 34
<212> TYPE: PRT
<213> ORGANISM: Artificial Sequence
<220> FEATURE:
<223> OTHER INFORMATION: Amb a 1 fragment
<220> FEATURE:
<221> NAME/KEY: MISC_FEATURE
<222> LOCATION: (34)..(34)
<223> OTHER INFORMATION: Xaa is cysteine, serine or no amino acid
      residue

<400> SEQUENCE: 11

Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Xaa

<210> SEQ ID NO 12
<211> LENGTH: 30
<212> TYPE: PRT
<213> ORGANISM: Artificial Sequence
<220> FEATURE:
<223> OTHER INFORMATION: Amb a 1

<400> SEQUENCE: 12

Pro Leu Trp Ile Ile Phe Glu Arg Asp Met Val Ile Arg Leu Asp Lys
1               5                   10                  15

Glu Met Val Val Asn Ser Asp Lys Thr Ile Asp Gly Arg Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 13

Pro Leu Trp Ile Ile Phe Ala Arg Asp Met Val Ile Arg Leu Asp Arg
1               5                   10                  15

Glu Leu Ala Ile Asn Asn Asp Lys Thr Ile Asp Gly Arg Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 14

Pro Leu Trp Ile Ile Phe Lys Asn Asp Met Val Ile Asn Leu Asn Gln
1               5                   10                  15

Glu Leu Val Val Asn Ser Asp Lys Thr Ile Asp Gly Arg Gly
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 15

Pro Leu Trp Ile Ile Phe Lys Arg Asn Met Val Ile His Leu Asn Gln
1               5                   10                  15

Glu Leu Val Val Asn Ser Asp Lys Thr Ile Asp Gly Arg Gly
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: Amb a 1 fragment

<400> SEQUENCE: 16

Ala Lys Val Glu Ile Ile Asn Ala Gly Phe Thr Leu Asn Gly Val Lys
1               5                   10                  15

```
Asn Val Ile Ile His Asn Ile Asn Met His Asp Val Lys Val Asn Pro
            20                  25                  30
Gly

<210> SEQ ID NO 17
<211> LENGTH: 33
<212> TYPE: PRT
<213> ORGANISM: Artificial Sequence
<220> FEATURE:
<223> OTHER INFORMATION: Amb a 1 fragment

<400> SEQUENCE: 17

Ala Lys Val Glu Ile Ile Asn Ala Gly Phe Ala Ile Tyr Asn Val Lys
1               5                   10                  15

Asn Ile Ile Ile His Asn Ile Ile Met His Asp Ile Val Val Asn Pro
            20                  25                  30
Gly

<210> SEQ ID NO 18
<211> LENGTH: 33
<212> TYPE: PRT
<213> ORGANISM: Artificial Sequence
<220> FEATURE:
<223> OTHER INFORMATION: Amb a 1 fragment

<400> SEQUENCE: 18

Val Lys Val Glu Ile Ile Asn Gly Gly Leu Thr Leu Met Asn Val Lys
1               5                   10                  15

Asn Ile Ile Ile His Asn Ile Asn Ile His Asp Val Lys Val Leu Pro
            20                  25                  30
Gly

<210> SEQ ID NO 19
<211> LENGTH: 33
<212> TYPE: PRT
<213> ORGANISM: Artificial Sequence
<220> FEATURE:
<223> OTHER INFORMATION: Amb a 1 fragment

<400> SEQUENCE: 19

Val Lys Val Asn Ile Val Asn Ala Gly Leu Thr Leu Met Asn Val Lys
1               5                   10                  15

Asn Ile Ile Ile His Asn Ile Asn Ile His Asp Ile Lys Val Cys Pro
            20                  25                  30
Gly

<210> SEQ ID NO 20
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 20

Ala Gly Asp Glu Asn Ile Glu Asp Arg Gly Met Leu Ala Thr Val Ala
1               5                   10                  15

Phe Asn Thr Phe Thr Asp Asn Val Asp Gln Arg Met Pro Arg
            20                  25                  30

<210> SEQ ID NO 21
<211> LENGTH: 26
```

```
<212> TYPE: PRT
<213> ORGANISM: Artificial Sequence
<220> FEATURE:
<223> OTHER INFORMATION: Amb a 1 fragment

<400> SEQUENCE: 21

Asp Phe Asp Glu Arg Gly Met Leu Cys Thr Val Ala Phe Asn Lys Phe
1               5                   10                  15

Thr Asp Asn Val Asp Gln Arg Met Pro Asn
            20                  25

<210> SEQ ID NO 22
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 22

Ala Asp Asp Thr His Val Gln Asp Lys Gly Met Leu Ala Thr Val Ala
1               5                   10                  15

Phe Asn Met Phe Thr Asp Asn Val Asp Gln Arg Met Pro Arg
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 23

Ala Asp Asp Thr His Tyr Gln Asp Lys Gly Met Leu Ala Thr Val Ala
1               5                   10                  15

Phe Asn Met Phe Thr Asp His Val Asp Gln Arg Met Pro Arg
            20                  25                  30

<210> SEQ ID NO 24
<211> LENGTH: 173
<212> TYPE: PRT
<213> ORGANISM: Hepatitis B virus

<400> SEQUENCE: 24

Gly Gly Trp Ser Ser Lys Pro Arg Lys Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Gly Ala Asn Ser Asn Asn Pro Asp Trp Asp Phe Asn Pro Ile Lys
        35                  40                  45

Asp His Trp Pro Ala Ala Asn Gln Val Gly Val Gly Ala Phe Gly Pro
    50                  55                  60

Gly Leu Thr Pro Pro His Gly Gly Ile Leu Gly Trp Ser Pro Gln Ala
65                  70                  75                  80

Gln Gly Ile Leu Thr Thr Val Ser Thr Ile Pro Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Ala Phe His Gln
        115                 120                 125

Ala Leu Gln Asp Pro Arg Val Arg Gly Leu Tyr Phe Pro Ala Gly Gly
    130                 135                 140
```

-continued

```
Ser Ser Ser Gly Thr Val Asn Pro Ala Pro Asn Ile Ala Ser His Ile
145                 150                 155                 160

Ser Ser Ile Ser Ala Arg Thr Gly Asp Pro Val Thr Asn
            165                 170

<210> SEQ ID NO 25
<211> LENGTH: 551
<212> TYPE: PRT
<213> ORGANISM: Artificial Sequence
<220> FEATURE:
<223> OTHER INFORMATION: K4His

<400> SEQUENCE: 25

Cys Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu Cys Arg
            20                  25                  30

Phe Gly Phe Phe Gln Val Val Asn Asn Asn Tyr Asp Arg Trp Gly Thr
        35                  40                  45

Tyr Ala Ile Gly Gly Ser Ser Ala Pro Thr Ile Leu Ala Glu Gly Val
    50                  55                  60

Gly Glu Ile Leu Pro Ser Val Asn Glu Thr Arg Ser Leu Gln Ala Cys
65                  70                  75                  80

Glu Ala Tyr Asn Ile Ile Asp Lys Cys Ala Glu Gly Val Gly Glu Ile
                85                  90                  95

Leu Pro Ser Val Asn Glu Thr Arg Ser Leu Gln Ala Cys Glu Ala Tyr
            100                 105                 110

Asn Ile Ile Asp Lys Cys Ser Asp Pro Val Leu Thr Pro Val Gln Ser
        115                 120                 125

Ala Gly Met Ile Pro Ala Glu Pro Gly Glu Ala Ala Ile Lys Leu Thr
    130                 135                 140

Ser Ser Ala Gly Val Leu Ser Cys Ser Asp Pro Val Leu Thr Pro Val
145                 150                 155                 160

Gln Ser Ala Gly Met Ile Pro Ala Glu Pro Gly Glu Ala Ala Ile Lys
                165                 170                 175

Leu Thr Ser Ser Ala Gly Val Leu Ser Cys Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
    210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Pro Ala Ser Thr Asn Arg Gln Ser Gly Arg
        275                 280                 285

Gln Pro Thr Pro Ile Ser Pro Pro Leu Arg Asp Ser His Pro Gln Ala
    290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335
```

Asn Pro Ala Pro Asn Ile Ala Ser His Ile Ser Ser Ile Ser Ala Arg
            340                 345                 350

Thr Gly Asp Pro Val Thr Asn Ser Asp Pro Val Leu Thr Pro Val Gln
        355                 360                 365

Ser Ala Gly Met Ile Pro Ala Glu Pro Gly Glu Ala Ala Ile Lys Leu
    370                 375                 380

Thr Ser Ser Ala Gly Val Leu Ser Cys Ser Asp Pro Val Leu Thr Pro
385                 390                 395                 400

Val Gln Ser Ala Gly Met Ile Pro Ala Glu Pro Gly Glu Ala Ala Ile
                405                 410                 415

Lys Leu Thr Ser Ser Ala Gly Val Leu Ser Cys Ala Glu Gly Val Gly
            420                 425                 430

Glu Ile Leu Pro Ser Val Asn Glu Thr Arg Ser Leu Gln Ala Cys Glu
        435                 440                 445

Ala Tyr Asn Ile Ile Asp Lys Cys Ala Glu Gly Val Gly Glu Ile Leu
    450                 455                 460

Pro Ser Val Asn Glu Thr Arg Ser Leu Gln Ala Cys Glu Ala Tyr Asn
465                 470                 475                 480

Ile Ile Asp Lys Cys Cys Arg Phe Gly Phe Phe Gln Val Val Asn Asn
                485                 490                 495

Asn Tyr Asp Arg Trp Gly Thr Tyr Ala Ile Gly Gly Ser Ser Ala Pro
            500                 505                 510

Thr Ile Leu Cys Arg Phe Gly Phe Phe Gln Val Val Asn Asn Asn Tyr
        515                 520                 525

Asp Arg Trp Gly Thr Tyr Ala Ile Gly Gly Ser Ser Ala Pro Thr Ile
    530                 535                 540

Leu His His His His His His
545                 550

<210> SEQ ID NO 26
<211> LENGTH: 539
<212> TYPE: PRT
<213> ORGANISM: Artificial Sequence
<220> FEATURE:
<223> OTHER INFORMATION: K4AHis

<400> SEQUENCE: 26

Arg Phe Gly Phe Phe Gln Val Val Asn Asn Asn Tyr Asp Arg Trp Gly
1               5                   10                  15

Thr Tyr Ala Ile Gly Gly Ser Ser Ala Pro Thr Ile Leu Arg Phe Gly
            20                  25                  30

Phe Phe Gln Val Val Asn Asn Asn Tyr Asp Arg Trp Gly Thr Tyr Ala
        35                  40                  45

Ile Gly Gly Ser Ser Ala Pro Thr Ile Leu Ala Glu Gly Val Gly Glu
    50                  55                  60

Ile Leu Pro Ser Val Asn Glu Thr Arg Ser Leu Gln Ala Cys Glu Ala
65                  70                  75                  80

Tyr Asn Ile Ile Asp Lys Ala Glu Gly Val Gly Glu Ile Leu Pro Ser
                85                  90                  95

Val Asn Glu Thr Arg Ser Leu Gln Ala Cys Glu Ala Tyr Asn Ile Ile
            100                 105                 110

Asp Lys Ser Asp Pro Val Leu Thr Pro Val Gln Ser Ala Gly Met Ile
        115                 120                 125

Pro Ala Glu Pro Gly Glu Ala Ala Ile Lys Leu Thr Ser Ser Ala Gly
    130                 135                 140

```
Val Leu Ser Ser Asp Pro Val Leu Thr Pro Val Gln Ser Ala Gly Met
145                 150                 155                 160

Ile Pro Ala Glu Pro Gly Glu Ala Ala Ile Lys Leu Thr Ser Ser Ala
                165                 170                 175

Gly Val Leu Ser Gly Gly Trp Ser Ser Lys Pro Arg Lys Gly Met Gly
            180                 185                 190

Thr Asn Leu Ser Val Pro Asn Pro Leu Gly Phe Phe Pro Asp His Gln
            195                 200                 205

Leu Asp Pro Ala Phe Gly Ala Asn Ser Asn Asn Pro Asp Trp Asp Phe
210                 215                 220

Asn Pro Ile Lys Asp His Trp Pro Ala Ala Asn Gln Val Gly Val Gly
225                 230                 235                 240

Ala Phe Gly Pro Gly Leu Thr Pro Pro His Gly Gly Ile Leu Gly Trp
                245                 250                 255

Ser Pro Gln Ala Gln Gly Ile Leu Thr Thr Val Ser Thr Ile Pro Pro
            260                 265                 270

Pro Ala Ser Thr Asn Arg Gln Ser Gly Arg Gln Pro Thr Pro Ile Ser
            275                 280                 285

Pro Pro Leu Arg Asp Ser His Pro Gln Ala Met Gln Trp Asn Ser Thr
290                 295                 300

Ala Phe His Gln Ala Leu Gln Asp Pro Arg Val Arg Gly Leu Tyr Phe
305                 310                 315                 320

Pro Ala Gly Gly Ser Ser Gly Thr Val Asn Pro Ala Pro Asn Ile
                325                 330                 335

Ala Ser His Ile Ser Ser Ile Ser Ala Arg Thr Gly Asp Pro Val Thr
            340                 345                 350

Asn Ser Asp Pro Val Leu Thr Pro Val Gln Ser Ala Gly Met Ile Pro
            355                 360                 365

Ala Glu Pro Gly Glu Ala Ala Ile Lys Leu Thr Ser Ser Ala Gly Val
370                 375                 380

Leu Ser Ser Asp Pro Val Leu Thr Pro Val Gln Ser Ala Gly Met Ile
385                 390                 395                 400

Pro Ala Glu Pro Gly Glu Ala Ala Ile Lys Leu Thr Ser Ser Ala Gly
                405                 410                 415

Val Leu Ser Ala Glu Gly Val Gly Glu Ile Leu Pro Ser Val Asn Glu
            420                 425                 430

Thr Arg Ser Leu Gln Ala Cys Glu Ala Tyr Asn Ile Ile Asp Lys Ala
            435                 440                 445

Glu Gly Val Gly Glu Ile Leu Pro Ser Val Asn Glu Thr Arg Ser Leu
450                 455                 460

Gln Ala Cys Glu Ala Tyr Asn Ile Ile Asp Lys Arg Phe Gly Phe Phe
465                 470                 475                 480

Gln Val Val Asn Asn Asn Tyr Asp Arg Trp Gly Thr Tyr Ala Ile Gly
                485                 490                 495

Gly Ser Ser Ala Pro Thr Ile Leu Arg Phe Gly Phe Gln Val Val
            500                 505                 510

Asn Asn Asn Tyr Asp Arg Trp Gly Thr Tyr Ala Ile Gly Gly Ser Ser
            515                 520                 525

Ala Pro Thr Ile Leu His His His His
530                 535
```

<210> SEQ ID NO 27
<211> LENGTH: 551

```
<212> TYPE: PRT
<213> ORGANISM: Artificial Sequence
<220> FEATURE:
<223> OTHER INFORMATION: K4BHis

<400> SEQUENCE: 27
```

Ser Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu Ser Arg
            20                  25                  30

Phe Gly Phe Phe Gln Val Val Asn Asn Asn Tyr Asp Arg Trp Gly Thr
        35                  40                  45

Tyr Ala Ile Gly Gly Ser Ser Ala Pro Thr Ile Leu Ala Glu Gly Val
    50                  55                  60

Gly Glu Ile Leu Pro Ser Val Asn Glu Thr Arg Ser Leu Gln Ala Ser
65                  70                  75                  80

Glu Ala Tyr Asn Ile Ile Asp Lys Ser Ala Glu Gly Val Gly Glu Ile
                85                  90                  95

Leu Pro Ser Val Asn Glu Thr Arg Ser Leu Gln Ala Ser Glu Ala Tyr
            100                 105                 110

Asn Ile Ile Asp Lys Ser Ser Asp Pro Val Leu Thr Pro Val Gln Ser
        115                 120                 125

Ala Gly Met Ile Pro Ala Glu Pro Gly Glu Ala Ala Ile Lys Leu Thr
    130                 135                 140

Ser Ser Ala Gly Val Leu Ser Ser Asp Pro Val Leu Thr Pro Val
145                 150                 155                 160

Gln Ser Ala Gly Met Ile Pro Ala Glu Pro Gly Glu Ala Ala Ile Lys
                165                 170                 175

Leu Thr Ser Ser Ala Gly Val Leu Ser Ser Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
    210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Pro Ala Ser Thr Asn Arg Gln Ser Gly Arg
        275                 280                 285

Gln Pro Thr Pro Ile Ser Pro Pro Leu Arg Asp Ser His Pro Gln Ala
    290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg
            340                 345                 350

Thr Gly Asp Pro Val Thr Asn Ser Asp Pro Val Leu Thr Pro Val Gln
        355                 360                 365

Ser Ala Gly Met Ile Pro Ala Glu Pro Gly Glu Ala Ala Ile Lys Leu
    370                 375                 380

```
Thr Ser Ser Ala Gly Val Leu Ser Ser Asp Pro Val Leu Thr Pro
385                 390                 395                 400

Val Gln Ser Ala Gly Met Ile Pro Ala Glu Pro Gly Glu Ala Ala Ile
            405                 410                 415

Lys Leu Thr Ser Ser Ala Gly Val Leu Ser Ser Ala Glu Gly Val Gly
            420                 425                 430

Glu Ile Leu Pro Ser Val Asn Glu Thr Arg Ser Leu Gln Ala Ser Glu
            435                 440                 445

Ala Tyr Asn Ile Ile Asp Lys Ser Ala Glu Gly Val Gly Glu Ile Leu
            450                 455                 460

Pro Ser Val Asn Glu Thr Arg Ser Leu Gln Ala Ser Glu Ala Tyr Asn
465                 470                 475                 480

Ile Ile Asp Lys Ser Ser Arg Phe Gly Phe Phe Gln Val Val Asn Asn
            485                 490                 495

Asn Tyr Asp Arg Trp Gly Thr Tyr Ala Ile Gly Gly Ser Ser Ala Pro
            500                 505                 510

Thr Ile Leu Ser Arg Phe Gly Phe Phe Gln Val Val Asn Asn Asn Tyr
            515                 520                 525

Asp Arg Trp Gly Thr Tyr Ala Ile Gly Gly Ser Ser Ala Pro Thr Ile
            530                 535                 540

Leu His His His His His His
545                 550

<210> SEQ ID NO 28
<211> LENGTH: 541
<212> TYPE: PRT
<213> ORGANISM: Artificial Sequence
<220> FEATURE:
<223> OTHER INFORMATION: K4Cvar

<400> SEQUENCE: 28

Ser Arg His Gly Phe Phe Gln Val Val Asn Asn Tyr Asp Lys Trp
1               5                   10                  15

Gly Ser Tyr Ala Ile Gly Gly Ser Ala Ser Pro Thr Ile Leu Ser Arg
            20                  25                  30

His Gly Phe Phe Gln Val Val Asn Asn Asn Tyr Asp Lys Trp Gly Ser
            35                  40                  45

Tyr Ala Ile Gly Gly Ser Ala Ser Pro Thr Ile Leu Ala Glu Asp Leu
50                  55                  60

Gln Glu Ile Leu Pro Val Asn Glu Thr Arg Arg Leu Thr Thr Ser Gly
65                  70                  75                  80

Ala Tyr Asn Ile Ile Asp Gly Ser Ala Glu Asp Leu Gln Glu Ile Leu
            85                  90                  95

Pro Val Asn Glu Thr Arg Arg Leu Thr Thr Ser Gly Ala Tyr Asn Ile
            100                 105                 110

Ile Asp Gly Ser Val Asp Pro Val Leu Thr Pro Glu Gln Ser Ala Gly
            115                 120                 125

Met Ile Pro Ala Glu Pro Gly Glu Ser Ala Leu Ser Leu Thr Ser Ser
            130                 135                 140

Ala Gly Val Leu Ser Ser Val Asp Pro Val Leu Thr Pro Glu Gln Ser
145                 150                 155                 160

Ala Gly Met Ile Pro Ala Glu Pro Gly Glu Ser Ala Leu Ser Leu Thr
            165                 170                 175

Ser Ser Ala Gly Val Leu Ser Ser Gly Gly Trp Ser Ser Lys Pro Arg
            180                 185                 190
```

```
Lys Gly Met Gly Thr Asn Leu Ser Val Pro Asn Pro Leu Gly Phe Phe
            195                 200                 205

Pro Asp His Gln Leu Asp Pro Ala Phe Gly Ala Asn Ser Asn Pro
        210                 215                 220

Asp Trp Asp Phe Asn Pro Ile Lys Asp His Trp Pro Ala Ala Asn Gln
225                 230                 235                 240

Val Gly Val Gly Ala Phe Gly Pro Gly Leu Thr Pro His Gly Gly
                245                 250                 255

Ile Leu Gly Trp Ser Pro Gln Ala Gln Gly Ile Leu Thr Thr Val Ser
                260                 265                 270

Thr Ile Pro Pro Pro Ala Ser Thr Asn Arg Gln Ser Gly Arg Gln Pro
            275                 280                 285

Thr Pro Ile Ser Pro Pro Leu Arg Asp Ser His Pro Gln Ala Met Gln
        290                 295                 300

Trp Asn Ser Thr Ala Phe His Gln Ala Leu Gln Asp Pro Arg Val Arg
305                 310                 315                 320

Gly Leu Tyr Phe Pro Ala Gly Gly Ser Ser Gly Thr Val Asn Pro
                325                 330                 335

Ala Pro Asn Ile Ala Ser His Ile Ser Ser Ile Ser Ala Arg Thr Gly
                340                 345                 350

Asp Pro Val Thr Asn Val Asp Pro Val Leu Thr Pro Glu Gln Ser Ala
            355                 360                 365

Gly Met Ile Pro Ala Glu Pro Gly Glu Ser Ala Leu Ser Leu Thr Ser
        370                 375                 380

Ser Ala Gly Val Leu Ser Ser Val Asp Pro Val Leu Thr Pro Glu Gln
385                 390                 395                 400

Ser Ala Gly Met Ile Pro Ala Glu Pro Gly Glu Ser Ala Leu Ser Leu
                405                 410                 415

Thr Ser Ser Ala Gly Val Leu Ser Ser Ala Glu Asp Leu Gln Glu Ile
                420                 425                 430

Leu Pro Val Asn Glu Thr Arg Arg Leu Thr Thr Ser Gly Ala Tyr Asn
            435                 440                 445

Ile Ile Asp Gly Ser Ala Glu Asp Leu Gln Glu Ile Leu Pro Val Asn
450                 455                 460

Glu Thr Arg Arg Leu Thr Thr Ser Gly Ala Tyr Asn Ile Ile Asp Gly
465                 470                 475                 480

Ser Ser Arg His Gly Phe Phe Gln Val Val Asn Asn Tyr Asp Lys
                485                 490                 495

Trp Gly Ser Tyr Ala Ile Gly Gly Ser Ala Ser Pro Thr Ile Leu Ser
                500                 505                 510

Arg His Gly Phe Phe Gln Val Val Asn Asn Tyr Asp Lys Trp Gly
                515                 520                 525

Ser Tyr Ala Ile Gly Gly Ser Ala Ser Pro Thr Ile Leu
            530                 535                 540

<210> SEQ ID NO 29
<211> LENGTH: 543
<212> TYPE: PRT
<213> ORGANISM: Artificial Sequence
<220> FEATURE:
<223> OTHER INFORMATION: K4Dvar

<400> SEQUENCE: 29

Ser Arg His Gly Phe Phe Gln Val Val Asn Asn Tyr Asp Lys Trp
1               5                   10                  15
```

-continued

Gly Ser Tyr Ala Ile Gly Gly Ser Ala Ser Pro Thr Ile Leu Ser Arg
            20                  25                  30

His Gly Phe Phe Gln Val Val Asn Asn Tyr Asp Lys Trp Gly Ser
        35                  40                  45

Tyr Ala Ile Gly Gly Ser Ala Ser Pro Thr Ile Leu Ala Glu Asp Leu
        50                  55                  60

Gln Glu Ile Leu Pro Val Asn Glu Thr Arg Arg Leu Thr Thr Ser Gly
65                  70                  75                  80

Ala Tyr Asn Ile Ile Asp Gly Ser Ala Glu Asp Leu Gln Glu Ile Leu
                85                  90                  95

Pro Val Asn Glu Thr Arg Arg Leu Thr Thr Ser Gly Ala Tyr Asn Ile
            100                 105                 110

Ile Asp Gly Ser Val Asp Pro Val Leu Thr Pro Glu Gln Ser Ala Gly
        115                 120                 125

Met Ile Pro Ala Glu Pro Gly Glu Ser Ala Leu Ser Leu Thr Ser Ser
        130                 135                 140

Ala Gly Val Leu Ser Ser Val Asp Pro Val Leu Thr Pro Glu Gln Ser
145                 150                 155                 160

Ala Gly Met Ile Pro Ala Glu Pro Gly Glu Ser Ala Leu Ser Leu Thr
            165                 170                 175

Ser Ser Ala Gly Val Leu Ser Ser Gly Gly Trp Ser Ser Lys Pro Arg
            180                 185                 190

Lys Gly Met Gly Thr Asn Leu Ser Val Pro Asn Pro Leu Gly Phe Phe
            195                 200                 205

Pro Asp His Gln Leu Asp Pro Ala Phe Gly Ala Asn Ser Asn Asn Pro
        210                 215                 220

Asp Trp Asp Phe Asn Pro Ile Lys Asp His Trp Pro Ala Ala Asn Gln
225                 230                 235                 240

Val Gly Val Gly Ala Phe Gly Pro Gly Leu Thr Pro Pro His Gly Gly
                245                 250                 255

Ile Leu Gly Trp Ser Pro Gln Ala Gln Gly Ile Leu Thr Thr Val Ser
            260                 265                 270

Thr Ile Pro Pro Pro Ala Ser Thr Asn Arg Gln Ser Gly Arg Gln Pro
        275                 280                 285

Thr Pro Ile Ser Pro Pro Leu Arg Asp Ser His Pro Gln Ala Met Gln
        290                 295                 300

Trp Asn Ser Thr Ala Phe His Gln Ala Leu Gln Asp Pro Arg Val Arg
305                 310                 315                 320

Gly Leu Tyr Phe Pro Ala Gly Gly Ser Ser Gly Thr Val Asn Pro
            325                 330                 335

Ala Pro Asn Ile Ala Ser His Ile Ser Ser Ile Ser Ala Arg Thr Gly
            340                 345                 350

Asp Pro Val Thr Asn Ser Asp Pro Val Leu Thr Pro Val Gln Ser Ala
        355                 360                 365

Gly Met Ile Pro Ala Glu Pro Gly Glu Ala Ala Ile Lys Leu Thr Ser
        370                 375                 380

Ser Ala Gly Val Leu Ser Ser Asp Pro Val Leu Thr Pro Val Gln
385                 390                 395                 400

Ser Ala Gly Met Ile Pro Ala Glu Pro Gly Glu Ala Ala Ile Lys Leu
            405                 410                 415

Thr Ser Ser Ala Gly Val Leu Ser Ala Glu Gly Val Gly Glu Ile
            420                 425                 430

Leu Pro Ser Val Asn Glu Thr Arg Ser Leu Gln Ala Ser Glu Ala Tyr

```
            435                 440                 445
Asn Ile Ile Asp Lys Ser Ala Glu Gly Val Gly Glu Ile Leu Pro Ser
450                 455                 460
Val Asn Glu Thr Arg Ser Leu Gln Ala Ser Glu Ala Tyr Asn Ile Ile
465                 470                 475                 480
Asp Lys Ser Ser Arg Phe Gly Phe Phe Gln Val Val Asn Asn Asn Tyr
                485                 490                 495
Asp Arg Trp Gly Thr Tyr Ala Ile Gly Gly Ser Ser Ala Pro Thr Ile
                500                 505                 510
Leu Ser Arg Phe Gly Phe Phe Gln Val Val Asn Asn Asn Tyr Asp Arg
                515                 520                 525
Trp Gly Thr Tyr Ala Ile Gly Gly Ser Ser Ala Pro Thr Ile Leu
                530                 535                 540

<210> SEQ ID NO 30
<211> LENGTH: 543
<212> TYPE: PRT
<213> ORGANISM: Artificial Sequence
<220> FEATURE:
<223> OTHER INFORMATION: K4Evar

<400> SEQUENCE: 30

Ser Arg His Gly Phe Phe Gln Val Val Asn Asn Asn Tyr Asp Lys Trp
1               5                   10                  15
Gly Ser Tyr Ala Ile Gly Gly Ser Ala Ser Pro Thr Ile Leu Ser Arg
                20                  25                  30
Phe Gly Phe Phe Gln Val Val Asn Asn Asn Tyr Asp Arg Trp Gly Thr
                35                  40                  45
Tyr Ala Ile Gly Gly Ser Ser Ala Pro Thr Ile Leu Ala Glu Asp Leu
                50                  55                  60
Gln Glu Ile Leu Pro Val Asn Glu Thr Arg Arg Leu Thr Thr Ser Gly
65                  70                  75                  80
Ala Tyr Asn Ile Ile Asp Gly Ser Ala Glu Gly Val Gly Glu Ile Leu
                85                  90                  95
Pro Ser Val Asn Glu Thr Arg Ser Leu Gln Ala Ser Glu Ala Tyr Asn
                100                 105                 110
Ile Ile Asp Lys Ser Val Asp Pro Val Leu Thr Pro Glu Gln Ser Ala
                115                 120                 125
Gly Met Ile Pro Ala Glu Pro Gly Glu Ser Ala Leu Ser Leu Thr Ser
                130                 135                 140
Ser Ala Gly Val Leu Ser Ser Ser Asp Pro Val Leu Thr Pro Val Gln
145                 150                 155                 160
Ser Ala Gly Met Ile Pro Ala Glu Pro Gly Glu Ala Ala Ile Lys Leu
                165                 170                 175
Thr Ser Ser Ala Gly Val Leu Ser Ser Gly Gly Trp Ser Ser Lys Pro
                180                 185                 190
Arg Lys Gly Met Gly Thr Asn Leu Ser Val Pro Asn Pro Leu Gly Phe
                195                 200                 205
Phe Pro Asp His Gln Leu Asp Pro Ala Phe Gly Ala Asn Ser Asn Asn
                210                 215                 220
Pro Asp Trp Asp Phe Asn Pro Ile Lys Asp His Trp Pro Ala Ala Asn
225                 230                 235                 240
Gln Val Gly Val Gly Ala Phe Gly Pro Gly Leu Thr Pro Pro His Gly
                245                 250                 255
Gly Ile Leu Gly Trp Ser Pro Gln Ala Gln Gly Ile Leu Thr Thr Val
```

```
                260                 265                 270
Ser Thr Ile Pro Pro Ala Ser Thr Asn Arg Gln Ser Gly Arg Gln
            275                 280                 285

Pro Thr Pro Ile Ser Pro Pro Leu Arg Asp Ser His Pro Gln Ala Met
290                 295                 300

Gln Trp Asn Ser Thr Ala Phe His Gln Ala Leu Gln Asp Pro Arg Val
305                 310                 315                 320

Arg Gly Leu Tyr Phe Pro Ala Gly Gly Ser Ser Gly Thr Val Asn
            325                 330                 335

Pro Ala Pro Asn Ile Ala Ser His Ile Ser Ser Ile Ser Ala Arg Thr
                340                 345                 350

Gly Asp Pro Val Thr Asn Val Asp Pro Val Leu Thr Pro Glu Gln Ser
            355                 360                 365

Ala Gly Met Ile Pro Ala Glu Pro Gly Glu Ser Ala Leu Ser Leu Thr
            370                 375                 380

Ser Ser Ala Gly Val Leu Ser Ser Ser Asp Pro Val Leu Thr Pro Val
385                 390                 395                 400

Gln Ser Ala Gly Met Ile Pro Ala Glu Pro Gly Glu Ala Ala Ile Lys
                405                 410                 415

Leu Thr Ser Ser Ala Gly Val Leu Ser Ser Ala Glu Asp Leu Gln Glu
            420                 425                 430

Ile Leu Pro Val Asn Glu Thr Arg Arg Leu Thr Thr Ser Gly Ala Tyr
            435                 440                 445

Asn Ile Ile Asp Gly Ser Ala Glu Gly Val Gly Glu Ile Leu Pro Ser
        450                 455                 460

Val Asn Glu Thr Arg Ser Leu Gln Ala Ser Glu Ala Tyr Asn Ile Ile
465                 470                 475                 480

Asp Lys Ser Ser Arg His Gly Phe Phe Gln Val Asn Asn Asn Tyr
            485                 490                 495

Asp Lys Trp Gly Ser Tyr Ala Ile Gly Gly Ser Ala Ser Pro Thr Ile
            500                 505                 510

Leu Ser Arg Phe Gly Phe Phe Gln Val Val Asn Asn Asn Tyr Asp Arg
            515                 520                 525

Trp Gly Thr Tyr Ala Ile Gly Gly Ser Ser Ala Pro Thr Ile Leu
        530                 535                 540

<210> SEQ ID NO 31
<211> LENGTH: 545
<212> TYPE: PRT
<213> ORGANISM: Artificial Sequence
<220> FEATURE:
<223> OTHER INFORMATION: K4F

<400> SEQUENCE: 31

Cys Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu Cys Arg
                20                  25                  30

Phe Gly Phe Phe Gln Val Val Asn Asn Asn Tyr Asp Arg Trp Gly Thr
            35                  40                  45

Tyr Ala Ile Gly Gly Ser Ser Ala Pro Thr Ile Leu Ser Asp Pro Val
        50                  55                  60

Leu Thr Pro Val Gln Ser Ala Gly Met Ile Pro Ala Glu Pro Gly Glu
65                  70                  75                  80

Ala Ala Ile Lys Leu Thr Ser Ser Ala Gly Val Leu Ser Cys Ser Asp
```

```
                    85                  90                  95
Pro Val Leu Thr Pro Val Gln Ser Ala Gly Met Ile Pro Ala Glu Pro
                    100                 105                 110

Gly Glu Ala Ala Ile Lys Leu Thr Ser Ser Ala Gly Val Leu Ser Cys
                    115                 120                 125

Ala Glu Gly Val Gly Glu Ile Leu Pro Ser Val Asn Glu Thr Arg Ser
            130                 135                 140

Leu Gln Ala Cys Glu Ala Tyr Asn Ile Ile Asp Lys Cys Ala Glu Gly
145                 150                 155                 160

Val Gly Glu Ile Leu Pro Ser Val Asn Glu Thr Arg Ser Leu Gln Ala
                165                 170                 175

Cys Glu Ala Tyr Asn Ile Ile Asp Lys Cys Gly Gly Trp Ser Ser Lys
                180                 185                 190

Pro Arg Lys Gly Met Gly Thr Asn Leu Ser Val Pro Asn Pro Leu Gly
                195                 200                 205

Phe Phe Pro Asp His Gln Leu Asp Pro Ala Phe Gly Ala Asn Ser Asn
            210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro Pro His
                    245                 250                 255

Gly Gly Ile Leu Gly Trp Ser Pro Gln Ala Gln Gly Ile Leu Thr Thr
                    260                 265                 270

Val Ser Thr Ile Pro Pro Ala Ser Thr Asn Arg Gln Ser Gly Arg
                275                 280                 285

Gln Pro Thr Pro Ile Ser Pro Pro Leu Arg Asp Ser His Pro Gln Ala
            290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                    325                 330                 335

Asn Pro Ala Pro Asn Ile Ala Ser His Ile Ser Ser Ile Ser Ala Arg
                340                 345                 350

Thr Gly Asp Pro Val Thr Asn Ala Glu Gly Val Gly Glu Ile Leu Pro
            355                 360                 365

Ser Val Asn Glu Thr Arg Ser Leu Gln Ala Cys Glu Ala Tyr Asn Ile
        370                 375                 380

Ile Asp Lys Cys Ala Glu Gly Val Gly Glu Ile Leu Pro Ser Val Asn
385                 390                 395                 400

Glu Thr Arg Ser Leu Gln Ala Cys Glu Ala Tyr Asn Ile Ile Asp Lys
                    405                 410                 415

Cys Ser Asp Pro Val Leu Thr Pro Val Gln Ser Ala Gly Met Ile Pro
                420                 425                 430

Ala Glu Pro Gly Glu Ala Ala Ile Lys Leu Thr Ser Ser Ala Gly Val
            435                 440                 445

Leu Ser Cys Ser Asp Pro Val Leu Thr Pro Val Gln Ser Ala Gly Met
        450                 455                 460

Ile Pro Ala Glu Pro Gly Glu Ala Ala Ile Lys Leu Thr Ser Ser Ala
465                 470                 475                 480

Gly Val Leu Ser Cys Cys Arg Phe Gly Phe Phe Gln Val Val Asn Asn
                    485                 490                 495

Asn Tyr Asp Arg Trp Gly Thr Tyr Ala Ile Gly Gly Ser Ser Ala Pro
                500                 505                 510
```

-continued

```
Thr Ile Leu Cys Arg Phe Gly Phe Phe Gln Val Val Asn Asn Asn Tyr
            515                 520                 525

Asp Arg Trp Gly Thr Tyr Ala Ile Gly Gly Ser Ser Ala Pro Thr Ile
530                 535                 540

Leu
545

<210> SEQ ID NO 32
<211> LENGTH: 545
<212> TYPE: PRT
<213> ORGANISM: Artificial Sequence
<220> FEATURE:
<223> OTHER INFORMATION: K4G

<400> SEQUENCE: 32

Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Cys Ser Asp Pro Val Leu Thr Pro Val Gln Ser Ala Gly Met Ile
        35                  40                  45

Pro Ala Glu Pro Gly Glu Ala Ala Ile Lys Leu Thr Ser Ser Ala Gly
    50                  55                  60

Val Leu Ser Cys Ala Glu Gly Val Gly Glu Ile Leu Pro Ser Val Asn
65                  70                  75                  80

Glu Thr Arg Ser Leu Gln Ala Cys Glu Ala Tyr Asn Ile Ile Asp Lys
                85                  90                  95

Cys Ala Glu Gly Val Gly Glu Ile Leu Pro Ser Val Asn Glu Thr Arg
            100                 105                 110

Ser Leu Gln Ala Cys Glu Ala Tyr Asn Ile Ile Asp Lys Cys Cys Arg
        115                 120                 125

Phe Gly Phe Phe Gln Val Val Asn Asn Asn Tyr Asp Arg Trp Gly Thr
    130                 135                 140

Tyr Ala Ile Gly Gly Ser Ser Ala Pro Thr Ile Leu Cys Arg Phe Gly
145                 150                 155                 160

Phe Phe Gln Val Val Asn Asn Asn Tyr Asp Arg Trp Gly Thr Tyr Ala
                165                 170                 175

Ile Gly Gly Ser Ser Ala Pro Thr Ile Leu Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
    210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Ala Ser Thr Asn Arg Gln Ser Gly Arg
        275                 280                 285

Gln Pro Thr Pro Ile Ser Pro Leu Arg Asp Ser His Pro Gln Ala
    290                 295                 300

Met Gln Trp Asn Ser Thr Ala Phe His Gln Ala Leu Gln Asp Pro Arg
305                 310                 315                 320
```

```
Val Arg Gly Leu Tyr Phe Pro Ala Gly Gly Ser Ser Gly Thr Val
            325                 330                 335

Asn Pro Ala Pro Asn Ile Ala Ser His Ile Ser Ser Ile Ser Ala Arg
            340                 345                 350

Thr Gly Asp Pro Val Thr Asn Cys Arg Phe Gly Phe Phe Gln Val Val
            355                 360                 365

Asn Asn Asn Tyr Asp Arg Trp Gly Thr Tyr Ala Ile Gly Gly Ser Ser
370                 375                 380

Ala Pro Thr Ile Leu Cys Arg Phe Gly Phe Phe Gln Val Val Asn Asn
385                 390                 395                 400

Asn Tyr Asp Arg Trp Gly Thr Tyr Ala Ile Gly Gly Ser Ser Ala Pro
            405                 410                 415

Thr Ile Leu Ala Glu Gly Val Gly Glu Ile Leu Pro Ser Val Asn Glu
            420                 425                 430

Thr Arg Ser Leu Gln Ala Cys Glu Ala Tyr Asn Ile Ile Asp Lys Cys
            435                 440                 445

Ala Glu Gly Val Gly Glu Ile Leu Pro Ser Val Asn Glu Thr Arg Ser
            450                 455                 460

Leu Gln Ala Cys Glu Ala Tyr Asn Ile Ile Asp Lys Cys Ser Asp Pro
465                 470                 475                 480

Val Leu Thr Pro Val Gln Ser Ala Gly Met Ile Pro Ala Glu Pro Gly
            485                 490                 495

Glu Ala Ala Ile Lys Leu Thr Ser Ser Ala Gly Val Leu Ser Cys Ser
            500                 505                 510

Asp Pro Val Leu Thr Pro Val Gln Ser Ala Gly Met Ile Pro Ala Glu
            515                 520                 525

Pro Gly Glu Ala Ala Ile Lys Leu Thr Ser Ser Ala Gly Val Leu Ser
            530                 535                 540

Cys
545

<210> SEQ ID NO 33
<211> LENGTH: 545
<212> TYPE: PRT
<213> ORGANISM: Artificial Sequence
<220> FEATURE:
<223> OTHER INFORMATION: K4H

<400> SEQUENCE: 33

Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Cys Ser Asp Pro Val Leu Thr Pro Val Gln Ser Ala Gly Met Ile
            35                  40                  45

Pro Ala Glu Pro Gly Glu Ala Ala Ile Lys Leu Thr Ser Ser Ala Gly
            50                  55                  60

Val Leu Ser Cys Ser Asp Pro Val Leu Thr Pro Val Gln Ser Ala Gly
65                  70                  75                  80

Met Ile Pro Ala Glu Pro Gly Glu Ala Ala Ile Lys Leu Thr Ser Ser
            85                  90                  95

Ala Gly Val Leu Ser Cys Ser Asp Pro Val Leu Thr Pro Val Gln Ser
            100                 105                 110

Ala Gly Met Ile Pro Ala Glu Pro Gly Glu Ala Ala Ile Lys Leu Thr
            115                 120                 125
```

```
Ser Ser Ala Gly Val Leu Ser Cys Cys Arg Phe Gly Phe Gln Val
        130             135             140

Val Asn Asn Asn Tyr Asp Arg Trp Gly Thr Tyr Ala Ile Gly Gly Ser
145             150             155             160

Ser Ala Pro Thr Ile Leu Cys Arg Phe Gly Phe Phe Gln Val Val Asn
                165             170             175

Asn Asn Tyr Asp Arg Trp Gly Thr Tyr Ala Ile Gly Gly Ser Ser Ala
            180             185             190

Pro Thr Ile Leu Cys Arg Phe Gly Phe Phe Gln Val Asn Asn Asn
        195             200             205

Tyr Asp Arg Trp Gly Thr Tyr Ala Ile Gly Gly Ser Ser Ala Pro Thr
    210             215             220

Ile Leu Cys Arg Phe Gly Phe Phe Gln Val Val Asn Asn Asn Tyr Asp
225             230             235             240

Arg Trp Gly Thr Tyr Ala Ile Gly Gly Ser Ser Ala Pro Thr Ile Leu
                245             250             255

Gly Gly Trp Ser Ser Lys Pro Arg Lys Gly Met Gly Thr Asn Leu Ser
            260             265             270

Val Pro Asn Pro Leu Gly Phe Phe Pro Asp His Gln Leu Asp Pro Ala
        275             280             285

Phe Gly Ala Asn Ser Asn Asn Pro Asp Trp Asp Phe Asn Pro Ile Lys
    290             295             300

Asp His Trp Pro Ala Ala Asn Gln Val Gly Val Gly Ala Phe Gly Pro
305             310             315             320

Gly Leu Thr Pro Pro His Gly Gly Ile Leu Gly Trp Ser Pro Gln Ala
                325             330             335

Gln Gly Ile Leu Thr Thr Val Ser Thr Ile Pro Pro Pro Ala Ser Thr
            340             345             350

Asn Arg Gln Ser Gly Arg Gln Pro Thr Pro Ile Ser Pro Pro Leu Arg
            355             360             365

Asp Ser His Pro Gln Ala Met Gln Trp Asn Ser Thr Ala Phe His Gln
            370             375             380

Ala Leu Gln Asp Pro Arg Val Arg Gly Leu Tyr Phe Pro Ala Gly Gly
385             390             395             400

Ser Ser Ser Gly Thr Val Asn Pro Ala Pro Asn Ile Ala Ser His Ile
                405             410             415

Ser Ser Ile Ser Ala Arg Thr Gly Asp Pro Val Thr Asn Ala Glu Gly
            420             425             430

Val Gly Glu Ile Leu Pro Ser Val Asn Glu Thr Arg Ser Leu Gln Ala
            435             440             445

Cys Glu Ala Tyr Asn Ile Ile Asp Lys Cys Ala Glu Gly Val Gly Glu
450             455             460

Ile Leu Pro Ser Val Asn Glu Thr Arg Ser Leu Gln Ala Cys Glu Ala
465             470             475             480

Tyr Asn Ile Ile Asp Lys Cys Ala Glu Gly Val Gly Glu Ile Leu Pro
                485             490             495

Ser Val Asn Glu Thr Arg Ser Leu Gln Ala Cys Glu Ala Tyr Asn Ile
            500             505             510

Ile Asp Lys Cys Ala Glu Gly Val Gly Glu Ile Leu Pro Ser Val Asn
            515             520             525

Glu Thr Arg Ser Leu Gln Ala Cys Glu Ala Tyr Asn Ile Ile Asp Lys
            530             535             540
```

Cys
545

<210> SEQ ID NO 34
<211> LENGTH: 452
<212> TYPE: PRT
<213> ORGANISM: Artificial Sequence
<220> FEATURE:
<223> OTHER INFORMATION: K4I

<400> SEQUENCE: 34

```
Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Cys Ser Asp Pro Val Leu Thr Pro Val Gln Ser Ala Gly Met Ile
        35                  40                  45

Pro Ala Glu Pro Gly Glu Ala Ala Ile Lys Leu Thr Ser Ser Ala Gly
    50                  55                  60

Val Leu Ser Cys Ser Asp Pro Val Leu Thr Pro Val Gln Ser Ala Gly
65                  70                  75                  80

Met Ile Pro Ala Glu Pro Gly Glu Ala Ala Ile Lys Leu Thr Ser Ser
                85                  90                  95

Ala Gly Val Leu Ser Cys Cys Arg Phe Gly Phe Phe Gln Val Val Asn
            100                 105                 110

Asn Tyr Asp Arg Trp Gly Thr Tyr Ala Ile Gly Gly Ser Ser Ala
        115                 120                 125

Pro Thr Ile Leu Cys Arg Phe Gly Phe Phe Gln Val Val Asn Asn Asn
    130                 135                 140

Tyr Asp Arg Trp Gly Thr Tyr Ala Ile Gly Gly Ser Ser Ala Pro Thr
145                 150                 155                 160

Ile Leu Cys Arg Phe Gly Phe Phe Gln Val Val Asn Asn Asn Tyr Asp
                165                 170                 175

Arg Trp Gly Thr Tyr Ala Ile Gly Gly Ser Ser Ala Pro Thr Ile Leu
            180                 185                 190

Gly Gly Trp Ser Ser Lys Pro Arg Lys Gly Met Gly Thr Asn Leu Ser
        195                 200                 205

Val Pro Asn Pro Leu Gly Phe Phe Pro Asp His Gln Leu Asp Pro Ala
    210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Ala Ser Thr
        275                 280                 285

Asn Arg Gln Ser Gly Arg Gln Pro Thr Pro Ile Ser Pro Pro Leu Arg
    290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335

Ser Ser Ser Gly Thr Val Asn Pro Ala Pro Asn Ile Ala Ser His Ile
            340                 345                 350
```

```
Ser Ser Ile Ser Ala Arg Thr Gly Asp Pro Val Thr Asn Ala Glu Gly
            355                 360                 365

Val Gly Glu Ile Leu Pro Ser Val Asn Glu Thr Arg Ser Leu Gln Ala
        370                 375                 380

Cys Glu Ala Tyr Asn Ile Ile Asp Lys Cys Ala Glu Gly Val Gly Glu
385                 390                 395                 400

Ile Leu Pro Ser Val Asn Glu Thr Arg Ser Leu Gln Ala Cys Glu Ala
                405                 410                 415

Tyr Asn Ile Ile Asp Lys Cys Ala Glu Gly Val Gly Glu Ile Leu Pro
            420                 425                 430

Ser Val Asn Glu Thr Arg Ser Leu Gln Ala Cys Glu Ala Tyr Asn Ile
        435                 440                 445

Ile Asp Lys Cys
    450

<210> SEQ ID NO 35
<211> LENGTH: 452
<212> TYPE: PRT
<213> ORGANISM: Artificial Sequence
<220> FEATURE:
<223> OTHER INFORMATION: K4J

<400> SEQUENCE: 35

Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Ser Ser Asp Pro Val Leu Thr Pro Val Gln Ser Ala Gly Met Ile
        35                  40                  45

Pro Ala Glu Pro Gly Glu Ala Ala Ile Lys Leu Thr Ser Ser Ala Gly
    50                  55                  60

Val Leu Ser Ser Ser Asp Pro Val Leu Thr Pro Val Gln Ser Ala Gly
65                  70                  75                  80

Met Ile Pro Ala Glu Pro Gly Glu Ala Ala Ile Lys Leu Thr Ser Ser
                85                  90                  95

Ala Gly Val Leu Ser Ser Ser Arg Phe Gly Phe Phe Gln Val Val Asn
            100                 105                 110

Asn Asn Tyr Asp Arg Trp Gly Thr Tyr Ala Ile Gly Gly Ser Ser Ala
        115                 120                 125

Pro Thr Ile Leu Ser Arg Phe Gly Phe Phe Gln Val Val Asn Asn Asn
    130                 135                 140

Tyr Asp Arg Trp Gly Thr Tyr Ala Ile Gly Gly Ser Ser Ala Pro Thr
145                 150                 155                 160

Ile Leu Ser Arg Phe Gly Phe Phe Gln Val Val Asn Asn Asn Tyr Asp
                165                 170                 175

Arg Trp Gly Thr Tyr Ala Ile Gly Gly Ser Ser Ala Pro Thr Ile Leu
            180                 185                 190

Gly Gly Trp Ser Ser Lys Pro Arg Lys Gly Met Gly Thr Asn Leu Ser
        195                 200                 205

Val Pro Asn Pro Leu Gly Phe Phe Pro Asp His Gln Leu Asp Pro Ala
    210                 215                 220

Phe Gly Ala Asn Ser Asn Asn Pro Asp Trp Asp Phe Asn Pro Ile Lys
225                 230                 235                 240

Asp His Trp Pro Ala Ala Asn Gln Val Gly Val Gly Ala Phe Gly Pro
                245                 250                 255
```

```
Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Ala Ser Thr
        275                 280                 285

Asn Arg Gln Ser Gly Arg Gln Pro Thr Pro Ile Ser Pro Pro Leu Arg
    290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
                325                 330                 335

Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Ala Glu Gly
            355                 360                 365

Val Gly Glu Ile Leu Pro Ser Val Asn Glu Thr Arg Ser Leu Gln Ala
        370                 375                 380

Ser Glu Ala Tyr Asn Ile Ile Asp Lys Ser Ala Glu Gly Val Gly Glu
385                 390                 395                 400

Ile Leu Pro Ser Val Asn Glu Thr Arg Ser Leu Gln Ala Ser Glu Ala
                405                 410                 415

Tyr Asn Ile Ile Asp Lys Ser Ala Glu Gly Val Gly Glu Ile Leu Pro
            420                 425                 430

Ser Val Asn Glu Thr Arg Ser Leu Gln Ala Ser Glu Ala Tyr Asn Ile
            435                 440                 445

Ile Asp Lys Ser
    450

<210> SEQ ID NO 36
<211> LENGTH: 547
<212> TYPE: PRT
<213> ORGANISM: Artificial Sequence
<220> FEATURE:
<223> OTHER INFORMATION: K4CHis

<400> SEQUENCE: 36

Cys Arg His Gly Phe Phe Gln Val Val Asn Asn Tyr Asp Lys Trp
1               5                   10                  15

Gly Ser Tyr Ala Ile Gly Gly Ser Ala Ser Pro Thr Ile Leu Cys Arg
            20                  25                  30

His Gly Phe Phe Gln Val Val Asn Asn Tyr Asp Lys Trp Gly Ser
        35                  40                  45

Tyr Ala Ile Gly Gly Ser Ala Ser Pro Thr Ile Leu Ala Glu Asp Leu
    50                  55                  60

Gln Glu Ile Leu Pro Val Asn Glu Thr Arg Arg Leu Thr Thr Ser Gly
65                  70                  75                  80

Ala Tyr Asn Ile Ile Asp Gly Cys Ala Glu Asp Leu Gln Glu Ile Leu
                85                  90                  95

Pro Val Asn Glu Thr Arg Arg Leu Thr Thr Ser Gly Ala Tyr Asn Ile
            100                 105                 110

Ile Asp Gly Cys Val Asp Pro Val Leu Thr Pro Glu Gln Ser Ala Gly
        115                 120                 125

Met Ile Pro Ala Glu Pro Gly Glu Ser Ala Leu Ser Leu Thr Ser Ser
    130                 135                 140

Ala Gly Val Leu Ser Cys Val Asp Pro Val Leu Thr Pro Glu Gln Ser
145                 150                 155                 160
```

```
Ala Gly Met Ile Pro Ala Glu Pro Gly Glu Ser Ala Leu Ser Leu Thr
            165                 170                 175
Ser Ser Ala Gly Val Leu Ser Cys Gly Gly Trp Ser Ser Lys Pro Arg
        180                 185                 190
Lys Gly Met Gly Thr Asn Leu Ser Val Pro Asn Pro Leu Gly Phe Phe
            195                 200                 205
Pro Asp His Gln Leu Asp Pro Ala Phe Gly Ala Asn Ser Asn Asn Pro
        210                 215                 220
Asp Trp Asp Phe Asn Pro Ile Lys Asp His Trp Pro Ala Ala Asn Gln
225                 230                 235                 240
Val Gly Val Gly Ala Phe Gly Pro Gly Leu Thr Pro Pro His Gly Gly
                245                 250                 255
Ile Leu Gly Trp Ser Pro Gln Ala Gln Gly Ile Leu Thr Thr Val Ser
            260                 265                 270
Thr Ile Pro Pro Pro Ala Ser Thr Asn Arg Gln Ser Gly Arg Gln Pro
        275                 280                 285
Thr Pro Ile Ser Pro Pro Leu Arg Asp Ser His Pro Gln Ala Met Gln
            290                 295                 300
Trp Asn Ser Thr Ala Phe His Gln Ala Leu Gln Asp Pro Arg Val Arg
305                 310                 315                 320
Gly Leu Tyr Phe Pro Ala Gly Gly Ser Ser Ser Gly Thr Val Asn Pro
                325                 330                 335
Ala Pro Asn Ile Ala Ser His Ile Ser Ser Ile Ser Ala Arg Thr Gly
            340                 345                 350
Asp Pro Val Thr Asn Val Asp Pro Val Leu Thr Pro Glu Gln Ser Ala
        355                 360                 365
Gly Met Ile Pro Ala Glu Pro Gly Glu Ser Ala Leu Ser Leu Thr Ser
        370                 375                 380
Ser Ala Gly Val Leu Ser Cys Val Asp Pro Val Leu Thr Pro Glu Gln
385                 390                 395                 400
Ser Ala Gly Met Ile Pro Ala Glu Pro Gly Glu Ser Ala Leu Ser Leu
                405                 410                 415
Thr Ser Ser Ala Gly Val Leu Ser Cys Ala Glu Asp Leu Gln Glu Ile
            420                 425                 430
Leu Pro Val Asn Glu Thr Arg Arg Leu Thr Thr Ser Gly Ala Tyr Asn
        435                 440                 445
Ile Ile Asp Gly Cys Ala Glu Asp Leu Gln Glu Ile Leu Pro Val Asn
        450                 455                 460
Glu Thr Arg Arg Leu Thr Thr Ser Gly Ala Tyr Asn Ile Ile Asp Gly
465                 470                 475                 480
Cys Cys Arg His Gly Phe Phe Gln Val Asn Asn Asn Tyr Asp Lys
                485                 490                 495
Trp Gly Ser Tyr Ala Ile Gly Gly Ser Ala Ser Pro Thr Ile Leu Cys
            500                 505                 510
Arg His Gly Phe Phe Gln Val Val Asn Asn Asn Tyr Asp Lys Trp Gly
        515                 520                 525
Ser Tyr Ala Ile Gly Gly Ser Ala Ser Pro Thr Ile Leu His His His
        530                 535                 540
His His His
545

<210> SEQ ID NO 37
<211> LENGTH: 545
<212> TYPE: PRT
```

<213> ORGANISM: Artificial Sequence
<220> FEATURE:
<223> OTHER INFORMATION: K4K

<400> SEQUENCE: 37

Leu Arg His Gly Phe Val Gln Val Asn Asn Asn Tyr Glu Arg Trp
1               5                   10                  15

Gly Ser Tyr Ala Leu Gly Gly Ser Ala Gly Pro Thr Ile Leu Leu Arg
            20                  25                  30

His Gly Phe Val Gln Val Asn Asn Asn Tyr Glu Arg Trp Gly Ser
        35                  40                  45

Tyr Ala Leu Gly Gly Ser Ala Gly Pro Thr Ile Leu Ala Glu Asp Leu
    50                  55                  60

Gln Gln Ile Leu Pro Ser Ala Asn Glu Thr Arg Ser Leu Thr Thr Cys
65                  70                  75                  80

Gly Thr Tyr Asn Ile Ile Asp Gly Cys Ala Glu Asp Leu Gln Gln Ile
                85                  90                  95

Leu Pro Ser Ala Asn Glu Thr Arg Ser Leu Thr Thr Cys Gly Thr Tyr
            100                 105                 110

Asn Ile Ile Asp Gly Cys Val Asp Pro Val Leu Thr Pro Glu Gln Asn
        115                 120                 125

Ala Gly Met Ile Pro Ala Glu Pro Gly Glu Ala Val Leu Arg Leu Thr
    130                 135                 140

Ser Ala Gly Val Leu Ser Cys Val Asp Pro Val Leu Thr Pro Glu
145                 150                 155                 160

Gln Asn Ala Gly Met Ile Pro Ala Glu Pro Gly Glu Ala Val Leu Arg
                165                 170                 175

Leu Thr Ser Ser Ala Gly Val Leu Ser Cys Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
    210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Pro Ala Ser Thr Asn Arg Gln Ser Gly Arg
        275                 280                 285

Gln Pro Thr Pro Ile Ser Pro Pro Leu Arg Asp Ser His Pro Gln Ala
    290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg
            340                 345                 350

Thr Gly Asp Pro Val Thr Asn Val Asp Pro Val Leu Thr Pro Glu Gln
        355                 360                 365

Asn Ala Gly Met Ile Pro Ala Glu Pro Gly Glu Ala Val Leu Arg Leu
    370                 375                 380

Thr Ser Ser Ala Gly Val Leu Ser Cys Val Asp Pro Val Leu Thr Pro

```
                385                 390                 395                 400
        Glu Gln Asn Ala Gly Met Ile Pro Ala Glu Pro Gly Glu Ala Val Leu
                        405                 410                 415

Arg Leu Thr Ser Ser Ala Gly Val Leu Ser Cys Ala Glu Asp Leu Gln
                        420                 425                 430

Gln Ile Leu Pro Ser Ala Asn Glu Thr Arg Ser Leu Thr Thr Cys Gly
                        435                 440                 445

Thr Tyr Asn Ile Ile Asp Gly Cys Ala Glu Asp Leu Gln Gln Ile Leu
                        450                 455                 460

Pro Ser Ala Asn Glu Thr Arg Ser Leu Thr Thr Cys Gly Thr Tyr Asn
        465                 470                 475                 480

Ile Ile Asp Gly Cys Leu Arg His Gly Phe Val Gln Val Val Asn Asn
                        485                 490                 495

Asn Tyr Glu Arg Trp Gly Ser Tyr Ala Leu Gly Gly Ser Ala Gly Pro
                        500                 505                 510

Thr Ile Leu Leu Arg His Gly Phe Val Gln Val Val Asn Asn Asn Tyr
                        515                 520                 525

Glu Arg Trp Gly Ser Tyr Ala Leu Gly Gly Ser Ala Gly Pro Thr Ile
            530                 535                 540

Leu
        545

<210> SEQ ID NO 38
<211> LENGTH: 545
<212> TYPE: PRT
<213> ORGANISM: Artificial Sequence
<220> FEATURE:
<223> OTHER INFORMATION: K4L

<400> SEQUENCE: 38

Leu Arg His Gly Phe Val Gln Val Val Asn Asn Asn Tyr Glu Arg Trp
1               5                   10                  15

Gly Ser Tyr Ala Leu Gly Gly Ser Ala Gly Pro Thr Ile Leu Leu Arg
            20                  25                  30

His Gly Phe Val Gln Val Val Asn Asn Asn Tyr Glu Arg Trp Gly Ser
        35                  40                  45

Tyr Ala Leu Gly Gly Ser Ala Gly Pro Thr Ile Leu Ala Glu Asp Leu
    50                  55                  60

Gln Gln Ile Leu Pro Ser Ala Asn Glu Thr Arg Ser Leu Thr Thr Ser
65                  70                  75                  80

Gly Thr Tyr Asn Ile Ile Asp Gly Ser Ala Glu Asp Leu Gln Gln Ile
                85                  90                  95

Leu Pro Ser Ala Asn Glu Thr Arg Ser Leu Thr Thr Ser Gly Thr Tyr
            100                 105                 110

Asn Ile Ile Asp Gly Ser Val Asp Pro Val Leu Thr Pro Glu Gln Asn
        115                 120                 125

Ala Gly Met Ile Pro Ala Glu Pro Gly Glu Ala Val Leu Arg Leu Thr
    130                 135                 140

Ser Ser Ala Gly Val Leu Ser Ser Val Asp Pro Val Leu Thr Pro Glu
145                 150                 155                 160

Gln Asn Ala Gly Met Ile Pro Ala Glu Pro Gly Glu Ala Val Leu Arg
                165                 170                 175

Leu Thr Ser Ser Ala Gly Val Leu Ser Ser Gly Gly Trp Ser Ser Lys
            180                 185                 190

Pro Arg Lys Gly Met Gly Thr Asn Leu Ser Val Pro Asn Pro Leu Gly
```

```
                195                 200                 205
Phe Phe Pro Asp His Gln Leu Asp Pro Ala Phe Gly Ala Asn Ser Asn
210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Ala Ser Thr Asn Arg Gln Ser Gly Arg
        275                 280                 285

Gln Pro Thr Pro Ile Ser Pro Pro Leu Arg Asp Ser His Pro Gln Ala
290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg
            340                 345                 350

Thr Gly Asp Pro Val Thr Asn Val Asp Pro Val Leu Thr Pro Glu Gln
        355                 360                 365

Asn Ala Gly Met Ile Pro Ala Glu Pro Gly Glu Ala Val Leu Arg Leu
    370                 375                 380

Thr Ser Ser Ala Gly Val Leu Ser Ser Val Asp Pro Val Leu Thr Pro
385                 390                 395                 400

Glu Gln Asn Ala Gly Met Ile Pro Ala Glu Pro Gly Glu Ala Val Leu
                405                 410                 415

Arg Leu Thr Ser Ser Ala Gly Val Leu Ser Ser Ala Glu Asp Leu Gln
            420                 425                 430

Gln Ile Leu Pro Ser Ala Asn Glu Thr Arg Ser Leu Thr Thr Ser Gly
        435                 440                 445

Thr Tyr Asn Ile Ile Asp Gly Ser Ala Glu Asp Leu Gln Gln Ile Leu
    450                 455                 460

Pro Ser Ala Asn Glu Thr Arg Ser Leu Thr Thr Ser Gly Thr Tyr Asn
465                 470                 475                 480

Ile Ile Asp Gly Ser Leu Arg His Gly Phe Val Gln Val Val Asn Asn
                485                 490                 495

Asn Tyr Glu Arg Trp Gly Ser Tyr Ala Leu Gly Gly Ser Ala Gly Pro
            500                 505                 510

Thr Ile Leu Leu Arg His Gly Phe Val Gln Val Val Asn Asn Asn Tyr
        515                 520                 525

Glu Arg Trp Gly Ser Tyr Ala Leu Gly Gly Ser Ala Gly Pro Thr Ile
    530                 535                 540

Leu
545

<210> SEQ ID NO 39
<211> LENGTH: 549
<212> TYPE: PRT
<213> ORGANISM: Artificial Sequence
<220> FEATURE:
<223> OTHER INFORMATION: K4M

<400> SEQUENCE: 39

Cys Arg Phe Gly Phe Phe Gln Val Val Asn Asn Asn Tyr Asp Arg Trp
```

-continued

```
1               5                   10                  15
Gly Thr Tyr Ala Ile Gly Gly Ser Ser Ala Pro Thr Ile Leu Cys Arg
                20                  25                  30

Phe Gly Phe Phe Gln Val Val Asn Asn Asn Tyr Asp Arg Trp Gly Thr
                35                  40                  45

Tyr Ala Ile Gly Gly Ser Ser Ala Pro Thr Ile Leu Ala Glu Asp Val
 50                  55                  60

Glu Glu Phe Leu Pro Ser Ala Asn Glu Thr Arg Arg Ser Leu Lys Ala
 65                  70                  75                  80

Cys Glu Ala His Asn Ile Ile Asp Lys Cys Ala Glu Asp Val Glu Glu
                 85                  90                  95

Phe Leu Pro Ser Ala Asn Glu Thr Arg Arg Ser Leu Lys Ala Cys Glu
                100                 105                 110

Ala His Asn Ile Ile Asp Lys Cys Ser Asp Pro Val Leu Thr Pro Glu
                115                 120                 125

Gln Lys Ala Gly Met Ile Pro Ala Glu Pro Gly Glu Ala Val Leu Arg
                130                 135                 140

Leu Thr Ser Ser Ala Gly Val Leu Ser Cys Ser Asp Pro Val Leu Thr
145                 150                 155                 160

Pro Glu Gln Lys Ala Gly Met Ile Pro Ala Glu Pro Gly Glu Ala Val
                165                 170                 175

Leu Arg Leu Thr Ser Ser Ala Gly Val Leu Ser Cys Gly Gly Trp Ser
                180                 185                 190

Ser Lys Pro Arg Lys Gly Met Gly Thr Asn Leu Ser Val Pro Asn Pro
                195                 200                 205

Leu Gly Phe Phe Pro Asp His Gln Leu Asp Pro Ala Phe Gly Ala Asn
210                 215                 220

Ser Asn Asn Pro Asp Trp Asp Phe Asn Pro Ile Lys Asp His Trp Pro
225                 230                 235                 240

Ala Ala Asn Gln Val Gly Val Gly Ala Phe Gly Pro Gly Leu Thr Pro
                245                 250                 255

Pro His Gly Gly Ile Leu Gly Trp Ser Pro Gln Ala Gln Gly Ile Leu
                260                 265                 270

Thr Thr Val Ser Thr Ile Pro Pro Ala Ser Thr Asn Arg Gln Ser
                275                 280                 285

Gly Arg Gln Pro Thr Pro Ile Ser Pro Leu Arg Asp Ser His Pro
                290                 295                 300

Gln Ala Met Gln Trp Asn Ser Thr Ala Phe His Gln Ala Leu Gln Asp
305                 310                 315                 320

Pro Arg Val Arg Gly Leu Tyr Phe Pro Ala Gly Gly Ser Ser Ser Gly
                325                 330                 335

Thr Val Asn Pro Ala Pro Asn Ile Ala Ser His Ile Ser Ser Ile Ser
                340                 345                 350

Ala Arg Thr Gly Asp Pro Val Thr Asn Ser Asp Pro Val Leu Thr Pro
                355                 360                 365

Glu Gln Lys Ala Gly Met Ile Pro Ala Glu Pro Gly Glu Ala Val Leu
                370                 375                 380

Arg Leu Thr Ser Ser Ala Gly Val Leu Ser Cys Ser Asp Pro Val Leu
385                 390                 395                 400

Thr Pro Glu Gln Lys Ala Gly Met Ile Pro Ala Glu Pro Gly Glu Ala
                405                 410                 415

Val Leu Arg Leu Thr Ser Ser Ala Gly Val Leu Ser Cys Ala Glu Asp
                420                 425                 430
```

```
Val Glu Glu Phe Leu Pro Ser Ala Asn Glu Thr Arg Arg Ser Leu Lys
        435                 440                 445

Ala Cys Glu Ala His Asn Ile Ile Asp Lys Cys Ala Glu Asp Val Glu
450                 455                 460

Glu Phe Leu Pro Ser Ala Asn Glu Thr Arg Arg Ser Leu Lys Ala Cys
465                 470                 475                 480

Glu Ala His Asn Ile Ile Asp Lys Cys Cys Arg Phe Gly Phe Phe Gln
                485                 490                 495

Val Val Asn Asn Asn Tyr Asp Arg Trp Gly Thr Tyr Ala Ile Gly Gly
                500                 505                 510

Ser Ser Ala Pro Thr Ile Leu Cys Arg Phe Gly Phe Phe Gln Val Val
            515                 520                 525

Asn Asn Asn Tyr Asp Arg Trp Gly Thr Tyr Ala Ile Gly Gly Ser Ser
            530                 535                 540

Ala Pro Thr Ile Leu
545

<210> SEQ ID NO 40
<211> LENGTH: 549
<212> TYPE: PRT
<213> ORGANISM: Artificial Sequence
<220> FEATURE:
<223> OTHER INFORMATION: K4N

<400> SEQUENCE: 40

Ser Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu Ser Arg
            20                  25                  30

Phe Gly Phe Phe Gln Val Val Asn Asn Asn Tyr Asp Arg Trp Gly Thr
        35                  40                  45

Tyr Ala Ile Gly Gly Ser Ser Ala Pro Thr Ile Leu Ala Glu Asp Val
    50                  55                  60

Glu Glu Phe Leu Pro Ser Ala Asn Glu Thr Arg Arg Ser Leu Lys Ala
65                  70                  75                  80

Ser Glu Ala His Asn Ile Ile Asp Lys Ser Ala Glu Asp Val Glu Glu
                85                  90                  95

Phe Leu Pro Ser Ala Asn Glu Thr Arg Arg Ser Leu Lys Ala Cys Glu
            100                 105                 110

Ala His Asn Ile Ile Asp Lys Ser Ser Asp Pro Val Leu Thr Pro Glu
        115                 120                 125

Gln Lys Ala Gly Met Ile Pro Ala Glu Pro Gly Glu Ala Val Leu Arg
    130                 135                 140

Leu Thr Ser Ser Ala Gly Val Leu Ser Ser Asp Pro Val Leu Thr
145                 150                 155                 160

Pro Glu Gln Lys Ala Gly Met Ile Pro Ala Glu Pro Gly Glu Ala Val
                165                 170                 175

Leu Arg Leu Thr Ser Ser Ala Gly Val Leu Ser Ser Gly Gly Trp Ser
            180                 185                 190

Ser Lys Pro Arg Lys Gly Met Gly Thr Asn Leu Ser Val Pro Asn Pro
        195                 200                 205

Leu Gly Phe Phe Pro Asp His Gln Leu Asp Pro Ala Phe Gly Ala Asn
    210                 215                 220

Ser Asn Asn Pro Asp Trp Asp Phe Asn Pro Ile Lys Asp His Trp Pro
225                 230                 235                 240
```

```
Ala Ala Asn Gln Val Gly Val Gly Ala Phe Gly Pro Gly Leu Thr Pro
                245                 250                 255

Pro His Gly Gly Ile Leu Gly Trp Ser Pro Gln Ala Gln Gly Ile Leu
            260                 265                 270

Thr Thr Val Ser Thr Ile Pro Pro Ala Ser Thr Asn Arg Gln Ser
        275                 280                 285

Gly Arg Gln Pro Thr Pro Ile Ser Pro Pro Leu Arg Asp Ser His Pro
    290                 295                 300

Gln Ala Met Gln Trp Asn Ser Thr Ala Phe His Gln Ala Leu Gln Asp
305                 310                 315                 320

Pro Arg Val Arg Gly Leu Tyr Phe Pro Ala Gly Gly Ser Ser Ser Gly
                325                 330                 335

Thr Val Asn Pro Ala Pro Asn Ile Ala Ser His Ile Ser Ser Ile Ser
            340                 345                 350

Ala Arg Thr Gly Asp Pro Val Thr Asn Ser Asp Pro Val Leu Thr Pro
        355                 360                 365

Glu Gln Lys Ala Gly Met Ile Pro Ala Glu Pro Gly Glu Ala Val Leu
    370                 375                 380

Arg Leu Thr Ser Ser Ala Gly Val Leu Ser Ser Ser Asp Pro Val Leu
385                 390                 395                 400

Thr Pro Glu Gln Lys Ala Gly Met Ile Pro Ala Glu Pro Gly Glu Ala
                405                 410                 415

Val Leu Arg Leu Thr Ser Ser Ala Gly Val Leu Ser Ser Ala Glu Asp
            420                 425                 430

Val Glu Glu Phe Leu Pro Ser Ala Asn Glu Thr Arg Arg Ser Leu Lys
        435                 440                 445

Ala Ser Glu Ala His Asn Ile Ile Asp Lys Ser Ala Glu Asp Val Glu
    450                 455                 460

Glu Phe Leu Pro Ser Ala Asn Glu Thr Arg Arg Ser Leu Lys Ala Ser
465                 470                 475                 480

Glu Ala His Asn Ile Ile Asp Lys Ser Ser Arg Phe Gly Phe Phe Gln
                485                 490                 495

Val Val Asn Asn Asn Tyr Asp Arg Trp Gly Thr Tyr Ala Ile Gly Gly
            500                 505                 510

Ser Ser Ala Pro Thr Ile Leu Ser Arg Phe Gly Phe Phe Gln Val Val
        515                 520                 525

Asn Asn Asn Tyr Asp Arg Trp Gly Thr Tyr Ala Ile Gly Gly Ser Ser
    530                 535                 540

Ala Pro Thr Ile Leu
545

<210> SEQ ID NO 41
<211> LENGTH: 541
<212> TYPE: PRT
<213> ORGANISM: Artificial Sequence
<220> FEATURE:
<223> OTHER INFORMATION: K40

<400> SEQUENCE: 41

Pro Leu Trp Ile Ile Phe Lys Asn Asp Met Val Ile Asn Leu Asn Gln
1               5                   10                  15

Glu Leu Val Val Asn Ser Asp Lys Thr Ile Asp Gly Arg Gly Pro Leu
            20                  25                  30

Trp Ile Ile Phe Lys Asn Asp Met Val Ile Asn Leu Asn Gln Glu Leu
        35                  40                  45
```

```
Val Val Asn Ser Asp Lys Thr Ile Asp Gly Arg Gly Pro Leu Trp Ile
     50                  55                  60
Ile Phe Lys Asn Asp Met Val Ile Asn Leu Asn Gln Glu Leu Val Val
65                  70                  75                  80
Asn Ser Asp Lys Thr Ile Asp Gly Arg Gly Ser Asp Pro Val Leu Thr
                     85                  90                  95
Pro Val Gln Ser Ala Gly Met Ile Pro Ala Glu Pro Gly Glu Ala Ala
                100                 105                 110
Ile Lys Leu Thr Ser Ser Ala Gly Val Leu Ser Cys Ser Asp Pro Val
            115                 120                 125
Leu Thr Pro Val Gln Ser Ala Gly Met Ile Pro Ala Glu Pro Gly Glu
    130                 135                 140
Ala Ala Ile Lys Leu Thr Ser Ser Ala Gly Val Leu Ser Cys Ser Asp
145                 150                 155                 160
Pro Val Leu Thr Pro Val Gln Ser Ala Gly Met Ile Pro Ala Glu Pro
                165                 170                 175
Gly Glu Ala Ala Ile Lys Leu Thr Ser Ser Ala Gly Val Leu Ser Cys
                180                 185                 190
Gly Gly Trp Ser Ser Lys Pro Arg Lys Gly Met Gly Thr Asn Leu Ser
            195                 200                 205
Val Pro Asn Pro Leu Gly Phe Phe Pro Asp His Gln Leu Asp Pro Ala
    210                 215                 220
Phe Gly Ala Asn Ser Asn Asn Pro Asp Trp Asp Phe Asn Pro Ile Lys
225                 230                 235                 240
Asp His Trp Pro Ala Ala Asn Gln Val Gly Val Gly Ala Phe Gly Pro
                245                 250                 255
Gly Leu Thr Pro Pro His Gly Gly Ile Leu Gly Trp Ser Pro Gln Ala
                260                 265                 270
Gln Gly Ile Leu Thr Thr Val Ser Thr Ile Pro Pro Ala Ser Thr
            275                 280                 285
Asn Arg Gln Ser Gly Arg Gln Pro Thr Pro Ile Ser Pro Pro Leu Arg
    290                 295                 300
Asp Ser His Pro Gln Ala Met Gln Trp Asn Ser Thr Ala Phe His Gln
305                 310                 315                 320
Ala Leu Gln Asp Pro Arg Val Arg Gly Leu Tyr Phe Pro Ala Gly Gly
                325                 330                 335
Ser Ser Ser Gly Thr Val Asn Pro Ala Pro Asn Ile Ala Ser His Ile
            340                 345                 350
Ser Ser Ile Ser Ala Arg Thr Gly Asp Pro Val Thr Cys Arg Phe Gly
    355                 360                 365
Phe Phe Gln Val Val Asn Asn Asn Tyr Asp Arg Trp Gly Thr Tyr Ala
    370                 375                 380
Ile Gly Gly Ser Ser Ala Pro Thr Ile Leu Cys Arg Phe Gly Phe Phe
385                 390                 395                 400
Gln Val Val Asn Asn Asn Tyr Asp Arg Trp Gly Thr Tyr Ala Ile Gly
                405                 410                 415
Gly Ser Ser Ala Pro Thr Ile Leu Cys Arg Phe Gly Phe Phe Gln Val
            420                 425                 430
Val Asn Asn Asn Tyr Asp Arg Trp Gly Thr Tyr Ala Ile Gly Gly Ser
    435                 440                 445
Ser Ala Pro Thr Ile Leu Ala Glu Gly Val Gly Glu Ile Leu Pro Ser
    450                 455                 460
```

-continued

```
Val Asn Glu Thr Arg Ser Leu Gln Ala Cys Glu Ala Tyr Asn Ile Ile
465                 470                 475                 480

Asp Lys Cys Ala Glu Gly Val Gly Glu Ile Leu Pro Ser Val Asn Glu
            485                 490                 495

Thr Arg Ser Leu Gln Ala Cys Glu Ala Tyr Asn Ile Ile Asp Lys Cys
        500                 505                 510

Ala Glu Gly Val Gly Glu Ile Leu Pro Ser Val Asn Glu Thr Arg Ser
    515                 520                 525

Leu Gln Ala Cys Glu Ala Tyr Asn Ile Ile Asp Lys Cys
530                 535                 540

<210> SEQ ID NO 42
<211> LENGTH: 541
<212> TYPE: PRT
<213> ORGANISM: Artificial Sequence
<220> FEATURE:
<223> OTHER INFORMATION: K4P

<400> SEQUENCE: 42

Pro Leu Trp Ile Ile Phe Lys Asn Asp Met Val Ile Asn Leu Asn Gln
1               5                   10                  15

Glu Leu Val Val Asn Ser Asp Lys Thr Ile Asp Gly Arg Gly Pro Leu
            20                  25                  30

Trp Ile Ile Phe Lys Asn Asp Met Val Ile Asn Leu Asn Gln Glu Leu
        35                  40                  45

Val Val Asn Ser Asp Lys Thr Ile Asp Gly Arg Gly Pro Leu Trp Ile
    50                  55                  60

Ile Phe Lys Asn Asp Met Val Ile Asn Leu Asn Gln Glu Leu Val Val
65                  70                  75                  80

Asn Ser Asp Lys Thr Ile Asp Gly Arg Gly Cys Arg Phe Gly Phe Phe
            85                  90                  95

Gln Val Val Asn Asn Tyr Asp Arg Trp Gly Thr Tyr Ala Ile Gly
            100                 105                 110

Gly Ser Ser Ala Pro Thr Ile Leu Cys Arg Phe Gly Phe Phe Gln Val
        115                 120                 125

Val Asn Asn Asn Tyr Asp Arg Trp Gly Thr Tyr Ala Ile Gly Gly Ser
    130                 135                 140

Ser Ala Pro Thr Ile Leu Cys Arg Phe Gly Phe Phe Gln Val Val Asn
145                 150                 155                 160

Asn Asn Tyr Asp Arg Trp Gly Thr Tyr Ala Ile Gly Gly Ser Ser Ala
            165                 170                 175

Pro Thr Ile Leu Gly Gly Trp Ser Ser Lys Pro Arg Lys Gly Met Gly
        180                 185                 190

Thr Asn Leu Ser Val Pro Asn Pro Leu Gly Phe Phe Pro Asp His Gln
    195                 200                 205

Leu Asp Pro Ala Phe Gly Ala Asn Ser Asn Asn Pro Asp Trp Asp Phe
210                 215                 220

Asn Pro Ile Lys Asp His Trp Pro Ala Ala Asn Gln Val Gly Val Gly
225                 230                 235                 240

Ala Phe Gly Pro Gly Leu Thr Pro Pro His Gly Gly Ile Leu Gly Trp
            245                 250                 255

Ser Pro Gln Ala Gln Gly Ile Leu Thr Thr Val Ser Thr Ile Pro Pro
        260                 265                 270

Pro Ala Ser Thr Asn Arg Gln Ser Gly Arg Gln Pro Thr Pro Ile Ser
    275                 280                 285
```

```
Pro Pro Leu Arg Asp Ser His Pro Gln Ala Met Gln Trp Asn Ser Thr
    290                 295                 300
Ala Phe His Gln Ala Leu Gln Asp Pro Arg Val Arg Gly Leu Tyr Phe
305                 310                 315                 320
Pro Ala Gly Gly Ser Ser Gly Thr Val Asn Pro Ala Pro Asn Ile
                325                 330                 335
Ala Ser His Ile Ser Ser Ile Ser Ala Arg Thr Gly Asp Pro Val Thr
                340                 345                 350
Ser Asp Pro Val Leu Thr Pro Val Gln Ser Ala Gly Met Ile Pro Ala
            355                 360                 365
Glu Pro Gly Glu Ala Ala Ile Lys Leu Thr Ser Ser Ala Gly Val Leu
370                 375                 380
Ser Cys Ser Asp Pro Val Leu Thr Pro Val Gln Ser Ala Gly Met Ile
385                 390                 395                 400
Pro Ala Glu Pro Gly Glu Ala Ala Ile Lys Leu Thr Ser Ser Ala Gly
                405                 410                 415
Val Leu Ser Cys Ser Asp Pro Val Leu Thr Pro Val Gln Ser Ala Gly
            420                 425                 430
Met Ile Pro Ala Glu Pro Gly Glu Ala Ala Ile Lys Leu Thr Ser Ser
        435                 440                 445
Ala Gly Val Leu Ser Cys Ala Glu Gly Val Gly Glu Ile Leu Pro Ser
450                 455                 460
Val Asn Glu Thr Arg Ser Leu Gln Ala Cys Glu Ala Tyr Asn Ile Ile
465                 470                 475                 480
Asp Lys Cys Ala Glu Gly Val Gly Glu Ile Leu Pro Ser Val Asn Glu
                485                 490                 495
Thr Arg Ser Leu Gln Ala Cys Glu Ala Tyr Asn Ile Ile Asp Lys Cys
            500                 505                 510
Ala Glu Gly Val Gly Glu Ile Leu Pro Ser Val Asn Glu Thr Arg Ser
        515                 520                 525
Leu Gln Ala Cys Glu Ala Tyr Asn Ile Ile Asp Lys Cys
        530                 535                 540

<210> SEQ ID NO 43
<211> LENGTH: 545
<212> TYPE: PRT
<213> ORGANISM: Artificial Sequence
<220> FEATURE:
<223> OTHER INFORMATION: K4Q

<400> SEQUENCE: 43

Ser Arg His Gly Phe Phe Gln Val Val Asn Asn Tyr Asp Lys Trp
1               5                   10                  15
Gly Ser Tyr Ala Ile Gly Gly Ser Ala Ser Pro Thr Ile Leu Ser Arg
                20                  25                  30
Phe Gly Phe Phe Gln Val Val Asn Asn Tyr Asp Arg Trp Gly Thr
            35                  40                  45
Tyr Ala Ile Gly Gly Ser Ser Ala Pro Thr Ile Leu Ala Glu Asp Leu
        50                  55                  60
Gln Glu Ile Leu Pro Val Asn Glu Thr Arg Arg Leu Thr Thr Ser Gly
65                  70                  75                  80
Ala Tyr Asn Ile Ile Asp Gly Ser Ala Glu Asp Val Glu Glu Phe Leu
                85                  90                  95
Pro Ser Ala Asn Glu Thr Arg Arg Ser Leu Lys Ala Cys Glu Ala His
            100                 105                 110
```

```
Asn Ile Ile Asp Lys Cys Val Asp Pro Val Leu Thr Pro Glu Gln Ser
            115                 120                 125

Ala Gly Met Ile Pro Ala Glu Pro Gly Glu Ser Ala Leu Ser Leu Thr
        130                 135                 140

Ser Ser Ala Gly Val Leu Ser Ser Ser Asp Pro Val Leu Thr Pro Glu
145                 150                 155                 160

Gln Lys Ala Gly Met Ile Pro Ala Glu Pro Gly Glu Ala Val Leu Arg
                165                 170                 175

Leu Thr Ser Ser Ala Gly Val Leu Ser Cys Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Pro Ala Ser Thr Asn Arg Gln Ser Gly Arg
        275                 280                 285

Gln Pro Thr Pro Ile Ser Pro Pro Leu Arg Asp Ser His Pro Gln Ala
290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg
            340                 345                 350

Thr Gly Asp Pro Val Thr Asn Ser Asp Pro Val Leu Thr Pro Val Gln
        355                 360                 365

Ser Ala Gly Met Ile Pro Ala Glu Pro Gly Glu Ala Ala Ile Lys Leu
370                 375                 380

Thr Ser Ser Ala Gly Val Leu Ser Cys Val Asp Pro Val Leu Thr Pro
385                 390                 395                 400

Glu Gln Asn Ala Gly Met Ile Pro Ala Glu Pro Gly Glu Ala Val Leu
                405                 410                 415

Arg Leu Thr Ser Ser Ala Gly Val Leu Ser Cys Ala Glu Gly Val Gly
            420                 425                 430

Glu Ile Leu Pro Ser Val Asn Glu Thr Arg Ser Leu Gln Ala Cys Glu
        435                 440                 445

Ala Tyr Asn Ile Ile Asp Lys Cys Ala Glu Asp Leu Gln Gln Ile Leu
450                 455                 460

Pro Ser Ala Asn Glu Thr Arg Ser Leu Thr Thr Cys Gly Thr Tyr Asn
465                 470                 475                 480

Ile Ile Asp Gly Cys Cys Arg Phe Gly Phe Phe Gln Val Val Asn Asn
                485                 490                 495

Asn Tyr Asp Arg Trp Gly Thr Tyr Ala Ile Gly Gly Ser Ser Ala Pro
            500                 505                 510

Thr Ile Leu Leu Arg His Gly Phe Val Gln Val Val Asn Asn Asn Tyr
        515                 520                 525

Glu Arg Trp Gly Ser Tyr Ala Leu Gly Gly Ser Ala Gly Pro Thr Ile
```

Leu
545

<210> SEQ ID NO 44
<211> LENGTH: 545
<212> TYPE: PRT
<213> ORGANISM: Artificial Sequence
<220> FEATURE:
<223> OTHER INFORMATION: K4R

<400> SEQUENCE: 44

Ser Arg His Gly Phe Phe Gln Val Val Asn Asn Asn Tyr Asp Lys Trp
1               5                   10                  15

Gly Ser Tyr Ala Ile Gly Gly Ser Ala Ser Pro Thr Ile Leu Ser Arg
            20                  25                  30

Phe Gly Phe Phe Gln Val Val Asn Asn Asn Tyr Asp Arg Trp Gly Thr
        35                  40                  45

Tyr Ala Ile Gly Gly Ser Ser Ala Pro Thr Ile Leu Ala Glu Asp Leu
    50                  55                  60

Gln Glu Ile Leu Pro Val Asn Glu Thr Arg Arg Leu Thr Thr Ser Gly
65                  70                  75                  80

Ala Tyr Asn Ile Ile Asp Gly Ser Ala Glu Asp Val Glu Glu Phe Leu
                85                  90                  95

Pro Ser Ala Asn Glu Thr Arg Arg Ser Leu Lys Ala Cys Glu Ala His
            100                 105                 110

Asn Ile Ile Asp Lys Ser Val Asp Pro Val Leu Thr Pro Glu Gln Ser
        115                 120                 125

Ala Gly Met Ile Pro Ala Glu Pro Gly Glu Ser Ala Leu Ser Leu Thr
    130                 135                 140

Ser Ser Ala Gly Val Leu Ser Ser Ser Asp Pro Val Leu Thr Pro Glu
145                 150                 155                 160

Gln Lys Ala Gly Met Ile Pro Ala Glu Pro Gly Glu Ala Val Leu Arg
                165                 170                 175

Leu Thr Ser Ser Ala Gly Val Leu Ser Ser Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
    210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Ala Ser Thr Asn Arg Gln Ser Gly Arg
        275                 280                 285

Gln Pro Thr Pro Ile Ser Pro Leu Arg Asp Ser His Pro Gln Ala
    290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg

-continued

```
                  340                 345                 350
Thr Gly Asp Pro Val Thr Asn Ser Asp Pro Val Leu Thr Pro Val Gln
        355                 360                 365

Ser Ala Gly Met Ile Pro Ala Glu Pro Gly Glu Ala Ala Ile Lys Leu
    370                 375                 380

Thr Ser Ser Ala Gly Val Leu Ser Ser Val Asp Pro Val Leu Thr Pro
385                 390                 395                 400

Glu Gln Asn Ala Gly Met Ile Pro Ala Glu Pro Gly Glu Ala Val Leu
                405                 410                 415

Arg Leu Thr Ser Ser Ala Gly Val Leu Ser Ser Ala Glu Gly Val Gly
            420                 425                 430

Glu Ile Leu Pro Ser Val Asn Glu Thr Arg Ser Leu Gln Ala Ser Glu
        435                 440                 445

Ala Tyr Asn Ile Ile Asp Lys Ser Ala Glu Asp Leu Gln Gln Ile Leu
    450                 455                 460

Pro Ser Ala Asn Glu Thr Arg Ser Leu Thr Thr Ser Gly Thr Tyr Asn
465                 470                 475                 480

Ile Ile Asp Gly Ser Ser Arg Phe Gly Phe Phe Gln Val Val Asn Asn
                485                 490                 495

Asn Tyr Asp Arg Trp Gly Thr Tyr Ala Ile Gly Ser Ser Ala Pro
            500                 505                 510

Thr Ile Leu Leu Arg His Gly Phe Val Gln Val Asn Asn Asn Tyr
        515                 520                 525

Glu Arg Trp Gly Ser Tyr Ala Leu Gly Gly Ser Ala Gly Pro Thr Ile
    530                 535                 540

Leu
545

<210> SEQ ID NO 45
<211> LENGTH: 29
<212> TYPE: PRT
<213> ORGANISM: Artificial Sequence
<220> FEATURE:
<223> OTHER INFORMATION: Amb a 1 fragment

<400> SEQUENCE: 45

Ala Glu Gly Val Gly Glu Ile Leu Pro Ser Val Asn Glu Thr Arg Ser
1               5                   10                  15

Leu Gln Ala Cys Glu Ala Tyr Asn Ile Ile Asp Lys Cys
            20                  25

<210> SEQ ID NO 46
<211> LENGTH: 31
<212> TYPE: PRT
<213> ORGANISM: Artificial Sequence
<220> FEATURE:
<223> OTHER INFORMATION: Amb a 1 fragment

<400> SEQUENCE: 46

Trp Arg Gly Lys Ala Asp Trp Glu Asn Asn Arg Gln Ala Leu Ala Asp
1               5                   10                  15

Cys Ala Gln Gly Phe Ala Lys Gly Thr Tyr Gly Gly Lys Trp Cys
            20                  25                  30

<210> SEQ ID NO 47
<211> LENGTH: 31
<212> TYPE: PRT
<213> ORGANISM: Artificial Sequence
<220> FEATURE:
```

```
<223> OTHER INFORMATION: Amb a 1 fragment

<400> SEQUENCE: 47

Gly Asp Val Tyr Thr Val Thr Ser Asn Leu Asp Asp Val Ala Asn
1               5                   10                  15

Pro Lys Glu Gly Thr Leu Arg Phe Ala Ala Ala Gln Asn Arg Cys
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Amb a 1 fragment

<400> SEQUENCE: 48

Pro Leu Trp Ile Ile Phe Lys Asn Asp Met Val Ile Asn Leu Asn Gln
1               5                   10                  15

Glu Leu Val Val Asn Ser Asp Lys Thr Ile Asp Gly Arg Gly Cys
            20                  25                  30

<210> SEQ ID NO 49
<211> LENGTH: 34
<212> TYPE: PRT
<213> ORGANISM: Artificial Sequence
<220> FEATURE:
<223> OTHER INFORMATION: Amb a 1 fragment

<400> SEQUENCE: 49

Val Lys Val Glu Ile Ile Asn Gly Gly Leu Thr Leu Met Asn Val Lys
1               5                   10                  15

Asn Ile Ile Ile His Asn Ile Asn Ile His Asp Val Lys Val Leu Pro
            20                  25                  30

Gly Cys

<210> SEQ ID NO 50
<211> LENGTH: 34
<212> TYPE: PRT
<213> ORGANISM: Artificial Sequence
<220> FEATURE:
<223> OTHER INFORMATION: Amb a 1 fragment

<400> SEQUENCE: 50

Gly Met Ile Lys Ser Asn Asp Gly Pro Pro Ile Leu Arg Gln Ala Ser
1               5                   10                  15

Asp Gly Asp Thr Ile Asn Val Ala Gly Ser Ser Gln Ile Trp Ile Asp
            20                  25                  30

His Cys

<210> SEQ ID NO 51
<211> LENGTH: 32
<212> TYPE: PRT
<213> ORGANISM: Artificial Sequence
<220> FEATURE:
<223> OTHER INFORMATION: Amb a 1 fragment

<400> SEQUENCE: 51

Cys Phe Asp Gly Leu Val Asp Val Thr Leu Gly Ser Thr His Val Thr
1               5                   10                  15

Ile Ser Asn Cys Lys Phe Thr Gln Gln Ser Lys Ala Ile Leu Leu Gly
            20                  25                  30
```

```
<210> SEQ ID NO 52
<211> LENGTH: 31
<212> TYPE: PRT
<213> ORGANISM: Artificial Sequence
<220> FEATURE:
<223> OTHER INFORMATION: Amb a 1 fragment

<400> SEQUENCE: 52

Cys Ala Asp Asp Thr His Val Gln Asp Lys Gly Met Leu Ala Thr Val
1               5                   10                  15

Ala Phe Asn Met Phe Thr Asp Asn Val Asp Gln Arg Met Pro Arg
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Amb a 1 fragment

<400> SEQUENCE: 53

Cys Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu
            20                  25                  30

<210> SEQ ID NO 54
<211> LENGTH: 35
<212> TYPE: PRT
<213> ORGANISM: Artificial Sequence
<220> FEATURE:
<223> OTHER INFORMATION: Amb a 1 fragment

<400> SEQUENCE: 54

Cys Gln Gly Asn Arg Phe Leu Ala Pro Asp Asp Gln Ile Lys Lys Asn
1               5                   10                  15

Val Leu Ala Arg Thr Gly Thr Gly Ala Ala Glu Ser Met Ala Trp Asn
            20                  25                  30

Trp Arg Ser
        35

<210> SEQ ID NO 55
<211> LENGTH: 34
<212> TYPE: PRT
<213> ORGANISM: Artificial Sequence
<220> FEATURE:
<223> OTHER INFORMATION: Amb a 1 fragment

<400> SEQUENCE: 55

Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Cys

<210> SEQ ID NO 56
<211> LENGTH: 429
<212> TYPE: PRT
<213> ORGANISM: Artificial Sequence
<220> FEATURE:
<223> OTHER INFORMATION: K1

<400> SEQUENCE: 56

Cys Arg Phe Gly Phe Phe Gln Val Val Asn Asn Asn Tyr Asp Arg Trp
```

```
1               5                   10                  15
Gly Thr Tyr Ala Ile Gly Gly Ser Ser Ala Pro Thr Ile Leu Cys Arg
                20                  25                  30

Phe Gly Phe Phe Gln Val Val Asn Asn Asn Tyr Asp Arg Trp Gly Thr
                35                  40                  45

Tyr Ala Ile Gly Gly Ser Ser Ala Pro Thr Ile Leu Cys Arg Phe Gly
                50                  55                  60

Phe Phe Gln Val Val Asn Asn Asn Tyr Asp Arg Trp Gly Thr Tyr Ala
65                  70                  75                  80

Ile Gly Gly Ser Ser Ala Pro Thr Ile Leu Cys Arg Phe Gly Phe Phe
                85                  90                  95

Gln Val Val Asn Asn Asn Tyr Asp Arg Trp Gly Thr Tyr Ala Ile Gly
                100                 105                 110

Gly Ser Ser Ala Pro Thr Ile Leu Gly Gly Trp Ser Ser Lys Pro Arg
                115                 120                 125

Lys Gly Met Gly Thr Asn Leu Ser Val Pro Asn Pro Leu Gly Phe Phe
                130                 135                 140

Pro Asp His Gln Leu Asp Pro Ala Phe Gly Ala Asn Ser Asn Asn Pro
145                 150                 155                 160

Asp Trp Asp Phe Asn Pro Ile Lys Asp His Trp Pro Ala Ala Asn Gln
                165                 170                 175

Val Gly Val Gly Ala Phe Gly Pro Gly Leu Thr Pro Pro His Gly Gly
                180                 185                 190

Ile Leu Gly Trp Ser Pro Gln Ala Gln Gly Ile Leu Thr Thr Val Ser
                195                 200                 205

Thr Ile Pro Pro Pro Ala Ser Thr Asn Arg Gln Ser Gly Arg Gln Pro
210                 215                 220

Thr Pro Ile Ser Pro Pro Leu Arg Asp Ser His Pro Gln Ala Met Gln
225                 230                 235                 240

Trp Asn Ser Thr Ala Phe His Gln Ala Leu Gln Asp Pro Arg Val Arg
                245                 250                 255

Gly Leu Tyr Phe Pro Ala Gly Gly Ser Ser Ser Gly Thr Val Asn Pro
                260                 265                 270

Ala Pro Asn Ile Ala Ser His Ile Ser Ser Ile Ser Ala Arg Thr Gly
                275                 280                 285

Asp Pro Val Thr Asn Ser Asp Pro Val Leu Thr Pro Val Gln Ser Ala
                290                 295                 300

Gly Met Ile Pro Ala Glu Pro Gly Glu Ala Ala Ile Lys Leu Thr Ser
305                 310                 315                 320

Ser Ala Gly Val Leu Ser Cys Ser Asp Pro Val Leu Thr Pro Val Gln
                325                 330                 335

Ser Ala Gly Met Ile Pro Ala Glu Pro Gly Glu Ala Ala Ile Lys Leu
                340                 345                 350

Thr Ser Ser Ala Gly Val Leu Ser Cys Ser Asp Pro Val Leu Thr Pro
                355                 360                 365

Val Gln Ser Ala Gly Met Ile Pro Ala Glu Pro Gly Glu Ala Ala Ile
                370                 375                 380

Lys Leu Thr Ser Ser Ala Gly Val Leu Ser Cys Ser Asp Pro Val Leu
385                 390                 395                 400

Thr Pro Val Gln Ser Ala Gly Met Ile Pro Ala Glu Pro Gly Glu Ala
                405                 410                 415

Ala Ile Lys Leu Thr Ser Ser Ala Gly Val Leu Ser Cys
                420                 425
```

```
<210> SEQ ID NO 57
<211> LENGTH: 365
<212> TYPE: PRT
<213> ORGANISM: Artificial Sequence
<220> FEATURE:
<223> OTHER INFORMATION: K2

<400> SEQUENCE: 57
```

| | | | | | | | | | | | | | | |
|---|---|---|---|---|---|---|---|---|---|---|---|---|---|---|
|Cys|Arg|Phe|Gly|Phe|Phe|Gln|Val|Val|Asn|Asn|Asn|Tyr|Asp|Arg|Trp|
|1| | | |5| | | | |10| | | | |15|

| | | | | | | | | | | | | | | |
|---|---|---|---|---|---|---|---|---|---|---|---|---|---|---|
|Gly|Thr|Tyr|Ala|Ile|Gly|Gly|Ser|Ser|Ala|Pro|Thr|Ile|Leu|Cys|Arg|
| | | |20| | | | |25| | | | |30| | |

|Phe|Gly|Phe|Phe|Gln|Val|Val|Asn|Asn|Asn|Tyr|Asp|Arg|Trp|Gly|Thr|
| | | | |35| | | | |40| | | | |45| | |

|Tyr|Ala|Ile|Gly|Gly|Ser|Ser|Ala|Pro|Thr|Ile|Leu|Cys|Arg|Phe|Gly|
| | |50| | | | |55| | | | |60| | | |

|Phe|Phe|Gln|Val|Val|Asn|Asn|Asn|Tyr|Asp|Arg|Trp|Gly|Thr|Tyr|Ala|
|65| | | | |70| | | | |75| | | | |80|

|Ile|Gly|Gly|Ser|Ser|Ala|Pro|Thr|Ile|Leu|Gly|Gly|Trp|Ser|Ser|Lys|
| | | | |85| | | | |90| | | | |95| |

|Pro|Arg|Lys|Gly|Met|Gly|Thr|Asn|Leu|Ser|Val|Pro|Asn|Pro|Leu|Gly|
| | | |100| | | | |105| | | | |110| | |

|Phe|Phe|Pro|Asp|His|Gln|Leu|Asp|Pro|Ala|Phe|Gly|Ala|Asn|Ser|Asn|
| | |115| | | | |120| | | | |125| | | |

|Asn|Pro|Asp|Trp|Asp|Phe|Asn|Pro|Ile|Lys|Asp|His|Trp|Pro|Ala|Ala|
|130| | | | |135| | | | |140| | | | | |

|Asn|Gln|Val|Gly|Val|Gly|Ala|Phe|Gly|Pro|Gly|Leu|Thr|Pro|Pro|His|
|145| | | | |150| | | | |155| | | | |160|

|Gly|Gly|Ile|Leu|Gly|Trp|Ser|Pro|Gln|Ala|Gln|Gly|Ile|Leu|Thr|Thr|
| | | | |165| | | | |170| | | | |175| |

|Val|Ser|Thr|Ile|Pro|Pro|Pro|Ala|Ser|Thr|Asn|Arg|Gln|Ser|Gly|Arg|
| | | |180| | | | |185| | | | |190| | |

|Gln|Pro|Thr|Pro|Ile|Ser|Pro|Pro|Leu|Arg|Asp|Ser|His|Pro|Gln|Ala|
| | | |195| | | | |200| | | | |205| | |

|Met|Gln|Trp|Asn|Ser|Thr|Ala|Phe|His|Gln|Ala|Leu|Gln|Asp|Pro|Arg|
| | |210| | | | |215| | | | |220| | | |

|Val|Arg|Gly|Leu|Tyr|Phe|Pro|Ala|Gly|Gly|Ser|Ser|Ser|Gly|Thr|Val|
|225| | | | |230| | | | |235| | | | |240|

|Asn|Pro|Ala|Pro|Asn|Ile|Ala|Ser|His|Ile|Ser|Ser|Ile|Ser|Ala|Arg|
| | | | |245| | | | |250| | | | |255| |

|Thr|Gly|Asp|Pro|Val|Thr|Asn|Ser|Asp|Pro|Val|Leu|Thr|Pro|Val|Gln|
| | | |260| | | | |265| | | | |270| | |

|Ser|Ala|Gly|Met|Ile|Pro|Ala|Glu|Pro|Gly|Glu|Ala|Ala|Ile|Lys|Leu|
| | | |275| | | | |280| | | | |285| | |

|Thr|Ser|Ser|Ala|Gly|Val|Leu|Ser|Cys|Ser|Asp|Pro|Val|Leu|Thr|Pro|
| | |290| | | | |295| | | | |300| | | |

|Val|Gln|Ser|Ala|Gly|Met|Ile|Pro|Ala|Glu|Pro|Gly|Glu|Ala|Ala|Ile|
|305| | | | |310| | | | |315| | | | |320|

|Lys|Leu|Thr|Ser|Ser|Ala|Gly|Val|Leu|Ser|Cys|Ser|Asp|Pro|Val|Leu|
| | | | |325| | | | |330| | | | |335| |

|Thr|Pro|Val|Gln|Ser|Ala|Gly|Met|Ile|Pro|Ala|Glu|Pro|Gly|Glu|Ala|
| | | |340| | | | |345| | | | |350| | |

|Ala|Ile|Lys|Leu|Thr|Ser|Ser|Ala|Gly|Val|Leu|Ser|Cys|
| | | |355| | | | |360| | | | |365|

```
<210> SEQ ID NO 58
<211> LENGTH: 365
<212> TYPE: PRT
<213> ORGANISM: Artificial Sequence
<220> FEATURE:
<223> OTHER INFORMATION: K3

<400> SEQUENCE: 58

Ser Asp Pro Val Leu Thr Pro Val Gln Ser Ala Gly Met Ile Pro Ala
1               5                   10                  15

Glu Pro Gly Glu Ala Ala Ile Lys Leu Thr Ser Ser Ala Gly Val Leu
            20                  25                  30

Ser Cys Ser Asp Pro Val Leu Thr Pro Val Gln Ser Ala Gly Met Ile
        35                  40                  45

Pro Ala Glu Pro Gly Glu Ala Ala Ile Lys Leu Thr Ser Ser Ala Gly
    50                  55                  60

Val Leu Ser Cys Ser Asp Pro Val Leu Thr Pro Val Gln Ser Ala Gly
65                  70                  75                  80

Met Ile Pro Ala Glu Pro Gly Glu Ala Ala Ile Lys Leu Thr Ser Ser
                85                  90                  95

Ala Gly Val Leu Ser Cys Gly Trp Ser Ser Lys Pro Arg Lys Gly
            100                 105                 110

Met Gly Thr Asn Leu Ser Val Pro Asn Pro Leu Gly Phe Phe Pro Asp
            115                 120                 125

His Gln Leu Asp Pro Ala Phe Gly Ala Asn Ser Asn Asn Pro Asp Trp
        130                 135                 140

Asp Phe Asn Pro Ile Lys Asp His Trp Pro Ala Ala Asn Gln Val Gly
145                 150                 155                 160

Val Gly Ala Phe Gly Pro Gly Leu Thr Pro Pro His Gly Gly Ile Leu
                165                 170                 175

Gly Trp Ser Pro Gln Ala Gln Gly Ile Leu Thr Thr Val Ser Thr Ile
            180                 185                 190

Pro Pro Pro Ala Ser Thr Asn Arg Gln Ser Gly Arg Gln Pro Thr Pro
            195                 200                 205

Ile Ser Pro Pro Leu Arg Asp Ser His Pro Gln Ala Met Gln Trp Asn
        210                 215                 220

Ser Thr Ala Phe His Gln Ala Leu Gln Asp Pro Arg Val Arg Gly Leu
225                 230                 235                 240

Tyr Phe Pro Ala Gly Gly Ser Ser Ser Gly Thr Val Asn Pro Ala Pro
                245                 250                 255

Asn Ile Ala Ser His Ile Ser Ser Ile Ser Ala Arg Thr Gly Asp Pro
            260                 265                 270

Val Thr Asn Cys Arg Phe Gly Phe Phe Gln Val Val Asn Asn Asn Tyr
            275                 280                 285

Asp Arg Trp Gly Thr Tyr Ala Ile Gly Gly Ser Ser Ala Pro Thr Ile
        290                 295                 300

Leu Cys Arg Phe Gly Phe Phe Gln Val Val Asn Asn Asn Tyr Asp Arg
305                 310                 315                 320

Trp Gly Thr Tyr Ala Ile Gly Gly Ser Ser Ala Pro Thr Ile Leu Cys
                325                 330                 335

Arg Phe Gly Phe Phe Gln Val Val Asn Asn Asn Tyr Asp Arg Trp Gly
            340                 345                 350

Thr Tyr Ala Ile Gly Gly Ser Ser Ala Pro Thr Ile Leu
            355                 360                 365
```

-continued

```
<210> SEQ ID NO 59
<211> LENGTH: 545
<212> TYPE: PRT
<213> ORGANISM: Artificial Sequence
<220> FEATURE:
<223> OTHER INFORMATION: K4

<400> SEQUENCE: 59
```

Cys Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu Cys Arg
            20                  25                  30

Phe Gly Phe Phe Gln Val Val Asn Asn Asn Tyr Asp Arg Trp Gly Thr
        35                  40                  45

Tyr Ala Ile Gly Gly Ser Ser Ala Pro Thr Ile Leu Ala Glu Gly Val
    50                  55                  60

Gly Glu Ile Leu Pro Ser Val Asn Glu Thr Arg Ser Leu Gln Ala Cys
65                  70                  75                  80

Glu Ala Tyr Asn Ile Ile Asp Lys Cys Ala Glu Gly Val Gly Glu Ile
                85                  90                  95

Leu Pro Ser Val Asn Glu Thr Arg Ser Leu Gln Ala Cys Glu Ala Tyr
            100                 105                 110

Asn Ile Ile Asp Lys Cys Ser Asp Pro Val Leu Thr Pro Val Gln Ser
        115                 120                 125

Ala Gly Met Ile Pro Ala Glu Pro Gly Glu Ala Ala Ile Lys Leu Thr
    130                 135                 140

Ser Ser Ala Gly Val Leu Ser Cys Ser Asp Pro Val Leu Thr Pro Val
145                 150                 155                 160

Gln Ser Ala Gly Met Ile Pro Ala Glu Pro Gly Glu Ala Ala Ile Lys
                165                 170                 175

Leu Thr Ser Ser Ala Gly Val Leu Ser Cys Gly Gly Trp Ser Ser Lys
            180                 185                 190

Pro Arg Lys Gly Met Gly Thr Asn Leu Ser Val Pro Asn Pro Leu Gly
        195                 200                 205

Phe Phe Pro Asp His Gln Leu Asp Pro Ala Phe Gly Ala Asn Ser Asn
    210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro His
                245                 250                 255

Gly Gly Ile Leu Gly Trp Ser Pro Gln Ala Gln Gly Ile Leu Thr Thr
            260                 265                 270

Val Ser Thr Ile Pro Pro Pro Ala Ser Thr Asn Arg Gln Ser Gly Arg
        275                 280                 285

Gln Pro Thr Pro Ile Ser Pro Pro Leu Arg Asp Ser His Pro Gln Ala
    290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg
            340                 345                 350

Thr Gly Asp Pro Val Thr Asn Ser Asp Pro Val Leu Thr Pro Val Gln
        355                 360                 365

```
Ser Ala Gly Met Ile Pro Ala Glu Pro Gly Glu Ala Ala Ile Lys Leu
        370                 375                 380

Thr Ser Ser Ala Gly Val Leu Ser Cys Ser Asp Pro Val Leu Thr Pro
385                 390                 395                 400

Val Gln Ser Ala Gly Met Ile Pro Ala Glu Pro Gly Glu Ala Ala Ile
            405                 410                 415

Lys Leu Thr Ser Ser Ala Gly Val Leu Ser Cys Ala Glu Gly Val Gly
                420                 425                 430

Glu Ile Leu Pro Ser Val Asn Glu Thr Arg Ser Leu Gln Ala Cys Glu
            435                 440                 445

Ala Tyr Asn Ile Ile Asp Lys Cys Ala Glu Gly Val Gly Glu Ile Leu
        450                 455                 460

Pro Ser Val Asn Glu Thr Arg Ser Leu Gln Ala Cys Glu Ala Tyr Asn
465                 470                 475                 480

Ile Ile Asp Lys Cys Cys Arg Phe Gly Phe Phe Gln Val Val Asn Asn
            485                 490                 495

Asn Tyr Asp Arg Trp Gly Thr Tyr Ala Ile Gly Gly Ser Ser Ala Pro
            500                 505                 510

Thr Ile Leu Cys Arg Phe Gly Phe Phe Gln Val Val Asn Asn Asn Tyr
            515                 520                 525

Asp Arg Trp Gly Thr Tyr Ala Ile Gly Gly Ser Ser Ala Pro Thr Ile
            530                 535                 540

Leu
545

<210> SEQ ID NO 60
<211> LENGTH: 529
<212> TYPE: PRT
<213> ORGANISM: Artificial Sequence
<220> FEATURE:
<223> OTHER INFORMATION: K5

<400> SEQUENCE: 60

Trp Arg Gly Lys Ala Asp Trp Glu Asn Asn Arg Gln Ala Leu Ala Asp
1               5                   10                  15

Cys Ala Gln Gly Phe Ala Lys Gly Thr Tyr Gly Gly Lys Trp Trp Arg
            20                  25                  30

Gly Lys Ala Asp Trp Glu Asn Asn Arg Gln Ala Leu Ala Asp Cys Ala
        35                  40                  45

Gln Gly Phe Ala Lys Gly Thr Tyr Gly Gly Lys Trp Ala Asp Asp Thr
50                  55                  60

His Val Gln Asp Lys Gly Met Leu Ala Thr Val Ala Phe Asn Met Phe
65                  70                  75                  80

Thr Asp Asn Val Asp Gln Arg Met Pro Arg Ala Asp Asp Thr His Val
            85                  90                  95

Gln Asp Lys Gly Met Leu Ala Thr Val Ala Phe Asn Met Phe Thr Asp
            100                 105                 110

Asn Val Asp Gln Arg Met Pro Arg Ala Glu Gly Val Gly Glu Ile Leu
            115                 120                 125

Pro Ser Val Asn Glu Thr Arg Ser Leu Gln Ala Cys Glu Ala Tyr Asn
130                 135                 140

Ile Ile Asp Lys Cys Ala Glu Gly Val Gly Glu Ile Leu Pro Ser Val
145                 150                 155                 160

Asn Glu Thr Arg Ser Leu Gln Ala Cys Glu Ala Tyr Asn Ile Ile Asp
            165                 170                 175
```

Lys Cys Gly Gly Trp Ser Ser Lys Pro Arg Lys Gly Met Gly Thr Asn
            180                 185                 190

Leu Ser Val Pro Asn Pro Leu Gly Phe Phe Pro Asp His Gln Leu Asp
        195                 200                 205

Pro Ala Phe Gly Ala Asn Ser Asn Asn Pro Asp Trp Asp Phe Asn Pro
210                 215                 220

Ile Lys Asp His Trp Pro Ala Ala Asn Gln Val Gly Val Gly Ala Phe
225                 230                 235                 240

Gly Pro Gly Leu Thr Pro Pro His Gly Gly Ile Leu Gly Trp Ser Pro
                245                 250                 255

Gln Ala Gln Gly Ile Leu Thr Thr Val Ser Thr Ile Pro Pro Pro Ala
            260                 265                 270

Ser Thr Asn Arg Gln Ser Gly Arg Gln Pro Thr Pro Ile Ser Pro Pro
        275                 280                 285

Leu Arg Asp Ser His Pro Gln Ala Met Gln Trp Asn Ser Thr Ala Phe
290                 295                 300

His Gln Ala Leu Gln Asp Pro Arg Val Arg Gly Leu Tyr Phe Pro Ala
305                 310                 315                 320

Gly Gly Ser Ser Ser Gly Thr Val Asn Pro Ala Pro Asn Ile Ala Ser
                325                 330                 335

His Ile Ser Ser Ile Ser Ala Arg Thr Gly Asp Pro Val Thr Asn Trp
            340                 345                 350

Arg Gly Lys Ala Asp Trp Glu Asn Asn Arg Gln Ala Leu Ala Asp Cys
        355                 360                 365

Ala Gln Gly Phe Ala Lys Gly Thr Tyr Gly Gly Lys Trp Trp Arg Gly
370                 375                 380

Lys Ala Asp Trp Glu Asn Asn Arg Gln Ala Leu Ala Asp Cys Ala Gln
385                 390                 395                 400

Gly Phe Ala Lys Gly Thr Tyr Gly Gly Lys Trp Ala Asp Asp Thr His
                405                 410                 415

Val Gln Asp Lys Gly Met Leu Ala Thr Val Ala Phe Asn Met Phe Thr
            420                 425                 430

Asp Asn Val Asp Gln Arg Met Pro Arg Ala Asp Thr His Val Gln
        435                 440                 445

Asp Lys Gly Met Leu Ala Thr Val Ala Phe Asn Met Phe Thr Asp Asn
450                 455                 460

Val Asp Gln Arg Met Pro Arg Ala Glu Gly Val Gly Glu Ile Leu Pro
465                 470                 475                 480

Ser Val Asn Glu Thr Arg Ser Leu Gln Ala Cys Glu Ala Tyr Asn Ile
                485                 490                 495

Ile Asp Lys Cys Ala Glu Gly Val Gly Glu Ile Leu Pro Ser Val Asn
            500                 505                 510

Glu Thr Arg Ser Leu Gln Ala Cys Glu Ala Tyr Asn Ile Ile Asp Lys
        515                 520                 525

Cys

<210> SEQ ID NO 61
<211> LENGTH: 632
<212> TYPE: PRT
<213> ORGANISM: Artificial Sequence
<220> FEATURE:
<223> OTHER INFORMATION: K6

<400> SEQUENCE: 61

-continued

```
Ala Asp Asp Thr His Val Gln Asp Lys Gly Met Leu Ala Thr Val Ala
1               5                   10                  15

Phe Asn Met Phe Thr Asp Asn Val Asp Gln Arg Met Pro Arg Ala Asp
            20                  25                  30

Asp Thr His Val Gln Asp Lys Gly Met Leu Ala Thr Val Ala Phe Asn
            35                  40                  45

Met Phe Thr Asp Asn Val Asp Gln Arg Met Pro Arg Ala Asp Asp Thr
        50                  55                  60

His Val Gln Asp Lys Gly Met Leu Ala Thr Val Ala Phe Asn Met Phe
65                  70                  75                  80

Thr Asp Asn Val Asp Gln Arg Met Pro Arg Ser Asp Pro Val Leu Thr
            85                  90                  95

Pro Val Gln Ser Ala Gly Met Ile Pro Ala Glu Pro Gly Glu Ala Ala
            100                 105                 110

Ile Lys Leu Thr Ser Ser Ala Gly Val Leu Ser Cys Ser Asp Pro Val
            115                 120                 125

Leu Thr Pro Val Gln Ser Ala Gly Met Ile Pro Ala Glu Pro Gly Glu
        130                 135                 140

Ala Ala Ile Lys Leu Thr Ser Ser Ala Gly Val Leu Ser Cys Ser Asp
145                 150                 155                 160

Pro Val Leu Thr Pro Val Gln Ser Ala Gly Met Ile Pro Ala Glu Pro
            165                 170                 175

Gly Glu Ala Ala Ile Lys Leu Thr Ser Ser Ala Gly Val Leu Ser Cys
            180                 185                 190

Gly Gly Trp Ser Ser Lys Pro Arg Lys Gly Met Gly Thr Asn Leu Ser
            195                 200                 205

Val Pro Asn Pro Leu Gly Phe Phe Pro Asp His Gln Leu Asp Pro Ala
        210                 215                 220

Phe Gly Ala Asn Ser Asn Pro Asp Trp Asp Phe Asn Pro Ile Lys
225                 230                 235                 240

Asp His Trp Pro Ala Ala Asn Gln Val Gly Val Gly Ala Phe Gly Pro
            245                 250                 255

Gly Leu Thr Pro Pro His Gly Gly Ile Leu Gly Trp Ser Pro Gln Ala
            260                 265                 270

Gln Gly Ile Leu Thr Thr Val Ser Thr Ile Pro Pro Ala Ser Thr
        275                 280                 285

Asn Arg Gln Ser Gly Arg Gln Pro Thr Pro Ile Ser Pro Pro Leu Arg
        290                 295                 300

Asp Ser His Pro Gln Ala Met Gln Trp Asn Ser Thr Ala Phe His Gln
305                 310                 315                 320

Ala Leu Gln Asp Pro Arg Val Arg Gly Leu Tyr Phe Pro Ala Gly Gly
            325                 330                 335

Ser Ser Ser Gly Thr Val Asn Pro Ala Pro Asn Ile Ala Ser His Ile
            340                 345                 350

Ser Ser Ile Ser Ala Arg Thr Gly Asp Pro Val Thr Asn Ala Glu Gly
            355                 360                 365

Val Gly Glu Ile Leu Pro Ser Val Asn Glu Thr Arg Ser Leu Gln Ala
            370                 375                 380

Cys Glu Ala Tyr Asn Ile Ile Asp Lys Cys Ala Glu Gly Val Gly Glu
385                 390                 395                 400

Ile Leu Pro Ser Val Asn Glu Thr Arg Ser Leu Gln Ala Cys Glu Ala
            405                 410                 415

Tyr Asn Ile Ile Asp Lys Cys Ala Glu Gly Val Gly Glu Ile Leu Pro
```

```
                420           425           430
Ser Val Asn Glu Thr Arg Ser Leu Gln Ala Cys Glu Ala Tyr Asn Ile
            435                 440                 445

Ile Asp Lys Cys Cys Arg Phe Gly Phe Phe Gln Val Asn Asn Asn
        450                 455                 460

Tyr Asp Arg Trp Gly Thr Tyr Ala Ile Gly Gly Ser Ser Ala Pro Thr
465                 470                 475                 480

Ile Leu Cys Arg Phe Gly Phe Phe Gln Val Val Asn Asn Asn Tyr Asp
                    485                 490                 495

Arg Trp Gly Thr Tyr Ala Ile Gly Gly Ser Ser Ala Pro Thr Ile Leu
                500                 505                 510

Cys Arg Phe Gly Phe Phe Gln Val Val Asn Asn Asn Tyr Asp Arg Trp
            515                 520                 525

Gly Thr Tyr Ala Ile Gly Gly Ser Ser Ala Pro Thr Ile Leu Trp Arg
        530                 535                 540

Gly Lys Ala Asp Trp Glu Asn Asn Arg Gln Ala Leu Ala Asp Cys Ala
545                 550                 555                 560

Gln Gly Phe Ala Lys Gly Thr Tyr Gly Gly Lys Trp Arg Gly Lys
                    565                 570                 575

Ala Asp Trp Glu Asn Asn Arg Gln Ala Leu Ala Asp Cys Ala Gln Gly
                580                 585                 590

Phe Ala Lys Gly Thr Tyr Gly Gly Lys Trp Arg Gly Lys Ala Asp
            595                 600                 605

Trp Glu Asn Asn Arg Gln Ala Leu Ala Asp Cys Ala Gln Gly Phe Ala
        610                 615                 620

Lys Gly Thr Tyr Gly Gly Lys Trp
625                 630

<210> SEQ ID NO 62
<211> LENGTH: 533
<212> TYPE: PRT
<213> ORGANISM: Artificial Sequence
<220> FEATURE:
<223> OTHER INFORMATION: K4A

<400> SEQUENCE: 62

Arg Phe Gly Phe Phe Gln Val Val Asn Asn Asn Tyr Asp Arg Trp Gly
1               5                   10                  15

Thr Tyr Ala Ile Gly Gly Ser Ser Ala Pro Thr Ile Leu Arg Phe Gly
            20                  25                  30

Phe Phe Gln Val Val Asn Asn Asn Tyr Asp Arg Trp Gly Thr Tyr Ala
        35                  40                  45

Ile Gly Gly Ser Ser Ala Pro Thr Ile Leu Ala Glu Gly Val Gly Glu
    50                  55                  60

Ile Leu Pro Ser Val Asn Glu Thr Arg Ser Leu Gln Ala Cys Glu Ala
65                  70                  75                  80

Tyr Asn Ile Ile Asp Lys Ala Glu Gly Val Gly Glu Ile Leu Pro Ser
                85                  90                  95

Val Asn Glu Thr Arg Ser Leu Gln Ala Cys Glu Ala Tyr Asn Ile Ile
            100                 105                 110

Asp Lys Ser Asp Pro Val Leu Thr Pro Val Gln Ser Ala Gly Met Ile
        115                 120                 125

Pro Ala Glu Pro Gly Glu Ala Ala Ile Lys Leu Thr Ser Ser Ala Gly
    130                 135                 140

Val Leu Ser Ser Asp Pro Val Leu Thr Pro Val Gln Ser Ala Gly Met
```

145                 150                 155                 160
    Ile Pro Ala Glu Pro Gly Glu Ala Ala Ile Lys Leu Thr Ser Ser Ala
                    165                 170                 175
    Gly Val Leu Ser Gly Gly Trp Ser Ser Lys Pro Arg Lys Gly Met Gly
                    180                 185                 190
    Thr Asn Leu Ser Val Pro Asn Pro Leu Gly Phe Phe Pro Asp His Gln
                    195                 200                 205
    Leu Asp Pro Ala Phe Gly Ala Asn Ser Asn Pro Asp Trp Asp Phe
    210                 215                 220
    Asn Pro Ile Lys Asp His Trp Pro Ala Asn Gln Val Gly Val Gly
    225                 230                 235                 240
    Ala Phe Gly Pro Gly Leu Thr Pro Pro His Gly Gly Ile Leu Gly Trp
                    245                 250                 255
    Ser Pro Gln Ala Gln Gly Ile Leu Thr Thr Val Ser Thr Ile Pro Pro
                    260                 265                 270
    Pro Ala Ser Thr Asn Arg Gln Ser Gly Arg Gln Pro Thr Pro Ile Ser
                    275                 280                 285
    Pro Pro Leu Arg Asp Ser His Pro Gln Ala Met Gln Trp Asn Ser Thr
    290                 295                 300
    Ala Phe His Gln Ala Leu Gln Asp Pro Arg Val Arg Gly Leu Tyr Phe
    305                 310                 315                 320
    Pro Ala Gly Gly Ser Ser Ser Gly Thr Val Asn Pro Ala Pro Asn Ile
                    325                 330                 335
    Ala Ser His Ile Ser Ser Ile Ser Ala Arg Thr Gly Asp Pro Val Thr
                    340                 345                 350
    Asn Ser Asp Pro Val Leu Thr Pro Val Gln Ser Ala Gly Met Ile Pro
                    355                 360                 365
    Ala Glu Pro Gly Glu Ala Ala Ile Lys Leu Thr Ser Ser Ala Gly Val
                    370                 375                 380
    Leu Ser Ser Asp Pro Val Leu Thr Pro Val Gln Ser Ala Gly Met Ile
    385                 390                 395                 400
    Pro Ala Glu Pro Gly Glu Ala Ala Ile Lys Leu Thr Ser Ser Ala Gly
                    405                 410                 415
    Val Leu Ser Ala Glu Gly Val Gly Glu Ile Leu Pro Ser Val Asn Glu
                    420                 425                 430
    Thr Arg Ser Leu Gln Ala Cys Glu Ala Tyr Asn Ile Ile Asp Lys Ala
                    435                 440                 445
    Glu Gly Val Gly Glu Ile Leu Pro Ser Val Asn Glu Thr Arg Ser Leu
                    450                 455                 460
    Gln Ala Cys Glu Ala Tyr Asn Ile Ile Asp Lys Arg Phe Gly Phe Phe
    465                 470                 475                 480
    Gln Val Val Asn Asn Asn Tyr Asp Arg Trp Gly Thr Tyr Ala Ile Gly
                    485                 490                 495
    Gly Ser Ser Ala Pro Thr Ile Leu Arg Phe Gly Phe Phe Gln Val Val
                    500                 505                 510
    Asn Asn Asn Tyr Asp Arg Trp Gly Thr Tyr Ala Ile Gly Gly Ser Ser
                    515                 520                 525
    Ala Pro Thr Ile Leu
            530

<210> SEQ ID NO 63
<211> LENGTH: 545
<212> TYPE: PRT
<213> ORGANISM: Artificial Sequence

<220> FEATURE:
<223> OTHER INFORMATION: K4B

<400> SEQUENCE: 63

```
Ser Arg Phe Gly Phe Phe Gln Val Val Asn Asn Asn Tyr Asp Arg Trp
1               5                   10                  15

Gly Thr Tyr Ala Ile Gly Gly Ser Ser Ala Pro Thr Ile Leu Ser Arg
                20                  25                  30

Phe Gly Phe Phe Gln Val Val Asn Asn Asn Tyr Asp Arg Trp Gly Thr
            35                  40                  45

Tyr Ala Ile Gly Gly Ser Ser Ala Pro Thr Ile Leu Ala Glu Gly Val
        50                  55                  60

Gly Glu Ile Leu Pro Ser Val Asn Glu Thr Arg Ser Leu Gln Ala Ser
65                  70                  75                  80

Glu Ala Tyr Asn Ile Ile Asp Lys Ser Ala Glu Gly Val Gly Glu Ile
                85                  90                  95

Leu Pro Ser Val Asn Glu Thr Arg Ser Leu Gln Ala Ser Glu Ala Tyr
                100                 105                 110

Asn Ile Ile Asp Lys Ser Ser Asp Pro Val Leu Thr Pro Val Gln Ser
            115                 120                 125

Ala Gly Met Ile Pro Ala Glu Pro Gly Glu Ala Ala Ile Lys Leu Thr
        130                 135                 140

Ser Ser Ala Gly Val Leu Ser Ser Ser Asp Pro Val Leu Thr Pro Val
145                 150                 155                 160

Gln Ser Ala Gly Met Ile Pro Ala Glu Pro Gly Glu Ala Ala Ile Lys
                165                 170                 175

Leu Thr Ser Ser Ala Gly Val Leu Ser Ser Gly Gly Trp Ser Ser Lys
                180                 185                 190

Pro Arg Lys Gly Met Gly Thr Asn Leu Ser Val Pro Asn Pro Leu Gly
            195                 200                 205

Phe Phe Pro Asp His Gln Leu Asp Pro Ala Phe Gly Ala Asn Ser Asn
        210                 215                 220

Asn Pro Asp Trp Asp Phe Asn Pro Ile Lys Asp His Trp Pro Ala Ala
225                 230                 235                 240

Asn Gln Val Gly Val Gly Ala Phe Gly Pro Gly Leu Thr Pro Pro His
                245                 250                 255

Gly Gly Ile Leu Gly Trp Ser Pro Gln Ala Gln Gly Ile Leu Thr Thr
                260                 265                 270

Val Ser Thr Ile Pro Pro Pro Ala Ser Thr Asn Arg Gln Ser Gly Arg
            275                 280                 285

Gln Pro Thr Pro Ile Ser Pro Pro Leu Arg Asp Ser His Pro Gln Ala
        290                 295                 300

Met Gln Trp Asn Ser Thr Ala Phe His Gln Ala Leu Gln Asp Pro Arg
305                 310                 315                 320

Val Arg Gly Leu Tyr Phe Pro Ala Gly Gly Ser Ser Ser Gly Thr Val
                325                 330                 335

Asn Pro Ala Pro Asn Ile Ala Ser His Ile Ser Ser Ile Ser Ala Arg
                340                 345                 350

Thr Gly Asp Pro Val Thr Asn Ser Asp Pro Val Leu Thr Pro Val Gln
            355                 360                 365

Ser Ala Gly Met Ile Pro Ala Glu Pro Gly Glu Ala Ala Ile Lys Leu
        370                 375                 380

Thr Ser Ser Ala Gly Val Leu Ser Ser Asp Pro Val Leu Thr Pro
385                 390                 395                 400
```

```
Val Gln Ser Ala Gly Met Ile Pro Ala Glu Pro Gly Glu Ala Ala Ile
                405                 410                 415

Lys Leu Thr Ser Ser Ala Gly Val Leu Ser Ser Ala Glu Gly Val Gly
                420                 425                 430

Glu Ile Leu Pro Ser Val Asn Glu Thr Arg Ser Leu Gln Ala Ser Glu
                435                 440                 445

Ala Tyr Asn Ile Ile Asp Lys Ser Ala Glu Gly Val Gly Glu Ile Leu
            450                 455                 460

Pro Ser Val Asn Glu Thr Arg Ser Leu Gln Ala Ser Glu Ala Tyr Asn
465                 470                 475                 480

Ile Ile Asp Lys Ser Ser Arg Phe Gly Phe Phe Gln Val Val Asn Asn
                485                 490                 495

Asn Tyr Asp Arg Trp Gly Thr Tyr Ala Ile Gly Gly Ser Ser Ala Pro
                500                 505                 510

Thr Ile Leu Ser Arg Phe Gly Phe Phe Gln Val Val Asn Asn Asn Tyr
                515                 520                 525

Asp Arg Trp Gly Thr Tyr Ala Ile Gly Gly Ser Ser Ala Pro Thr Ile
            530                 535                 540

Leu
545

<210> SEQ ID NO 64
<211> LENGTH: 541
<212> TYPE: PRT
<213> ORGANISM: Artificial Sequence
<220> FEATURE:
<223> OTHER INFORMATION: K4C

<400> SEQUENCE: 64

Cys Arg His Gly Phe Phe Gln Val Val Asn Asn Tyr Asp Lys Trp
1               5                   10                  15

Gly Ser Tyr Ala Ile Gly Gly Ser Ala Ser Pro Thr Ile Leu Cys Arg
                20                  25                  30

His Gly Phe Phe Gln Val Val Asn Asn Asn Tyr Asp Lys Trp Gly Ser
            35                  40                  45

Tyr Ala Ile Gly Gly Ser Ala Ser Pro Thr Ile Leu Ala Glu Asp Leu
        50                  55                  60

Gln Glu Ile Leu Pro Val Asn Glu Thr Arg Arg Leu Thr Thr Ser Gly
65                  70                  75                  80

Ala Tyr Asn Ile Ile Asp Gly Cys Ala Glu Asp Leu Gln Glu Ile Leu
                85                  90                  95

Pro Val Asn Glu Thr Arg Arg Leu Thr Thr Ser Gly Ala Tyr Asn Ile
                100                 105                 110

Ile Asp Gly Cys Val Asp Pro Val Leu Thr Pro Glu Gln Ser Ala Gly
            115                 120                 125

Met Ile Pro Ala Glu Pro Gly Glu Ser Ala Leu Ser Leu Thr Ser Ser
130                 135                 140

Ala Gly Val Leu Ser Cys Val Asp Pro Val Leu Thr Pro Glu Gln Ser
145                 150                 155                 160

Ala Gly Met Ile Pro Ala Glu Pro Gly Glu Ser Ala Leu Ser Leu Thr
                165                 170                 175

Ser Ser Ala Gly Val Leu Ser Cys Gly Gly Trp Ser Ser Lys Pro Arg
            180                 185                 190

Lys Gly Met Gly Thr Asn Leu Ser Val Pro Asn Pro Leu Gly Phe Phe
        195                 200                 205
```

```
Pro Asp His Gln Leu Asp Pro Ala Phe Gly Ala Asn Ser Asn Asn Pro
    210                 215                 220

Asp Trp Asp Phe Asn Pro Ile Lys Asp His Trp Pro Ala Ala Asn Gln
225                 230                 235                 240

Val Gly Val Gly Ala Phe Gly Pro Gly Leu Thr Pro Pro His Gly Gly
                245                 250                 255

Ile Leu Gly Trp Ser Pro Gln Ala Gln Gly Ile Leu Thr Thr Val Ser
            260                 265                 270

Thr Ile Pro Pro Pro Ala Ser Thr Asn Arg Gln Ser Gly Arg Gln Pro
        275                 280                 285

Thr Pro Ile Ser Pro Pro Leu Arg Asp Ser His Pro Gln Ala Met Gln
    290                 295                 300

Trp Asn Ser Thr Ala Phe His Gln Ala Leu Gln Asp Pro Arg Val Arg
305                 310                 315                 320

Gly Leu Tyr Phe Pro Ala Gly Gly Ser Ser Gly Thr Val Asn Pro
                325                 330                 335

Ala Pro Asn Ile Ala Ser His Ile Ser Ser Ile Ser Ala Arg Thr Gly
            340                 345                 350

Asp Pro Val Thr Asn Val Asp Pro Val Leu Thr Pro Glu Gln Ser Ala
        355                 360                 365

Gly Met Ile Pro Ala Glu Pro Gly Glu Ser Ala Leu Ser Leu Thr Ser
    370                 375                 380

Ser Ala Gly Val Leu Ser Cys Val Asp Pro Val Leu Thr Pro Glu Gln
385                 390                 395                 400

Ser Ala Gly Met Ile Pro Ala Glu Pro Gly Glu Ser Ala Leu Ser Leu
                405                 410                 415

Thr Ser Ser Ala Gly Val Leu Ser Cys Ala Glu Asp Leu Gln Glu Ile
            420                 425                 430

Leu Pro Val Asn Glu Thr Arg Arg Leu Thr Thr Ser Gly Ala Tyr Asn
        435                 440                 445

Ile Ile Asp Gly Cys Ala Glu Asp Leu Gln Glu Ile Leu Pro Val Asn
    450                 455                 460

Glu Thr Arg Arg Leu Thr Thr Ser Gly Ala Tyr Asn Ile Ile Asp Gly
465                 470                 475                 480

Cys Cys Arg His Gly Phe Phe Gln Val Val Asn Asn Tyr Asp Lys
                485                 490                 495

Trp Gly Ser Tyr Ala Ile Gly Gly Ser Ala Ser Pro Thr Ile Leu Cys
            500                 505                 510

Arg His Gly Phe Phe Gln Val Val Asn Asn Asn Tyr Asp Lys Trp Gly
        515                 520                 525

Ser Tyr Ala Ile Gly Gly Ser Ala Ser Pro Thr Ile Leu
    530                 535                 540

<210> SEQ ID NO 65
<211> LENGTH: 543
<212> TYPE: PRT
<213> ORGANISM: Artificial Sequence
<220> FEATURE:
<223> OTHER INFORMATION: K4D

<400> SEQUENCE: 65

Cys Arg His Gly Phe Phe Gln Val Val Asn Asn Asn Tyr Asp Lys Trp
1               5                   10                  15

Gly Ser Tyr Ala Ile Gly Gly Ser Ala Ser Pro Thr Ile Leu Cys Arg
            20                  25                  30
```

-continued

His Gly Phe Phe Gln Val Val Asn Asn Asn Tyr Asp Lys Trp Gly Ser
                35                  40                  45

Tyr Ala Ile Gly Gly Ser Ala Ser Pro Thr Ile Leu Ala Glu Asp Leu
 50                  55                  60

Gln Glu Ile Leu Pro Val Asn Glu Thr Arg Arg Leu Thr Thr Ser Gly
 65                  70                  75                  80

Ala Tyr Asn Ile Ile Asp Gly Cys Ala Glu Asp Leu Gln Glu Ile Leu
                85                  90                  95

Pro Val Asn Glu Thr Arg Arg Leu Thr Thr Ser Gly Ala Tyr Asn Ile
                100                 105                 110

Ile Asp Gly Cys Val Asp Pro Val Leu Thr Pro Glu Gln Ser Ala Gly
                115                 120                 125

Met Ile Pro Ala Glu Pro Gly Glu Ser Ala Leu Ser Leu Thr Ser Ser
130                 135                 140

Ala Gly Val Leu Ser Cys Val Asp Pro Val Leu Thr Pro Glu Gln Ser
145                 150                 155                 160

Ala Gly Met Ile Pro Ala Glu Pro Gly Glu Ser Ala Leu Ser Leu Thr
                165                 170                 175

Ser Ser Ala Gly Val Leu Ser Cys Gly Gly Trp Ser Ser Lys Pro Arg
                180                 185                 190

Lys Gly Met Gly Thr Asn Leu Ser Val Pro Asn Pro Leu Gly Phe Phe
                195                 200                 205

Pro Asp His Gln Leu Asp Pro Ala Phe Gly Ala Asn Ser Asn Asn Pro
                210                 215                 220

Asp Trp Asp Phe Asn Pro Ile Lys Asp His Trp Pro Ala Ala Asn Gln
225                 230                 235                 240

Val Gly Val Gly Ala Phe Gly Pro Gly Leu Thr Pro Pro His Gly Gly
                245                 250                 255

Ile Leu Gly Trp Ser Pro Gln Ala Gln Gly Ile Leu Thr Thr Val Ser
                260                 265                 270

Thr Ile Pro Pro Pro Ala Ser Thr Asn Arg Gln Ser Gly Arg Gln Pro
                275                 280                 285

Thr Pro Ile Ser Pro Pro Leu Arg Asp Ser His Pro Gln Ala Met Gln
                290                 295                 300

Trp Asn Ser Thr Ala Phe His Gln Ala Leu Gln Asp Pro Arg Val Arg
305                 310                 315                 320

Gly Leu Tyr Phe Pro Ala Gly Gly Ser Ser Ser Gly Thr Val Asn Pro
                325                 330                 335

Ala Pro Asn Ile Ala Ser His Ile Ser Ser Ile Ser Ala Arg Thr Gly
                340                 345                 350

Asp Pro Val Thr Asn Ser Asp Pro Val Leu Thr Pro Val Gln Ser Ala
                355                 360                 365

Gly Met Ile Pro Ala Glu Pro Gly Glu Ala Ala Ile Lys Leu Thr Ser
370                 375                 380

Ser Ala Gly Val Leu Ser Cys Ser Asp Pro Val Leu Thr Pro Val Gln
385                 390                 395                 400

Ser Ala Gly Met Ile Pro Ala Glu Pro Gly Glu Ala Ala Ile Lys Leu
                405                 410                 415

Thr Ser Ser Ala Gly Val Leu Ser Cys Ala Glu Gly Val Gly Glu Ile
                420                 425                 430

Leu Pro Ser Val Asn Glu Thr Arg Ser Leu Gln Ala Cys Glu Ala Tyr
                435                 440                 445

-continued

```
Asn Ile Ile Asp Lys Cys Ala Glu Gly Val Gly Glu Ile Leu Pro Ser
        450                 455                 460
Val Asn Glu Thr Arg Ser Leu Gln Ala Cys Glu Ala Tyr Asn Ile Ile
465                 470                 475                 480
Asp Lys Cys Cys Arg Phe Gly Phe Phe Gln Val Val Asn Asn Asn Tyr
                485                 490                 495
Asp Arg Trp Gly Thr Tyr Ala Ile Gly Gly Ser Ser Ala Pro Thr Ile
            500                 505                 510
Leu Cys Arg Phe Gly Phe Phe Gln Val Val Asn Asn Asn Tyr Asp Arg
        515                 520                 525
Trp Gly Thr Tyr Ala Ile Gly Gly Ser Ser Ala Pro Thr Ile Leu
    530                 535                 540

<210> SEQ ID NO 66
<211> LENGTH: 543
<212> TYPE: PRT
<213> ORGANISM: Artificial Sequence
<220> FEATURE:
<223> OTHER INFORMATION: K4E

<400> SEQUENCE: 66

Cys Arg His Gly Phe Phe Gln Val Val Asn Asn Asn Tyr Asp Lys Trp
1               5                   10                  15
Gly Ser Tyr Ala Ile Gly Gly Ser Ala Ser Pro Thr Ile Leu Cys Arg
            20                  25                  30
Phe Gly Phe Phe Gln Val Val Asn Asn Asn Tyr Asp Arg Trp Gly Thr
        35                  40                  45
Tyr Ala Ile Gly Gly Ser Ser Ala Pro Thr Ile Leu Ala Glu Asp Leu
    50                  55                  60
Gln Glu Ile Leu Pro Val Asn Glu Thr Arg Arg Leu Thr Thr Ser Gly
65                  70                  75                  80
Ala Tyr Asn Ile Ile Asp Gly Cys Ala Glu Gly Val Gly Glu Ile Leu
                85                  90                  95
Pro Ser Val Asn Glu Thr Arg Ser Leu Gln Ala Cys Glu Ala Tyr Asn
            100                 105                 110
Ile Ile Asp Lys Cys Val Asp Pro Val Leu Thr Pro Glu Gln Ser Ala
        115                 120                 125
Gly Met Ile Pro Ala Glu Pro Gly Glu Ser Ala Leu Ser Leu Thr Ser
    130                 135                 140
Ser Ala Gly Val Leu Ser Cys Ser Asp Pro Val Leu Thr Pro Val Gln
145                 150                 155                 160
Ser Ala Gly Met Ile Pro Ala Glu Pro Gly Glu Ala Ala Ile Lys Leu
                165                 170                 175
Thr Ser Ser Ala Gly Val Leu Ser Cys Gly Gly Trp Ser Ser Lys Pro
            180                 185                 190
Arg Lys Gly Met Gly Thr Asn Leu Ser Val Pro Asn Pro Leu Gly Phe
        195                 200                 205
Phe Pro Asp His Gln Leu Asp Pro Ala Phe Gly Ala Asn Ser Asn Asn
    210                 215                 220
Pro Asp Trp Asp Phe Asn Pro Ile Lys Asp His Trp Pro Ala Ala Asn
225                 230                 235                 240
Gln Val Gly Val Gly Ala Phe Gly Pro Gly Leu Thr Pro Pro His Gly
                245                 250                 255
Gly Ile Leu Gly Trp Ser Pro Gln Ala Gln Gly Ile Leu Thr Thr Val
            260                 265                 270
```

Ser Thr Ile Pro Pro Ala Ser Thr Asn Arg Gln Ser Gly Arg Gln
            275                 280                 285

Pro Thr Pro Ile Ser Pro Leu Arg Asp Ser His Pro Gln Ala Met
290                 295                 300

Gln Trp Asn Ser Thr Ala Phe His Gln Ala Leu Gln Asp Pro Arg Val
305                 310                 315                 320

Arg Gly Leu Tyr Phe Pro Ala Gly Gly Ser Ser Gly Thr Val Asn
            325                 330                 335

Pro Ala Pro Asn Ile Ala Ser His Ile Ser Ser Ile Ser Ala Arg Thr
            340                 345                 350

Gly Asp Pro Val Thr Asn Val Asp Pro Val Leu Thr Pro Glu Gln Ser
            355                 360                 365

Ala Gly Met Ile Pro Ala Glu Pro Gly Glu Ser Ala Leu Ser Leu Thr
370                 375                 380

Ser Ser Ala Gly Val Leu Ser Cys Ser Asp Pro Val Leu Thr Pro Val
385                 390                 395                 400

Gln Ser Ala Gly Met Ile Pro Ala Glu Pro Gly Glu Ala Ala Ile Lys
            405                 410                 415

Leu Thr Ser Ser Ala Gly Val Leu Ser Cys Ala Glu Asp Leu Gln Glu
            420                 425                 430

Ile Leu Pro Val Asn Glu Thr Arg Arg Leu Thr Thr Ser Gly Ala Tyr
            435                 440                 445

Asn Ile Ile Asp Gly Cys Ala Glu Gly Val Gly Glu Ile Leu Pro Ser
            450                 455                 460

Val Asn Glu Thr Arg Ser Leu Gln Ala Cys Glu Ala Tyr Asn Ile Ile
465                 470                 475                 480

Asp Lys Cys Cys Arg His Gly Phe Phe Gln Val Val Asn Asn Asn Tyr
            485                 490                 495

Asp Lys Trp Gly Ser Tyr Ala Ile Gly Gly Ser Ala Ser Pro Thr Ile
            500                 505                 510

Leu Cys Arg Phe Gly Phe Gln Val Val Asn Asn Tyr Asp Arg
            515                 520                 525

Trp Gly Thr Tyr Ala Ile Gly Gly Ser Ser Ala Pro Thr Ile Leu
            530                 535                 540

<210> SEQ ID NO 67
<211> LENGTH: 597
<212> TYPE: PRT
<213> ORGANISM: Artificial Sequence
<220> FEATURE:
<223> OTHER INFORMATION: K4S

<400> SEQUENCE: 67

Ala Glu Asp Leu Gln Glu Ile Leu Pro Val Asn Glu Thr Arg Arg Leu
1               5                   10                  15

Thr Thr Ser Gly Ala Tyr Asn Ile Ile Asp Gly Cys Cys Arg His Gly
            20                  25                  30

Phe Phe Gln Val Val Asn Asn Tyr Asp Lys Trp Gly Ser Tyr Ala
        35                  40                  45

Ile Gly Gly Ser Ala Ser Pro Thr Ile Leu Cys Arg His Gly Phe Phe
    50                  55                  60

Gln Val Val Asn Asn Asn Tyr Asp Lys Trp Gly Ser Tyr Ala Ile Gly
65                  70                  75                  80

Gly Ser Ala Ser Pro Thr Ile Leu Ala Glu Asp Leu Gln Glu Ile Leu
            85                  90                  95

```
Pro Val Asn Glu Thr Arg Arg Leu Thr Thr Ser Gly Ala Tyr Asn Ile
            100                 105                 110

Ile Asp Gly Cys Ala Glu Asp Leu Gln Glu Ile Leu Pro Val Asn Glu
            115                 120                 125

Thr Arg Arg Leu Thr Thr Ser Gly Ala Tyr Asn Ile Ile Asp Gly Cys
            130                 135                 140

Val Asp Pro Val Leu Thr Pro Glu Gln Ser Ala Gly Met Ile Pro Ala
145                 150                 155                 160

Glu Pro Gly Glu Ser Ala Leu Ser Leu Thr Ser Ser Ala Gly Val Leu
            165                 170                 175

Ser Cys Val Asp Pro Val Leu Thr Pro Glu Gln Ser Ala Gly Met Ile
            180                 185                 190

Pro Ala Glu Pro Gly Glu Ser Ala Leu Ser Leu Thr Ser Ser Ala Gly
            195                 200                 205

Val Leu Ser Cys Gly Gly Trp Ser Ser Lys Pro Arg Lys Gly Met Gly
            210                 215                 220

Thr Asn Leu Ser Val Pro Asn Pro Leu Gly Phe Phe Pro Asp His Gln
225                 230                 235                 240

Leu Asp Pro Ala Phe Gly Ala Asn Ser Asn Asn Pro Asp Trp Asp Phe
            245                 250                 255

Asn Pro Ile Lys Asp His Trp Pro Ala Ala Asn Gln Val Gly Val Gly
            260                 265                 270

Ala Phe Gly Pro Gly Leu Thr Pro Pro His Gly Gly Ile Leu Gly Trp
            275                 280                 285

Ser Pro Gln Ala Gln Gly Ile Leu Thr Thr Val Ser Thr Ile Pro Pro
            290                 295                 300

Pro Ala Ser Thr Asn Arg Gln Ser Gly Arg Gln Pro Thr Pro Ile Ser
305                 310                 315                 320

Pro Pro Leu Arg Asp Ser His Pro Gln Ala Met Gln Trp Asn Ser Thr
            325                 330                 335

Ala Phe His Gln Ala Leu Gln Asp Pro Arg Val Arg Gly Leu Tyr Phe
            340                 345                 350

Pro Ala Gly Gly Ser Ser Ser Gly Thr Val Asn Pro Ala Pro Asn Ile
            355                 360                 365

Ala Ser His Ile Ser Ser Ile Ser Ala Arg Thr Gly Asp Pro Val Thr
            370                 375                 380

Asn Val Asp Pro Val Leu Thr Pro Glu Gln Ser Ala Gly Met Ile Pro
385                 390                 395                 400

Ala Glu Pro Gly Glu Ser Ala Leu Ser Leu Thr Ser Ser Ala Gly Val
            405                 410                 415

Leu Ser Cys Val Asp Pro Val Leu Thr Pro Glu Gln Ser Ala Gly Met
            420                 425                 430

Ile Pro Ala Glu Pro Gly Glu Ser Ala Leu Ser Leu Thr Ser Ser Ala
            435                 440                 445

Gly Val Leu Ser Cys Ala Glu Asp Leu Gln Glu Ile Leu Pro Val Asn
            450                 455                 460

Glu Thr Arg Arg Leu Thr Thr Ser Gly Ala Tyr Asn Ile Ile Asp Gly
465                 470                 475                 480

Cys Ala Glu Asp Leu Gln Glu Ile Leu Pro Val Asn Glu Thr Arg Arg
            485                 490                 495

Leu Thr Thr Ser Gly Ala Tyr Asn Ile Ile Asp Gly Cys Cys Arg His
            500                 505                 510

Gly Phe Phe Gln Val Val Asn Asn Asn Tyr Asp Lys Trp Gly Ser Tyr
```

```
                515                 520                 525
Ala Ile Gly Gly Ser Ala Ser Pro Thr Ile Leu Cys Arg His Gly Phe
            530                 535                 540

Phe Gln Val Val Asn Asn Asn Tyr Asp Lys Trp Gly Ser Tyr Ala Ile
545                 550                 555                 560

Gly Gly Ser Ala Ser Pro Thr Ile Leu Ala Glu Asp Leu Gln Glu Ile
                565                 570                 575

Leu Pro Val Asn Glu Thr Arg Arg Leu Thr Thr Ser Gly Ala Tyr Asn
            580                 585                 590

Ile Ile Asp Gly Cys
            595

<210> SEQ ID NO 68
<211> LENGTH: 603
<212> TYPE: PRT
<213> ORGANISM: Artificial Sequence
<220> FEATURE:
<223> OTHER INFORMATION: K4SHis

<400> SEQUENCE: 68

Ala Glu Asp Leu Gln Glu Ile Leu Pro Val Asn Glu Thr Arg Arg Leu
1               5                   10                  15

Thr Thr Ser Gly Ala Tyr Asn Ile Ile Asp Gly Cys Arg His Gly
            20                  25                  30

Phe Phe Gln Val Val Asn Asn Asn Tyr Asp Lys Trp Gly Ser Tyr Ala
            35                  40                  45

Ile Gly Gly Ser Ala Ser Pro Thr Ile Leu Cys Arg His Gly Phe Phe
    50                  55                  60

Gln Val Val Asn Asn Asn Tyr Asp Lys Trp Gly Ser Tyr Ala Ile Gly
65              70                  75                  80

Gly Ser Ala Ser Pro Thr Ile Leu Ala Glu Asp Leu Gln Glu Ile Leu
            85                  90                  95

Pro Val Asn Glu Thr Arg Arg Leu Thr Thr Ser Gly Ala Tyr Asn Ile
                100                 105                 110

Ile Asp Gly Cys Ala Glu Asp Leu Gln Glu Ile Leu Pro Val Asn Glu
            115                 120                 125

Thr Arg Arg Leu Thr Thr Ser Gly Ala Tyr Asn Ile Ile Asp Gly Cys
            130                 135                 140

Val Asp Pro Val Leu Thr Pro Glu Gln Ser Ala Gly Met Ile Pro Ala
145                 150                 155                 160

Glu Pro Gly Glu Ser Ala Leu Ser Leu Thr Ser Ser Ala Gly Val Leu
                165                 170                 175

Ser Cys Val Asp Pro Val Leu Thr Pro Glu Gln Ser Ala Gly Met Ile
            180                 185                 190

Pro Ala Glu Pro Gly Glu Ser Ala Leu Ser Leu Thr Ser Ser Ala Gly
            195                 200                 205

Val Leu Ser Cys Gly Gly Trp Ser Ser Lys Pro Arg Lys Gly Met Gly
            210                 215                 220

Thr Asn Leu Ser Val Pro Asn Pro Leu Gly Phe Phe Pro Asp His Gln
225                 230                 235                 240

Leu Asp Pro Ala Phe Gly Ala Asn Ser Asn Asn Pro Asp Trp Asp Phe
                245                 250                 255

Asn Pro Ile Lys Asp His Trp Pro Ala Ala Asn Gln Val Gly Val Gly
            260                 265                 270

Ala Phe Gly Pro Gly Leu Thr Pro Pro His Gly Gly Ile Leu Gly Trp
```

```
                275                 280                 285
Ser Pro Gln Ala Gln Gly Ile Leu Thr Thr Val Ser Thr Ile Pro Pro
290                 295                 300

Pro Ala Ser Thr Asn Arg Gln Ser Gly Arg Gln Pro Thr Pro Ile Ser
305                 310                 315                 320

Pro Pro Leu Arg Asp Ser His Pro Gln Ala Met Gln Trp Asn Ser Thr
                325                 330                 335

Ala Phe His Gln Ala Leu Gln Asp Pro Arg Val Arg Gly Leu Tyr Phe
            340                 345                 350

Pro Ala Gly Gly Ser Ser Gly Thr Val Asn Pro Ala Pro Asn Ile
        355                 360                 365

Ala Ser His Ile Ser Ser Ile Ser Ala Arg Thr Gly Asp Pro Val Thr
370                 375                 380

Asn Val Asp Pro Val Leu Thr Pro Glu Gln Ser Ala Gly Met Ile Pro
385                 390                 395                 400

Ala Glu Pro Gly Glu Ser Ala Leu Ser Leu Thr Ser Ser Ala Gly Val
                405                 410                 415

Leu Ser Cys Val Asp Pro Val Leu Thr Pro Glu Gln Ser Ala Gly Met
            420                 425                 430

Ile Pro Ala Glu Pro Gly Glu Ser Ala Leu Ser Leu Thr Ser Ser Ala
        435                 440                 445

Gly Val Leu Ser Cys Ala Glu Asp Leu Gln Glu Ile Leu Pro Val Asn
450                 455                 460

Glu Thr Arg Arg Leu Thr Thr Ser Gly Ala Tyr Asn Ile Ile Asp Gly
465                 470                 475                 480

Cys Ala Glu Asp Leu Gln Glu Ile Leu Pro Val Asn Glu Thr Arg Arg
                485                 490                 495

Leu Thr Thr Ser Gly Ala Tyr Asn Ile Ile Asp Gly Cys Cys Arg His
            500                 505                 510

Gly Phe Phe Gln Val Val Asn Asn Asn Tyr Asp Lys Trp Gly Ser Tyr
        515                 520                 525

Ala Ile Gly Gly Ser Ala Ser Pro Thr Ile Leu Cys Arg His Gly Phe
530                 535                 540

Phe Gln Val Val Asn Asn Asn Tyr Asp Lys Trp Gly Ser Tyr Ala Ile
545                 550                 555                 560

Gly Gly Ser Ala Ser Pro Thr Ile Leu Ala Glu Asp Leu Gln Glu Ile
                565                 570                 575

Leu Pro Val Asn Glu Thr Arg Arg Leu Thr Thr Ser Gly Ala Tyr Asn
            580                 585                 590

Ile Ile Asp Gly Cys His His His His His
        595                 600

<210> SEQ ID NO 69
<211> LENGTH: 597
<212> TYPE: PRT
<213> ORGANISM: Artificial Sequence
<220> FEATURE:
<223> OTHER INFORMATION: K4T

<400> SEQUENCE: 69

Ala Glu Asp Leu Gln Glu Ile Leu Pro Val Asn Glu Thr Arg Arg Leu
1               5                   10                  15

Thr Thr Ser Gly Ala Tyr Asn Ile Ile Asp Gly Ser Ser Arg His Gly
            20                  25                  30

Phe Phe Gln Val Val Asn Asn Asn Tyr Asp Lys Trp Gly Ser Tyr Ala
```

```
              35                  40                  45
Ile Gly Gly Ser Ala Ser Pro Thr Ile Leu Ser Arg His Gly Phe Phe
 50                  55                  60

Gln Val Val Asn Asn Asn Tyr Asp Lys Trp Gly Ser Tyr Ala Ile Gly
 65                  70                  75                  80

Gly Ser Ala Ser Pro Thr Ile Leu Ala Glu Asp Leu Gln Glu Ile Leu
                 85                  90                  95

Pro Val Asn Glu Thr Arg Arg Leu Thr Thr Ser Gly Ala Tyr Asn Ile
                100                 105                 110

Ile Asp Gly Ser Ala Glu Asp Leu Gln Glu Ile Leu Pro Val Asn Glu
                115                 120                 125

Thr Arg Arg Leu Thr Thr Ser Gly Ala Tyr Asn Ile Ile Asp Gly Ser
                130                 135                 140

Val Asp Pro Val Leu Thr Pro Glu Gln Ser Ala Gly Met Ile Pro Ala
145                 150                 155                 160

Glu Pro Gly Glu Ser Ala Leu Ser Leu Thr Ser Ser Ala Gly Val Leu
                165                 170                 175

Ser Ser Val Asp Pro Val Leu Thr Pro Glu Gln Ser Ala Gly Met Ile
                180                 185                 190

Pro Ala Glu Pro Gly Glu Ser Ala Leu Ser Leu Thr Ser Ser Ala Gly
                195                 200                 205

Val Leu Ser Ser Gly Gly Trp Ser Ser Lys Pro Arg Lys Gly Met Gly
                210                 215                 220

Thr Asn Leu Ser Val Pro Asn Pro Leu Gly Phe Phe Pro Asp His Gln
225                 230                 235                 240

Leu Asp Pro Ala Phe Gly Ala Asn Ser Asn Asn Pro Asp Trp Asp Phe
                245                 250                 255

Asn Pro Ile Lys Asp His Trp Pro Ala Ala Asn Gln Val Gly Val Gly
                260                 265                 270

Ala Phe Gly Pro Gly Leu Thr Pro Pro His Gly Gly Ile Leu Gly Trp
                275                 280                 285

Ser Pro Gln Ala Gln Gly Ile Leu Thr Thr Val Ser Thr Ile Pro Pro
290                 295                 300

Pro Ala Ser Thr Asn Arg Gln Ser Gly Arg Gln Pro Thr Pro Ile Ser
305                 310                 315                 320

Pro Pro Leu Arg Asp Ser His Pro Gln Ala Met Gln Trp Asn Ser Thr
                325                 330                 335

Ala Phe His Gln Ala Leu Gln Asp Pro Arg Val Arg Gly Leu Tyr Phe
                340                 345                 350

Pro Ala Gly Gly Ser Ser Gly Thr Val Asn Pro Ala Pro Asn Ile
                355                 360                 365

Ala Ser His Ile Ser Ser Ile Ser Ala Arg Thr Gly Asp Pro Val Thr
                370                 375                 380

Asn Val Asp Pro Val Leu Thr Pro Glu Gln Ser Ala Gly Met Ile Pro
385                 390                 395                 400

Ala Glu Pro Gly Glu Ser Ala Leu Ser Leu Thr Ser Ser Ala Gly Val
                    405                 410                 415

Leu Ser Ser Val Asp Pro Val Leu Thr Pro Glu Gln Ser Ala Gly Met
                420                 425                 430

Ile Pro Ala Glu Pro Gly Glu Ser Ala Leu Ser Leu Thr Ser Ser Ala
                435                 440                 445

Gly Val Leu Ser Ser Ala Glu Asp Leu Gln Glu Ile Leu Pro Val Asn
                450                 455                 460
```

```
Glu Thr Arg Arg Leu Thr Thr Ser Gly Ala Tyr Asn Ile Ile Asp Gly
465                 470                 475                 480

Ser Ala Glu Asp Leu Gln Glu Ile Leu Pro Val Asn Glu Thr Arg Arg
            485                 490                 495

Leu Thr Thr Ser Gly Ala Tyr Asn Ile Ile Asp Gly Ser Ser Arg His
            500                 505                 510

Gly Phe Phe Gln Val Val Asn Asn Asn Tyr Asp Lys Trp Gly Ser Tyr
            515                 520                 525

Ala Ile Gly Gly Ser Ala Ser Pro Thr Ile Leu Ser Arg His Gly Phe
            530                 535                 540

Phe Gln Val Val Asn Asn Asn Tyr Asp Lys Trp Gly Ser Tyr Ala Ile
545                 550                 555                 560

Gly Gly Ser Ala Ser Pro Thr Ile Leu Ala Glu Asp Leu Gln Glu Ile
            565                 570                 575

Leu Pro Val Asn Glu Thr Arg Arg Leu Thr Thr Ser Gly Ala Tyr Asn
            580                 585                 590

Ile Ile Asp Gly Ser
            595

<210> SEQ ID NO 70
<211> LENGTH: 603
<212> TYPE: PRT
<213> ORGANISM: Artificial Sequence
<220> FEATURE:
<223> OTHER INFORMATION: K4THis

<400> SEQUENCE: 70

Ala Glu Asp Leu Gln Glu Ile Leu Pro Val Asn Glu Thr Arg Arg Leu
1               5                   10                  15

Thr Thr Ser Gly Ala Tyr Asn Ile Ile Asp Gly Ser Ser Arg His Gly
            20                  25                  30

Phe Phe Gln Val Val Asn Asn Asn Tyr Asp Lys Trp Gly Ser Tyr Ala
            35                  40                  45

Ile Gly Gly Ser Ala Ser Pro Thr Ile Leu Ser Arg His Gly Phe Phe
        50                  55                  60

Gln Val Val Asn Asn Asn Tyr Asp Lys Trp Gly Ser Tyr Ala Ile Gly
65                  70                  75                  80

Gly Ser Ala Ser Pro Thr Ile Leu Ala Glu Asp Leu Gln Glu Ile Leu
            85                  90                  95

Pro Val Asn Glu Thr Arg Arg Leu Thr Thr Ser Gly Ala Tyr Asn Ile
            100                 105                 110

Ile Asp Gly Ser Ala Glu Asp Leu Gln Glu Ile Leu Pro Val Asn Glu
            115                 120                 125

Thr Arg Arg Leu Thr Thr Ser Gly Ala Tyr Asn Ile Ile Asp Gly Ser
            130                 135                 140

Val Asp Pro Val Leu Thr Pro Glu Gln Ser Ala Gly Met Ile Pro Ala
145                 150                 155                 160

Glu Pro Gly Glu Ser Ala Leu Ser Leu Thr Ser Ser Ala Gly Val Leu
            165                 170                 175

Ser Ser Val Asp Pro Val Leu Thr Pro Glu Gln Ser Ala Gly Met Ile
            180                 185                 190

Pro Ala Glu Pro Gly Glu Ser Ala Leu Ser Leu Thr Ser Ser Ala Gly
            195                 200                 205

Val Leu Ser Ser Gly Gly Trp Ser Ser Lys Pro Arg Lys Gly Met Gly
            210                 215                 220
```

```
Thr Asn Leu Ser Val Pro Asn Pro Leu Gly Phe Phe Pro Asp His Gln
225                 230                 235                 240

Leu Asp Pro Ala Phe Gly Ala Asn Ser Asn Asn Pro Asp Trp Asp Phe
                245                 250                 255

Asn Pro Ile Lys Asp His Trp Pro Ala Ala Asn Gln Val Gly Val Gly
            260                 265                 270

Ala Phe Gly Pro Gly Leu Thr Pro Pro His Gly Gly Ile Leu Gly Trp
        275                 280                 285

Ser Pro Gln Ala Gln Gly Ile Leu Thr Thr Val Ser Thr Ile Pro Pro
    290                 295                 300

Pro Ala Ser Thr Asn Arg Gln Ser Gly Arg Gln Pro Thr Pro Ile Ser
305                 310                 315                 320

Pro Pro Leu Arg Asp Ser His Pro Gln Ala Met Gln Trp Asn Ser Thr
                325                 330                 335

Ala Phe His Gln Ala Leu Gln Asp Pro Arg Val Arg Gly Leu Tyr Phe
                340                 345                 350

Pro Ala Gly Gly Ser Ser Ser Gly Thr Val Asn Pro Ala Pro Asn Ile
            355                 360                 365

Ala Ser His Ile Ser Ser Ile Ser Ala Arg Thr Gly Asp Pro Val Thr
        370                 375                 380

Asn Val Asp Pro Val Leu Thr Pro Glu Gln Ser Ala Gly Met Ile Pro
385                 390                 395                 400

Ala Glu Pro Gly Glu Ser Ala Leu Ser Leu Thr Ser Ser Ala Gly Val
                405                 410                 415

Leu Ser Ser Val Asp Pro Val Leu Thr Pro Glu Gln Ser Ala Gly Met
                420                 425                 430

Ile Pro Ala Glu Pro Gly Glu Ser Ala Leu Ser Leu Thr Ser Ser Ala
        435                 440                 445

Gly Val Leu Ser Ser Ala Glu Asp Leu Gln Glu Ile Leu Pro Val Asn
    450                 455                 460

Glu Thr Arg Arg Leu Thr Thr Ser Gly Ala Tyr Asn Ile Ile Asp Gly
465                 470                 475                 480

Ser Ala Glu Asp Leu Gln Glu Ile Leu Pro Val Asn Glu Thr Arg Arg
                485                 490                 495

Leu Thr Thr Ser Gly Ala Tyr Asn Ile Ile Asp Gly Ser Ser Arg His
                500                 505                 510

Gly Phe Phe Gln Val Val Asn Asn Asn Tyr Asp Lys Trp Gly Ser Tyr
            515                 520                 525

Ala Ile Gly Gly Ser Ala Ser Pro Thr Ile Leu Ser Arg His Gly Phe
        530                 535                 540

Phe Gln Val Val Asn Asn Asn Tyr Asp Lys Trp Gly Ser Tyr Ala Ile
545                 550                 555                 560

Gly Gly Ser Ala Ser Pro Thr Ile Leu Ala Glu Asp Leu Gln Glu Ile
                565                 570                 575

Leu Pro Val Asn Glu Thr Arg Arg Leu Thr Thr Ser Gly Ala Tyr Asn
            580                 585                 590

Ile Ile Asp Gly Ser His His His His His
        595                 600
```

POLYPEPTIDE CONSTRUCT COMPRISING FRAGMENTS OF ALLERGENS

TECHNICAL FIELD

The present invention is in the field of vaccines to be used in the treatment or prevention of allergies or allergic reaction caused by allergens, preferably by allergens of *Ambrosia artemisiifolia*.

BACKGROUND ART

More than 36 million individuals worldwide are affected by ragweed (*Ambrosia artemisiifolia*) allergy. Due to the high allergenicity and high potential of the plant to colonize new geographical areas, the number of patients is increasing rapidly. The accompanying symptoms such as rhinorrhea, sneezing, itching and conjunctivitis have an enormous effect on quality of life. Alarming is also the fact that 40-50% of ragweed allergic patients develop asthmatic symptoms. Beside medications which combat the symptoms, only allergen specific immunotherapies (SIT) based on allergen extracts are available. Much to the chagrin of patients this immunotherapy requires a high number of injections with the requirement of careful updosing and potentially causes severe IgE-mediated and T cell mediated side effects including fatal anaphylaxis. Implying that there is an urgent need for new disease modifying therapy approaches.

WO 93/00077 discloses therapeutic compositions comprising allergens of *Ambrosia artemisiifolia*. These compositions can be used in the oral treatment of patients suffering from ragweed allergy.

In WO 96/013589 pharmaceutical preparations comprising fragments of allergens of *Ambrosia artemisiifolia* comprising at least one T cell epitope are described.

Also WO 2008/098749 discloses fragments of *Ambrosia artemisiifolia* allergens which can be used in the treatment of allergies caused by these allergens.

WO 2013/001362 relates to compositions which comprise a plurality of overlapping fragments derived from Amb a 1, the major *Ambrosia artemisiifolia* allergen. These fragments cover the entire Amb a 1 allergen but do not include the N-terminus of the mature Amb a 1 molecule.

In WO 2001/035991 and in WO 2006/096497 conjugates are described which comprise a polynucleotide comprising an immunostimulatory sequence (ISS) and an antigen which can be Amb a 1 or an antigenic fragment thereof.

WO 2004/000351 relates to compositions for enhancing an immune response in an animal whereby these compositions comprise a virus-like particle, an immunostimulatory substance and an antigen, which can be an allergen like Amb a 1.

In WO 2010/018378 T-cell reactive fragments derived from Amb a 1 are disclosed. These fragments can be used use in preventing or treating allergy to ragweed by tolerisation.

SUMMARY OF INVENTION

Most of the known vaccines used to treat or prevent allergies in patients show either an undesired IgE reaction when administered to an individual or are not able to induce an immune response which can efficiently prevent allergic reactions.

Therefore, it is an object of the present invention to provide a polypeptide construct and preparations comprising such a construct to treat individuals suffering from ragweed allergy. The preparation should be able to prevent the allergic reaction to ragweed pollen exposure and eliminate IgE-mediated side effects as well as late phase side effects due to a reduced IgE reactivity and reduced activation of allergen-specific T cells. Furthermore, it is desirable that these preparations are administered to patients only in a low number of injections to achieve a long-time benefit in order to ensure compliance and adherence of patients to the treatment.

Amb a 1 has been identified as the major allergen of ragweed pollen (Rafnar et al., J. Biol. Chem. 266(1991): 1229-1236). Several Amb a 1 isoforms are present in the ragweed pollen. Their sequences have been described and are disclosed in gene- or protein databases (e.g. www.allergome.org, GenBank).

The present invention relates to a polypeptide construct comprising at least two fragments of a mature allergen derived from an allergen of the Amb a 1 family of *Ambrosia artemisiifolia* or variants of said at least two fragments, wherein each of the at least two fragments consist of 20 to 50 amino acid residues and wherein at least one fragment is derived from amino acid residues 1 to 50 of the mature allergen and at least one fragment is derived from amino acid residues starting at 240 and ending at the C-terminal end of the mature allergen.

It turned out that polypeptide constructs comprising the aforementioned fragments, when administered to an individual, induce the expression of IgG antibodies that are able to efficiently block the binding of allergen specific IgE molecules to the respective allergen. Due to this inhibition IgE mediated degranulation of mast cells and basophils is prevented or at least substantially inhibited.

Another aspect of the present invention relates to a nucleic acid molecule encoding a polypeptide construct as defined herein.

A further aspect of the present invention relates to a vector comprising a nucleic acid molecule according to the present invention.

Yet another aspect of the present invention relates to a host cell comprising a nucleic acid molecule or a vector according to the present invention.

A further aspect of the present invention relates to a vaccine formulation comprising at least one polypeptide construct, a nucleic acid molecule or a vector according to the present invention.

BRIEF DESCRIPTION OF THE FIGURES

FIG. 1 shows the amino acid sequence of Amb a 1.0305 (SEQ ID No. 1) and fragments thereof.

FIG. 2 shows the IgE reactivity of the fragments of FIG. 1 measured with an IgE ELISA. As controls natural Amb a 1 which was purified from an extract of *Ambrosia artemisiifolia* (nAmb a 1) and recombinantly produced Amb a 1 (rAmb a 1; sequence depicted in FIG. 1) have been used.

FIGS. 3A and 3B show Amb a 1 specific antibodies after immunization of rabbits with the fragments depicted in FIG. 1.

FIGS. 4A and 4B show six polypeptide constructs (fusion proteins) comprising the fragments depicted in FIG. 1 fused to PreS as carrier.

FIG. 7 shows the results of a similar inhibition ELISA experiment as shown in FIG. 6. The inhibitor sera (i.e. sera from rabbits immunized with polypeptide constructs and wild-type Amb a 1 as a control) were titrated with dilutions ranging from 1:10 to 1:100. Allergen-specific antibodies present in the inhibition sera are able to inhibit binding of patient's IgE. The columns from left to right at each dilution show the results obtained with sera obtained by vaccinating rabbits with constructs K1, K2, K3, K4, K6 and with recombinant Amb a 1, respectively.

FIG. 8 shows the IgE reactivity of 5 variants (K4A, K4B, K4C, K4D and K4E) of the polypeptide construct K4 shown in FIGS. 4A and 4B. The IgE reactivity was measured with an IgE ELISA.

FIG. 11 shows the results of inhibition ELISA using sera obtained by immunizing rabbits with single peptides and mixtures of these sera. Antibodies comprised within sera of rabbits immunized with peptides 1 to 5 and 7 to 11 of example 1 (FIG. 11A) adjuvanted with Alum (thus comprising antibodies directed to the aforementioned peptides) and mixtures of these sera containing antibodies directed to peptides 1+9+11, 2+9+11, 8+9+11, 3+4+5, 5+7+8, 1+9+10+11 (FIG. 11B) and peptides 2+11, 1+2, 1+8 and 1+11 (FIG. 11C), respectively, are able to inhibit binding of allergen specific IgE from ragweed allergic individuals to Amb a 1. The inhibition of IgE binding obtained with sera from rabbits immunized with wild-type Amb a 1 (nAmb a 1) was included in the experiment as a control.

DESCRIPTION OF EMBODIMENTS

Figure 5:
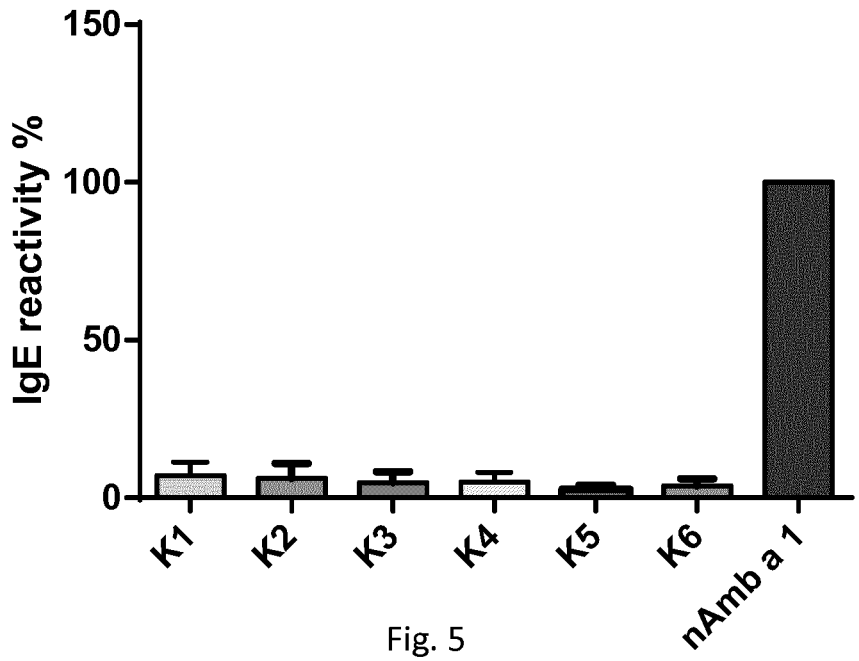
FIG. 5 shows the IgE reactivity of the constructs of FIGS. 4A and 4B measured with an IgE ELISA. Amb a 1 purified from an extract of *Ambrosia artemisiifolia* (nAmb a 1) was used as control.

The polypeptide construct of the present invention comprises at least two fragments of a mature allergen derived from an allergen of the Amb a 1 family of *Ambrosia artemisiifolia* or variants of said at least two fragments, wherein each of the at least two fragments consist of 20 to 50 amino acid residues and wherein at least one fragment is derived from amino acid residues 1 to 50 of the mature allergen and at least one fragment is derived from amino acid residues starting at 240 and ending at the C-terminal end of the mature allergen.

It turned surprisingly out that—upon administration to an individual—a polypeptide construct of the present invention comprising at least one fragment from the N-terminal end of a mature allergen derived from an allergen of the Amb a 1 family of *Ambrosia artemisiifolia* and at least one fragment from the C-terminal end of a mature allergen derived from an allergen of the Amb a 1 family of *Ambrosia artemisiifolia* is able to induce the formation of IgG molecules that are able to block efficiently the binding of allergen specific IgE molecules to the allergen. Apparently the presence of fragments from the N- as well as from the C-terminus of a mature allergen is required to obtain the claimed surprising effect.

A "polypeptide construct", as used herein, refers to a conjugate or fusion protein comprising the at least two fragments of a mature allergen derived from an allergen of the Amb a 1 family of *Ambrosia artemisiifolia* or variants of said at least two fragments. The polypeptide constructs of the present invention may comprise other peptides, polypeptides or proteins (e.g. carrier proteins) or other chemical moieties next to the at least two fragments.

The term "allergen of the Amb a 1 family", as used herein, refers to the group of known isoforms of Amb a 1. This includes in particular isoforms Amb a 1.0101 (GenBank Acc. No. AAA32665), Amb a 1.0201 (GenBank Acc. No. AAA32666), Amb a 1.0202 (GenBank Acc. No. CBW30987), Amb a 1.0301 (GenBank Acc. No. AAA32668), Amb a 1.0302 (UniProt Acc. No. P27761 variant L48Y), Amb a 1.0303 (GenBank Acc. No. AAA32669), Amb a 1.0304 (GenBank Acc. No. CBW30988), Amb a 1.0305 (GenBank Acc. No. CBW30989), Amb a 1.0401 (GenBank Acc. No. AAA32670), Amb a 1.0402 (GenBank Acc. No. CBW30993), Amb a 1.0501 (GenBank Acc. No. AAA32671) and Amb a 1.0502 (GenBank Acc. No. CBW30995). Thus, "a mature allergen derived from an allergen of the Amb a 1 family of *Ambrosia artemisiifolia*" means that a mature allergen is selected from the above identified group of isoforms.

The term "conjugate", as used herein, is intended to refer to the molecule formed as a result of covalent linking of at least two conjugation partners to another. The "conjugate" of the present invention comprises the at least two fragments of the present invention. Conjugation between two or more peptides, polypeptides or proteins is, for instance, achieved via an N-terminal cysteine or C-terminal cysteine amide residue added to the one of the conjugation partners resulting in a molecule containing a free sulfhydryl group. To said terminal cysteine residue any maleimide-activated polypeptide or protein may be conjugated. If the conjugation partners do not have a cysteine residue at a terminus, EDC (1-ethyl-3-(3-dimethylaminopropyl) carbodiimide hydrochloride) chemistry in order to couple amines (lysine) or carboxylic acids (glutamic, aspartic acid or 5'-phosphate) to a conjugation partner may be employed. Crosslinking between the peptide and the carrier is then for instance effected with an MBS (m-maleimidobenzoyl-N-hydroxysuccinimide ester) coupling agent.

The at least two fragments may be coupled to a carrier protein in order to obtain a conjugation product which allows to induce the formation of allergen specific IgG antibodies more efficiently. For instance, Keyhole limpet haemocyanin (KLH) or bovine or human serum albumin can be used as carrier proteins. Also other carrier proteins like ovalbumin, thyroglobulin, tetanus toxoid or diphtheria toxoid can be used.

The polypeptide construct of the present invention can also be a fusion protein. "Fusion protein", as used herein, refers to a protein or polypeptide wherein the allergen fragments and/or other proteins, polypeptides or peptides are expressed and prepared as one single and unique recombinant polypeptide chain.

The at least two fragments of the mature allergen may be conjugated or fused to each other and/or the other proteins, polypeptides or peptides either directly or via a linker. Such a linker may be a peptide or polypeptide or any other chemical moiety capable to covalently bind peptides, polypeptides or proteins.

The terms "of a mature allergen" and "derived from a mature allergen", as used herein, mean that the amino acid sequences of fragments according to the present invention are obtained from the amino acid sequence of an allergen by fragmentation or truncation. Therefore, the at least two fragments consist of 20 to 50 consecutive amino acid residues of the mature allergen from which they are derived from.

"Mature allergen", as defined herein, refers to the amino acid sequence of a processed allergen which lacks a signal peptide. The allergen itself is encoded by the respective gene which still contains a signal peptide. The signal peptide of an allergen can be identified by methods known in the art including sequence alignments (see e.g. Bendtsen J D et al., J Mol Biol. 340(2004):783-95; Björklund AK et al., Bioinformatics 21(2005):39-50). A simple method to identify the amino acid sequence of a mature allergen is to isolate the mature allergen from an allergen source and to sequence its N-terminal end. These sequence data may be compared with the sequence of the gene or the mRNA encoding the same allergen to identify the amino acid sequence of the mature allergen and of the signal peptide. Thus, the sequence of a "mature allergen" is encoded by its mRNA and/or gene and does not include cleavage products potentially obtained by post-translational modifications of primary translated mRNA or gene products apart from the potential cleavage of the signal peptide. "Mature allergen" reflects the amino acid sequence encoded by an mRNA molecule lacking the signal peptide.

According to the present invention the polypeptide construct may comprise at least two fragments of a mature allergen derived from an allergen of the Amb a 1 family of *Ambrosia artemisiifolia* or variants of said at least two fragments. The number of fragments may vary from two to 20, preferably from two to 19, more preferably from two to 18, more preferably from two to 17, more preferably from two to 16, more preferably from two to 15, more preferably from two to 14, more preferably from two to 13, more preferably from two to 12, more preferably from two to 11, more preferably from two to ten, more preferably from two to nine, more preferably from two to eight, more preferably from two to seven, more preferably from two to six, more preferably from two to five. It is particularly preferred that the fragments used in the polypeptide construct of the present invention are not located adjacent to each other in the mature allergen and that at least two fragments are selected which do not consist of the same amino acid sequence. However, if more than one copy of the same fragment is present in the polypeptide construct of the present invention, this construct has to comprise at least one further fragment as defined herein consisting of another amino acid sequence.

The polypeptide construct of the present invention may comprise one or more copies of the same fragment. It is particularly preferred that the polypeptide construct of the present invention comprises at least one, preferably at least two, more preferably at least three, more preferably at least four, more preferably at least five, copies of the same fragment. In a particularly preferred embodiment of the present invention the polypeptide construct comprises three, four, five or six, preferably four, copies of the same fragment.

Furthermore, the polypeptide construct of the present invention may also comprise variants of fragments of a mature allergen of *Ambrosia artemisiifolia*. These variants comprise particularly preferred one or more amino acid exchanges.

The variants of the present invention may have "conservative" changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. The variants of the present invention may also have "non-conservative" changes (for example, replacement of a glycine with a tryptophan). Similar minor variations may also include amino acid deletions or insertions, or both. Variants of peptides and molecules described herein have less than 20%, preferably less than 10%, more preferably less than 5% changes (whether substitutions, deletions, and insertions).

Particularly preferred variants of the fragments of the mature allergen include substitutions or deletions of one or more cysteine residues naturally occurring in the mature allergen derived from an allergen of the Amb a 1 family of *Ambrosia artemisiifolia*. One or more of these cysteine residues can be substituted with any other amino acid residue, whereby it is particularly preferred that the cysteine residues are substituted with serine. Alternatively, one or more of the cysteine residues of the variants of the fragments are deleted. It turned surprisingly out that fragments having a reduced number (deleted or substituted) or lacking most or all cysteine residues show an even higher IgE inhibition compared to unmodified fragments still comprising all or nearly all naturally occurring cysteine residues.

It is particularly preferred that the at least two fragments of the polypeptide construct of the present invention exhibit hypoallergenic properties. The term "hypoallergenic" as used herein refers to the ability of the fragments of the present invention to induce reduced or no allergic reactions when administered to an individual. There are methods known in the art how to determine whether a fragment or polypeptide construct is hypoallergenic. For instance, the IgE reactivity of the polypeptide or fragment can be measured by ELISA using sera from ragweed allergic individuals and compared to the IgE reactivity of the wild-type allergen. Hypoallergenic fragments show a reduced IgE reactivity compared to the wild-type allergen. The reduced or missing ability of "hypoallergenic" fragments of an allergen to induce an allergic reaction in an individual is obtained by removing or destroying the IgE binding epitopes from said allergenic polypeptide. Fragmentation of a mature wild-type allergen is in many cases a well established method to obtain such molecules. A polypeptide construct of the present invention exhibits preferably an at least 30%, more preferably an at least 40%, more preferably an at least 50%, more preferably an at least 60%, more preferably an at least 70%, more preferably an at least 80%, more preferably an at least 90%, more preferably an at least 95%, reduced or even more preferably no IgE binding capacity or binding affinity to allergen specific IgE molecules compared to the wild-type allergen.

"IgE binding capacity", as used herein, is the capacity of a molecule to bind to IgE which is able to bind to a specific allergenic polypeptide. The IgE binding capacity of polypeptides and proteins can be determined by, for example, an enzyme linked immunosorbent assay (ELISA) using, for example, sera obtained from one or more individuals (i.e. allergic individuals) who have been previously exposed to the mature allergen.

The at least two fragments of the polypeptide construct may or may not comprise T-cell epitopes. T-cell epitopes can be identified by methods known in the art (e.g. ELISpot).

According to a preferred embodiment of the present invention the allergen of the Amb a 1 family is selected from the group consisting of Amb a 1.0101 (GenBank Acc. No. AAA32665), Amb a 1.0201 (GenBank Acc. No. AAA32666), Amb a 1.0202 (GenBank Acc. No. CBW30987), Amb a 1.0301 (GenBank Acc. No. AAA32668), Amb a 1.0302 (UniProt Acc. No. P27761 variant L48Y), Amb a 1.0303 (GenBank Acc. No. AAA32669), Amb a 1.0304 (GenBank Acc. No. CBW30988), Amb a 1.0305 (GenBank Acc. No. CBW30989), Amb a 1.0401 (GenBank Acc. No. AAA32670), Amb a 1.0402 (GenBank Acc. No. CBW30993), Amb a 1.0501 (GenBank Acc. No. AAA32671) and Amb a 1.0502 (GenBank Acc. No. CBW30995).

Amb a 1 isoforms Amb a 1.0101, Amb a 1.0201, Amb a 1.0305 and Amb a 1.0401 are particularly preferred since most of the people suffering from ragweed allergy turned out to be particularly reactive with these isoforms. Therefore at least one of the at least two fragments of the allergen derived from an allergen of the Amb a 1 family of *Ambrosia artemisiifolia* is derived from one or more of these Amb a 1 isoforms.

According to a further preferred embodiment of the pre sent invention the at least one fragment is derived from amino acid residues 1 to 50 of the mature allergen comprises amino acid residues 1 to 20-40, preferably amino acid residues 1 to 25-35, more preferably amino acid residues 1 to 28-30, of the mature allergen.

"Amino acid residues 1 to 20-40", as indicated above, means that the fragment may comprise or consist of amino acid residues 1 to an integer ranging from 20 to 40 including amino acid residue 21, 22, 23, 24, 25, 26, 27, 28, 29, 30, 31, 32, 33, 34, 35, 36, 37, 38 and 39. This is applicable to all amino acid ranges indicated herein.

The polypeptide construct of the present invention may also comprise fragments which are derived from other parts of the allergen. For instance, at least one further fragment of the polypeptide construct of the present invention may be derived from amino acid residues 80-85 to 160-170 of the mature allergen comprises amino acid residues 88-90 to 151-153, preferably amino acid residues 88-90 to 117-119 or 118-120 to 151-153, of the mature allergen.

According to another preferred embodiment of the present invention the at least one fragment is derived from amino acid residue starting at 240 and ending at the C-terminal end of the mature allergen comprises amino acid residues 240 to 367-373, preferably amino acid residues 240 to 367-373, more preferably amino acid residues 243-253 to 367-373, of the mature allergen.

According to another preferred embodiment of the present invention at least one fragment is derived from amino acid residue starting at 240 and ending at the C-terminal end of the mature allergen comprises amino acid residues 240 to 310-320, preferably amino acid residues 240-260 to 300-310, more preferably amino acid residues 248-253 to 278-283, of the mature allergen.

According to another preferred embodiment of the present invention at least one fragment is derived from amino acid residue starting at 240 and ending at the C-terminal end of the mature allergen comprises amino acid residues 310-320 to 367-373, preferably amino acid residues 320-330 to 367-373, more preferably amino acid residues 328-334 to 361-367, of the mature allergen.

The at least two fragments being part of the polypeptide construct of the present invention are selected from the above identified group of fragments. Particularly preferred fragments to be combined in one or more polypeptide constructs include at least one fragment derived from amino acid residues 1 to 50, preferably 1 to 20-40, more preferably 1 to 25-35, more preferably amino acid residues 1 to 28-30, of the mature allergen, at least one fragment derived from amino acid residues starting at 240 and ending at the C-terminal end of the mature allergen, preferably amino acid residues 240 to 310-320, more preferably amino acid residues 240-260 to 300-310, more preferably amino acid residues 248-253 to 278-283, of the mature allergen and/or at least one fragment comprising amino acid residues 310-320 to 367-373, preferably amino acid residues 320-330 to 367-373, more preferably amino acid residues 328-334 to 361-367, of the mature allergen.

The term "at least one fragment is derived from amino acid residues X to Y", as used herein, means that the fragment comprises or consists of an amino acid stretch beginning at amino acid residues X and ending at amino acid residue Y of the mature allergen.

The at least two fragments present in the polypeptide construct according to the present invention may consist independently of 25 to 45, preferably of 25 to 40, more preferably 26 to 35, more preferably of 28 to 34, amino acid residues.

In a particular preferred embodiment of the present invention the at least two fragments may consist independently of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive amino acid residues of a mature allergen in the regions defined herein.

According to a preferred embodiment of the present invention the polypeptide construct comprises at least one allergen fragment derived from amino acid residues 1 to 50 of the mature allergen selected from the group consisting of AEDLQEILPVNETRRLTTSGAYNIIDGX$_1$ (SEQ ID No. 2), AEDLQQILPSANETRSLTTX$_2$GTYNIIDGX$_1$ (SEQ ID No. 3), AEGVGEILPSVNETRSLQAX$_2$EAYNIIDKX$_1$ (SEQ ID No. 4), AEDVEEFLPSANETRRSLKAX$_2$EAHNIIDKX$_1$ (SEQ ID No. 5) and variants thereof having an at least 70% identity thereto, wherein X$_1$ is cysteine, serine or no amino acid residue and X$_2$ is cysteine or serine.

According to a further preferred embodiment of the present invention the polypeptide construct comprises at least one fragment derived from amino acid residues 240 to the C-terminal end of the mature allergen selected from the group consisting of X$_3$RX$_4$GFX$_5$QVVNNNYX$_6$X$_7$WGX$_8$YAX$_9$GGSX$_{10}$X$_{11}$PTIL (SEQ ID No. 6) and variants thereof having an at least 70% identity thereto, wherein X$_3$ is cysteine, serine, leucine or no amino acid residue, X$_4$ is histidine or phenylalanine, X$_5$ is phenylalanine or valine, $X_6$ is aspartic acid or glutamic acid, $X_7$ is arginine or lysine, $X_8$ is threonine or serine, $X_9$ is isoleucine or leucine, $X_{10}$ is serine or alanine and $X_{11}$ is glycine, serine or alanine.

According to another preferred embodiment of the present invention the polypeptide construct comprises at least one fragment derived from amino acid residues 240 to the C-terminal end of the mature allergen selected from the group consisting of $X_{12}$DPVLTP$X_{13}$Q$X_{14}$AGMIPAEPGE$X_{15}X_{16}X_{17}X_{18}$LTS SAGVLS$X_{19}$ (SEQ ID No. 7) and variants thereof having an at least 70% identity thereto, wherein $X_{12}$ is serine or valine, $X_{13}$ is valine or glutamic acid, $X_{14}$ is serine, lysine or asparagine, $X_{15}$ is alanine or serine, $X_{16}$ is valine or alanine, $X_{17}$ is leucine or isoleucine, $X_{18}$ is serine, lysine or arginine and $X_{19}$ is cysteine, serine or no amino acid residue.

The polypeptide construct of the present invention comprises preferably at least one fragment derived from amino acid residues 240 to the C-terminal end of the mature allergen is selected from the group consisting of $X_{20}$RHGFFQVVNNNYDKWGSYAIGGSASPTIL (SEQ ID No. 8), $X_{21}$RFGFFQVVNNNYDRWGTYAIGGSSAPTIL (SEQ ID No. 9), VDPVLTPEQSAGMIPAEPGESALSLTSSAGVLS$X_{22}$ (SEQ ID No. 10) and SDPVLTPVQSAGMIPAEPGEAAIKLTSSAGVLS$X_{23}$ (SEQ ID No. 11), $X_{20}$ and $X_{21}$ are independently cysteine, leucine, serine or no amino acid residue, $X_{22}$ and $X_{23}$ are independently cysteine, serine or no amino acid residue.

According to another preferred embodiment of the present invention the polypeptide construct comprises at least one allergen fragment derived from amino acid residues 80-85 to 160-170 of the mature allergen selected from the group consisting of PLWIIFERDMVIRLDKEMVVNSDKTIDGRG (SEQ ID No. 12), PLWIIFARDMVIRLDRELAINNDKTIDGRG (SEQ ID No. 13), PLWIIFKNDMVINLNQELVVNSDKTIDGRG (SEQ ID No. 14), PLWIIFKRNMVIHLNQELVVNSDKTIDGRG (SEQ ID No. 15) and variants thereof having an at least 70% identity thereto.

According to a further preferred embodiment of the present invention the polypeptide construct comprises at least one allergen fragment derived from amino acid residues 80-85 to 160-170 of the mature allergen selected from the group consisting of AKVEIINAGFTLNGVKNVIIHNINMHDVKVNPG (SEQ ID No. 16), AKVEIINAGFAIYNVKNIIIHNIIMHDIVVNPG (SEQ ID No. 17), VKVEIINGGLTLMNVKNIIIHNINIHDVKVLPG (SEQ ID No. 18), VKVNIVNAGLTLMNVKNIIIHNINIHDIKVCPG (SEQ ID No. 19) and variants thereof having an at least 70% identity thereto.

The polypeptide construct comprises at least one allergen fragment derived from amino acid residues 240 to the C-terminal end of the mature allergen selected from the group consisting of AGDENIEDRGMLATVAFNTFTDNVDQRMPR (SEQ ID No. 20), DFDERGMLCTVAFNKFTDNVDQRMPN (SEQ ID No. 21), ADDTHVQDKGMLATVAFNMFTDNVDQRMPR (SEQ ID No. 22), ADDTHYQDKGMLATVAFNMFTDHVDQRMPR (SEQ ID No. 23) and variants thereof having an at least 70% identity thereto.

The at least two fragments of the polypeptide construct of the present invention are selected from the above identified allergen fragments. Also encompassed are variants of the allergen fragments having preferably at least 70%, more preferably at least 75%, more preferably at least 85%, more preferably at least 90%, more preferably at least 95%, identity to fragments obtained from a mature allergen derived from an allergen of the Amb a 1 family of *Ambrosia artemisiifolia* allergen. Preferred variants of the specific fragments mentioned above comprise amino acid substitutions and/or deletions at cysteine residues, whereby cysteine residues may be substituted with serine residues, for instance.

The degree of identity of a first amino acid sequence to a second amino acid can be determined by a direct comparison between both amino acid sequences using certain algorithms. Sequence identity is preferably determined by BLAST alignment (http://blast.ncbi.nlm.nih.gov/; Altschul S F et al J. Mol. Biol. 215 (1990): 403-410) using the BLOSUM62 matrix, a gap existence penalty of 11, and a gap extension penalty of 1.

The polypeptide construct of the present invention may be a fusion protein comprising the at least two fragments of the mature allergen derived from an allergen of the Amb a 1 family of *Ambrosia artemisiifolia*. The at least two fragments are preferably selected from the group consisting of AEDLQEILPVNETRRLTTSGAYNIIDG$X_1$ (SEQ ID No. 2), AEDLQQILPSANETRSLTT$X_2$GTYNIIDG$X_1$ (SEQ ID No. 3), AEGVGEILPSVNETRSLQA$X_2$EAYNIIDK$X_1$ (SEQ ID No. 4), AEDVEEFLPSANETRRSLKA$X_2$EAHNIIDK$X_1$ (SEQ ID No. 5), $X_3$R$X_4$GF$X_5$QVVNNNY$X_6X_7$WG$X_8$YA$X_9$GGS$X_{10}X_{11}$PTIL (SEQ ID No. 6), preferably $X_{20}$RHGFFQVVNNNYDKWGSYAIGGSASPTIL (SEQ ID No. 8) or $X_{21}$RFGFFQVVNNNYDRWGTYAIGGSSAPTIL (SEQ ID No. 9), $X_{12}$DPVLTP$X_{13}$Q$X_{14}$AGMIPAEPGE$X_{15}X_{16}X_{17}X_{18}$LTSS AGVLS$X_{19}$ (SEQ ID No. 7), preferably VDPVLTPEQSAGMIPAEPGESALSLTSSAGVLS$X_{22}$ (SEQ ID No. 10) or SDPVLTPVQSAGMIPAEPGEAAIKLTSSAGVLS$X_{23}$ (SEQ ID No. 11), and variants thereof.

According to a preferred embodiment of the present invention the polypeptide construct comprises at least one fragment of a mature allergen derived from an allergen of the Amb a 1 family of *Ambrosia artemisiifolia* selected from the group consisting of $X_{21}$RFGFFQVVNNNYDRWGTYAIGGSSAPTIL (SEQ ID No. 9), AEGVGEILPSVNETRSLQA$X_2$EAYNIIDK$X_1$ (SEQ ID No. 4) and SDPVLTPVQSAGMIPAEPGEAAIKLTSSAGVLS$X_{23}$ (SEQ ID No. 11), wherein $X_1$, $X_{21}$ and $X_{23}$ are independently preferably cysteine, serine or no amino acid residue and $X_2$ is preferably cysteine or serine, more preferably serine.

According to a further preferred embodiment of the present invention the polypeptide construct comprises at least one fragment of a mature allergen derived from an allergen of the Amb a 1 family of *Ambrosia artemisiifolia* selected from the group consisting of $X_{20}$RHGFFQVVNNNYDKWGSYAIGGSASPTIL (SEQ ID No. 8), AEDLQEILPVNETRRLTTSGAYNIIDG$X_1$ (SEQ ID No. 2) and VDPVLTPEQSAGMIPAEPGESALSLTSSAGVLS$X_{22}$ (SEQ ID No. 10), wherein $X_1$, $X_{20}$ and $X_{22}$ are independently preferably cysteine, serine or no amino acid residue and $X_2$ is preferably cysteine or serine, more preferably serine.

According to another preferred embodiment of the present invention the polypeptide construct comprises at least one fragment of a mature allergen derived from an allergen of the Amb a 1 family of *Ambrosia artemisiifolia* selected from the group consisting of $X_{20}$RHGFFQVVNNNYDKWGSYAIGGSASPTIL (SEQ ID No. 8), AEDLQEILPVNETRRLTTSGAYNIIDGX$_1$ (SEQ ID No. 2), VDPVLTPEQSAGMIPAEPGESALSLTS-SAGVLSX$_{22}$ (SEQ ID No. 10), X$_{21}$RFGFFQVVNNNYDRWGTYAIGGSSAPTIL (SEQ ID No. 9), AEGVGEILPSVNETRSLQAX$_2$EAYNIIDKX$_1$ (SEQ ID No. 4) and SDPVLTPVQSAGMIPAEPGEAAI-KLTSSAGVLSX$_{23}$ (SEQ ID No. 11), wherein X$_1$, X$_{20}$, X$_{21}$, X$_{22}$ and X$_{23}$ are independently preferably cysteine, serine or no amino acid residue and X$_2$ is preferably cysteine or serine, more preferably serine.

The at least two fragments are preferably fused or conjugated to a carrier protein.

According to a preferred embodiment of the present invention the carrier protein is a viral protein or a fragment thereof consisting of 50 to 300, preferably 60 to 250, more preferably 80 to 200, more preferably 100 to 200, amino acid residues.

According to a further preferred embodiment of the present invention the viral protein is a capsid protein.

The viral protein is preferably derived from a virus of the hepadnaviridae family.

According to a preferred embodiment of the present invention the virus of the hepadnaviridae family is a Hepatitis B virus.

According to a further preferred embodiment of the present invention the viral protein of the Hepatitis B virus is PreS or a fragment thereof, preferably PreS1 or PreS2.

A fragment of a hepatitis B PreS polypeptide consists preferably of at least 30, preferably at least 40, more preferably at least 50, consecutive amino acid residues and may comprise PreS1 and/or PreS2 of the hepatitis B PreS polypeptide.

The Hepatitis B PreS polypeptide in its function as a carrier protein and being used as a fusion or conjugation partner for the at least two fragments of a mature allergen derived from an allergen of the Amb a 1 family of *Ambrosia artemisiifolia* or variants of said at least two fragments may comprise or consist of the following amino acid sequence (SEQ ID No. 24):

GGWSSKPRKGMGTNLSVPNPLGFFPDHQLDPAFGANSNNPDWDFNPIKDH

WPAANQVGVGAFGPGLTPPHGGILGWSPQAQGILTTVSTIPPPASTNRQS

GRQPTPISPPLRDSHPQAMQWNSTAFHQALQDPRVRGLYFPAGGSSSGTV

NPAPNIASHISSISARTGDPVTN

The Hepatitis B PreS polypeptide may consist of an amino acid sequence which is at least 70%, preferably at least 80%, more preferably at least 90%, more preferably at least 95%, more preferably at least 99%, in particular 100%, identical to SEQ ID No. 24.

According to a preferred embodiment of the present invention the at least two allergen fragments are fused to the N-terminus and/or C-terminus of the carrier protein.

According to a particular preferred embodiment of the present invention at least one of said at least two fragments is fused to the N-terminus of the carrier protein and at least one of said at least two fragments is fused to the C-terminus of the carrier protein.

It turned out that fusing a part of the fragments of the mature allergen derived from an allergen of the Amb a 1 family of *Ambrosia artemisiifolia* or variants of said at least two fragments to the N-terminus and another part to the C-terminus of a carrier protein results in an increased production of antibodies directed to a polypeptide or protein from which the fragments have been derived from. This has also been successfully shown in WO 2012/168487 for other allergen fragments.

According to a further preferred embodiment of the present invention the polypeptide construct comprises one to ten, preferably two to eight, more preferably three to six, allergen fragments fused to the N- and/or C-terminus of the carrier protein.

The general structure of a polypeptide construct being a fusion protein as defined herein can be (A)n-(B)n-Z, (A)n-Z-(B) n, Z-(A) n-(B) n, (A) n-(B) n-(C) n-Z, (A) n-(B) n-Z-(C) n, (A) n-Z-(B) n-(C) n, Z-(A) n-(B) n-(C) n, (A) n-(B) n-(C) n-(D) n-Z, (A) n-(B) n-(C) n-Z-(D) n, (A) n-(B) n-Z-(C) n-(D) n, (A)n-Z-(B)n-(C)n-(D)n, Z-(A)n-(B)n-(C) n-(D)n, (A)n-(B)n-(C)n-(D)n-(E)n-Z, (A)n-(B)n-(C)n-(D)n-Z-(E)n, (A)n-(B)n-(C)n-Z-(D)n-(E)n, (A)n-(B)n-Z-(C)n-(D) n-(E)n, (A)n-Z-(B)n-(C)n-(D)n-(E)n, Z-(A)n-(B)n-(C)n-(D) n-(E)n, (A)n-(B)n-(C)n-(D)n-(E)n-(F)n-Z, (A)n-(B)n-(C)n-(D)n-(E)n-Z-(F)n, (A)n-(B)n-(C)n-(D)n-Z-(E)n-(F)n, (A)n-(B)n-(C)n-Z-(D)n-(E)n-(F)n, (A)n-(B)n-Z-(C)n-(D)n-(E)n-(F)n, (A)n-Z-(B)n-(C)n-(D)n-(E)n-(F)n, Z-(A)n-(B)n-(C)n-(D)n-(E)n-(F)n, etc., whereby A, B, C, and E stand for a fragment of a mature allergen derived from an allergen of the Amb a 1 family of *Ambrosia artemisiifolia* or variants of said at least two fragment sas defined herein which can be independently identical or different, Z stands for the carrier protein, preferably PreS or a fragment thereof, and n is independently an integer between one and five, preferably between one and four, more preferably between one and three, more preferably one or two, most preferably two. The most preferred structure for the fusion proteins of the present invention is (A)n-(B)n-(C)n-Z-(D)n-(E)n-(F)n, whereby fragments A, B and C are identical to fragments F, E and D, respectively. Particularly preferred are polypeptide constructs which comprise the same or different fragments in the same or different number fused to the N- and/or C-terminal end of a carrier protein.

In a particular preferred embodiment of the present invention the fusion protein comprises at the C-terminus of a carrier protein one to ten, preferably one to eight, more preferably one to six, fragments and at the N-terminus also one to ten, preferably one to eight, more preferably one to six, fragments of a mature allergen derived from an allergen of the Amb a 1 family of *Ambrosia artemisiifolia* or variants of said at least two fragments. These fragments can be different or identical. Furthermore, a fusion protein of the present invention may comprise one or more, preferably two or more, of the same fragment.

According to another preferred embodiment of the present invention the polypeptide construct comprises or consists of an amino acid sequence selected from the group consisting of SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 59, SEQ ID No. 62, SEQ ID No. 63, SEQ ID No. 64, SEQ ID No. 65, SEQ ID No. 66, SEQ ID No. 67, SEQ ID No. 68, SEQ ID No. 69, SEQ ID No. 70 and variants thereof having a sequence identity of at least 80%, preferably at least 90%, more preferably at least 95%, more preferably at least 98%, to these amino acid sequences.

According to a particularly preferred embodiment of the present invention the polypeptide construct comprises or consists of an amino acid sequence selected from the group consisting of SEQ ID No. 25, SEQ ID No. 26, SEQ ID No. 27, SEQ ID No. 59, SEQ ID No. 62 and SEQ ID No. 63.

The amino acid sequences of the preferred polypeptide constructs of the present invention are mentioned in example 3 (below) and are designated as K4, K4A, K4B, K4C, K4Cvar, K4D, K4Dvar, K4E and K4Evar. Further preferred polypeptide constructs of the present invention comprise or consist of the following amino acid sequences, whereby some of these have a His-tag (6 consecutive amino acid residues) at the N- or C-terminal end, which may allow a better purification. In principle, any of the polypeptides of the present invention can have a His-tag or not:

```
K4His (SEQ ID No. 25):
CRFGFFQVVNNNYDRWGTYAIGGSSAPTILCRFGFFQVVNNNYDRWGTYAIGGSSAPTIL

AEGVGEILPSVNETRSLQACEAYNIIDKCAEGVGEILPSVNETRSLQACEAYNIIDKCSD

PVLTPVQSAGMIPAEPGEAAIKLTSSAGVLSCSDPVLTPVQSAGMIPAEPGEAAIKLTSS

AGVLSCGGWSSKPRKGMGTNLSVPNPLGFFPDHQLDPAFGANSNNPDWDFNPIKDHWPAA

NQVGVGAFGPGLTPPHGGILGWSPQAQGILTTVSTIPPPASTNRQSGRQPTPISPPLRDS

HPQAMQWNSTAFHQALQDPRVRGLYFPAGGSSSGTVNPAPNIASHISSISARTGDPVTNS

DPVLTPVQSAGMIPAEPGEAAIKLTSSAGVLSCSDPVLTPVQSAGMIPAEPGEAAIKLTS

SAGVLSCAEGVGEILPSVNETRSLQACEAYNIIDKCAEGVGEILPSVNETRSLQACEAYN

IIDKCCRFGFFQVVNNNYDRWGTYAIGGSSAPTILCRFGFFQVVNNNYDRWGTYAIGGSS

APTILHHHHHH

K4AHis (SEQ ID No. 26):
RFGFFQVVNNNYDRWGTYAIGGSSAPTILRFGFFQVVNNNYDRWGTYAIGGSSAPTILA

EGVGEILPSVNETRSLQACEAYNIIDKAEGVGEILPSVNETRSLQACEAYNIIDKSDPV

LTPVQSAGMIPAEPGEAAIKLTSSAGVLSSDPVLTPVQSAGMIPAEPGEAAIKLTSSAG

VLSGGWSSKPRKGMGTNLSVPNPLGFFPDHQLDPAFGANSNNPDWDFNPIKDHWPAANQ

VGVGAFGPGLTPPHGGILGWSPQAQGILTTVSTIPPPASTNRQSGRQPTPISPPLRDSH

PQAMQWNSTAFHQALQDPRVRGLYFPAGGSSSGTVNPAPNIASHISSISARTGDPVTNS

DPVLTPVQSAGMIPAEPGEAAIKLTSSAGVLSSDPVLTPVQSAGMIPAEPGEAAIKLTS

SAGVLSAEGVGEILPSVNETRSLQACEAYNIIDKAEGVGEILPSVNETRSLQACEAYNI

IDKRFGFFQVVNNNYDRWGTYAIGGSSAPTILRFGFFQVVNNNYDRWGTYAIGGSSAPT

ILHHHHHH

K4BHis (SEQ ID No. 27):
SRFGFFQVVNNNYDRWGTYAIGGSSAPTILSRFGFFQVVNNNYDRWGTYAIGGSSAPTI

LAEGVGEILPSVNETRSLQASEAYNIIDKSAEGVGEILPSVNETRSLQASEAYNIIDKS

SDPVLTPVQSAGMIPAEPGEAAIKLTSSAGVLSSSDPVLTPVQSAGMIPAEPGEAAIKL

TSSAGVLSSGGWSSKPRKGMGTNLSVPNPLGFFPDHQLDPAFGANSNNPDWDFNPIKDH

WPAANQVGVGAFGPGLTPPHGGILGWSPQAQGILTTVSTIPPPASTNRQSGRQPTPISP

PLRDSHPQAMQWNSTAFHQALQDPRVRGLYFPAGGSSSGTVNPAPNIASHISSISARTG

DPVTNSDPVLTPVQSAGMIPAEPGEAAIKLTSSAGVLSSSDPVLTPVQSAGMIPAEPGE

AAIKLTSSAGVLSSAEGVGEILPSVNETRSLQASEAYNIIDKSAEGVGEILPSVNETRS

LQASEAYNIIDKSSRFGFFQVVNNNYDRWGTYAIGGSSAPTILSRFGFFQVVNNNYDRW

GTYAIGGSSAPTILHHHHHH

K4Cvar-Variant of K4C, wherein cysteine residues have
been exchanged with serine residues (SEQ ID No. 28):
SRHGFFQVVNNNYDKWGSYAIGGSASPTILSRHGFFQVVNNNYDKWGSYAIGGSASPTIL

AEDLQEILPVNETRRLTTSGAYNIIDGSAEDLQEILPVNETRRLTTSGAYNIIDGSVDPV

LTPEQSAGMIPAEPGESALSLTSSAGVLSSVDPVLTPEQSAGMIPAEPGESALSLTSSAG

VLSSGGWSSKPRKGMGTNLSVPNPLGFFPDHQLDPAFGANSNNPDWDFNPIKDHWPAANQ
```

-continued

VGVGAFGPGLTPPHGGILGWSPQAQGILTTVSTIPPPASTNRQSGRQPTPISPPLRDSHP

QAMQWNSTAFHQALQDPRVRGLYFPAGGSSSGTVNPAPNIASHISSISARTGDPVTNVDP

VLTPEQSAGMIPAEPGESALSLTSSAGVLSSVDPVLTPEQSAGMIPAEPGESALSLTSSA

GVLSSAEDLQEILPVNETRRLTTSGAYNIIDGSAEDLQEILPVNETRRLTTSGAYNIIDG

SSRHGFFQVVNNNYDKWGSYAIGGSASPTILSRHGFFQVVNNNYDKWGSYAIGGSASPTI

L

K4Dvar-Variant of K4D, wherein cysteine residues have
been exchanged with serine residues (SEQ ID No. 29):
SRHGFFQVVNNNYDKWGSYAIGGSASPTILSRHGFFQVVNNNYDKWGSYAIGGSASPTIL

AEDLQEILPVNETRRLTTSGAYNIIDGSAEDLQEILPVNETRRLTTSGAYNIIDGSVDPV

LTPEQSAGMIPAEPGESALSLTSSAGVLSSVDPVLTPEQSAGMIPAEPGESALSLTSSAG

VLSSGGWSSKPRKGMGTNLSVPNPLGFFPDHQLDPAFGANSNNPDWDFNPIKDHWPAANQ

VGVGAFGPGLTPPHGGILGWSPQAQGILTTVSTIPPPASTNRQSGRQPTPISPPLRDSHP

QAMQWNSTAFHQALQDPRVRGLYFPAGGSSSGTVNPAPNIASHISSISARTGDPVTNSDP

VLTPVQSAGMIPAEPGEAAIKLTSSAGVLSSSDPVLTPVQSAGMIPAEPGEAAIKLTSSA

GVLSSAEGVGEILPSVNETRSLQASEAYNIIDKSAEGVGEILPSVNETRSLQASEAYNII

DKSSRFGFFQVVNNNYDRWGTYAIGGSSAPTILSRFGFFQVVNNNYDRWGTYAIGGSSAP

TIL

K4Evar-Variant of K4D, wherein cysteine residues have
been exchanged with serine residues (SEQ ID No. 30):
SRHGFFQVVNNNYDKWGSYAIGGSASPTILSRFGFFQVVNNNYDRWGTYAIGGSSAPTIL

AEDLQEILPVNETRRLTTSGAYNIIDGSAEGVGEILPSVNETRSLQASEAYNIIDKSVDP

VLTPEQSAGMIPAEPGESALSLTSSAGVLSSSDPVLTPVQSAGMIPAEPGEAAIKLTSSA

GVLSSGGWSSKPRKGMGTNLSVPNPLGFFPDHQLDPAFGANSNNPDWDFNPIKDHWPAAN

QVGVGAFGPGLTPPHGGILGWSPQAQGILTTVSTIPPPASTNRQSGRQPTPISPPLRDSH

PQAMQWNSTAFHQALQDPRVRGLYFPAGGSSSGTVNPAPNIASHISSISARTGDPVTNVD

PVLTPEQSAGMIPAEPGESALSLTSSAGVLSSSDPVLTPVQSAGMIPAEPGEAAIKLTSS

AGVLSSAEDLQEILPVNETRRLTTSGAYNIIDGSAEGVGEILPSVNETRSLQASEAYNII

DKSSRHGFFQVVNNNYDKWGSYAIGGSASPTILSRFGFFQVVNNNYDRWGTYAIGGSSAP

TIL

K4F (SEQ ID No. 31):
CRFGFFQVVNNNYDRWGTYAIGGSSAPTILCRFGFFQVVNNNYDRWGTYAIGGSSAPTIL

SDPVLTPVQSAGMIPAEPGEAAIKLTSSAGVLSCSDPVLTPVQSAGMIPAEPGEAAIKLT

SSAGVLSCAEGVGEILPSVNETRSLQACEAYNIIDKCAEGVGEILPSVNETRSLQACEAY

NIIDKCGGWSSKPRKGMGTNLSVPNPLGFFPDHQLDPAFGANSNNPDWDFNPIKDHWPAA

NQVGVGAFGPGLTPPHGGILGWSPQAQGILTTVSTIPPPASTNRQSGRQPTPISPPLRDS

HPQAMQWNSTAFHQALQDPRVRGLYFPAGGSSSGTVNPAPNIASHISSISARTGDPVTNA

EGVGEILPSVNETRSLQACEAYNIIDKCAEGVGEILPSVNETRSLQACEAYNIIDKCSDP

VLTPVQSAGMIPAEPGEAAIKLTSSAGVLSCSDPVLTPVQSAGMIPAEPGEAAIKLTSSA

GVLSCCRFGFFQVVNNNYDRWGTYAIGGSSAPTILCRFGFFQVVNNNYDRWGTYAIGGSS

APTIL

K4G (SEQ ID No. 32):
SDPVLTPVQSAGMIPAEPGEAAIKLTSSAGVLSCSDPVLTPVQSAGMIPAEPGEAAIKL

TSSAGVLSCAEGVGEILPSVNETRSLQACEAYNIIDKCAEGVGEILPSVNETRSLQACE

-continued

AYNIIDKCCRFGFFQVVNNNYDRWGTYAIGGSSAPTILCRFGFFQVVNNNYDRWGTYAI
GGSSAPTILGGWSSKPRKGMGTNLSVPNPLGFFPDHQLDPAFGANSNNPDWDFNPIKDH
WPAANQVGVGAFGPGLTPPHGGILGWSPQAQGILTTVSTIPPPASTNRQSGRQPTPISP
PLRDSHPQAMQWNSTAFHQALQDPRVRGLYFPAGGSSSGTVNPAPNIASHISSISARTG
DPVTNCRFGFFQVVNNNYDRWGTYAIGGSSAPTILCRFGFFQVVNNNYDRWGTYAIGGS
SAPTILAEGVGEILPSVNETRSLQACEAYNIIDKCAEGVGEILPSVNETRSLQACEAYN
IIDKCSDPVLTPVQSAGMIPAEPGEAAIKLTSSAGVLSCSDPVLTPVQSAGMIPAEPGE
AAIKLTSSAGVLSC

K4H (SEQ ID No. 33):
SDPVLTPVQSAGMIPAEPGEAAIKLTSSAGVLSCSDPVLTPVQSAGMIPAEPGEAAIKL
TSSAGVLSCSDPVLTPVQSAGMIPAEPGEAAIKLTSSAGVLSCSDPVLTPVQSAGMIPA
EPGEAAIKLTSSAGVLSCCRFGFFQVVNNNYDRWGTYAIGGSSAPTILCRFGFFQVVNN
NYDRWGTYAIGGSSAPTILCRFGFFQVVNNNYDRWGTYAIGGSSAPTILCRFGFFQVVN
NNYDRWGTYAIGGSSAPTILGGWSSKPRKGMGTNLSVPNPLGFFPDHQLDPAFGANSNN
PDWDFNPIKDHWPAANQVGVGAFGPGLTPPHGGILGWSPQAQGILTTVSTIPPPASTNR
QSGRQPTPISPPLRDSHPQAMQWNSTAFHQALQDPRVRGLYFPAGGSSSGTVNPAPNIA
SHISSISARTGDPVTNAEGVGEILPSVNETRSLQACEAYNIIDKCAEGVGEILPSVNET
RSLQACEAYNIIDKCAEGVGEILPSVNETRSLQACEAYNIIDKCAEGVGEILPSVNETR
SLQACEAYNIIDKC

K4I (SEQ ID No. 34):
SDPVLTPVQSAGMIPAEPGEAAIKLTSSAGVLSCSDPVLTPVQSAGMIPAEPGEAAIKL
TSSAGVLSCSDPVLTPVQSAGMIPAEPGEAAIKLTSSAGVLSCCRFGFFQVVNNNYDRW
GTYAIGGSSAPTILCRFGFFQVVNNNYDRWGTYAIGGSSAPTILCRFGFFQVVNNNYDR
WGTYAIGGSSAPTILGGWSSKPRKGMGTNLSVPNPLGFFPDHQLDPAFGANSNNPDWDF
NPIKDHWPAANQVGVGAFGPGLTPPHGGILGWSPQAQGILTTVSTIPPPASTNRQSGRQ
PTPISPPLRDSHPQAMQWNSTAFHQALQDPRVRGLYFPAGGSSSGTVNPAPNIASHISS
ISARTGDPVTNAEGVGEILPSVNETRSLQACEAYNIIDKCAEGVGEILPSVNETRSLQA
CEAYNIIDKCAEGVGEILPSVNETRSLQACEAYNIIDKC

K4J (SEQ ID No. 35):
SDPVLTPVQSAGMIPAEPGEAAIKLTSSAGVLSSSDPVLTPVQSAGMIPAEPGEAAIKL
TSSAGVLSSSDPVLTPVQSAGMIPAEPGEAAIKLTSSAGVLSSSRFGFFQVVNNNYDRW
GTYAIGGSSAPTILSRFGFFQVVNNNYDRWGTYAIGGSSAPTILSRFGFFQVVNNNYDR
WGTYAIGGSSAPTILGGWSSKPRKGMGTNLSVPNPLGFFPDHQLDPAFGANSNNPDWDF
NPIKDHWPAANQVGVGAFGPGLTPPHGGILGWSPQAQGILTTVSTIPPPASTNRQSGRQ
PTPISPPLRDSHPQAMQWNSTAFHQALQDPRVRGLYFPAGGSSSGTVNPAPNIASHISS
ISARTGDPVTNAEGVGEILPSVNETRSLQASEAYNIIDKSAEGVGEILPSVNETRSLQA
SEAYNIIDKSAEGVGEILPSVNETRSLQASEAYNIIDKS

K4CHis (SEQ ID No. 36):
CRHGFFQVVNNNYDKWGSYAIGGSASPTILCRHGFFQVVNNNYDKWGSYAIGGSASPTI
LAEDLQEILPVNETRRLTTSGAYNIIDGCAEDLQEILPVNETRRLTTSGAYNIIDGCVD
PVLTPEQSAGMIPAEPGESALSLTSSAGVLSCVDPVLTPEQSAGMIPAEPGESALSLTS
SAGVLSCGGWSSKPRKGMGTNLSVPNPLGFFPDHQLDPAFGANSNNPDWDFNPIKDHWP

-continued

AANQVGVGAFGPGLTPPHGGILGWSPQAQGILTTVSTIPPPASTNRQSGRQPTPISPPL

RDSHPQAMQWNSTAFHQALQDPRVRGLYFPAGGSSSGTVNPAPNIASHISSISARTGDP

VTNVDPVLTPEQSAGMIPAEPGESALSLTSSAGVLSCVDPVLTPEQSAGMIPAEPGESA

LSLTSSAGVLSCAEDLQEILPVNETRRLTTSGAYNIIDGCAEDLQEILPVNETRRLTTS

GAYNIIDGCCRHGFFQVVNNNYDKWGSYAIGGSASPTILCRHGFFQVVNNNYDKWGSYA

IGGSASPTILHHHHHH

K4K (SEQ ID No. 37):
LRHGFVQVVNNNYERWGSYALGGSAGPTILLRHGFVQVVNNNYERWGSYALGGSAGPTI

LAEDLQQILPSANETRSLTTCGTYNIIDGCAEDLQQILPSANETRSLTTCGTYNIIDGC

VDPVLTPEQNAGMIPAEPGEAVLRLTSSAGVLSCVDPVLTPEQNAGMIPAEPGEAVLRL

ISSAGVLSCGGWSSKPRKGMGTNLSVPNPLGFFPDHQLDPAFGANSNNPDWDFNPIKDH

WPAANQVGVGAFGPGLTPPHGGILGWSPQAQGILTTVSTIPPPASTNRQSGRQPTPISP

PLRDSHPQAMQWNSTAFHQALQDPRVRGLYFPAGGSSSGTVNPAPNIASHISSISARTG

DPVTNVDPVLTPEQNAGMIPAEPGEAVLRLTSSAGVLSCVDPVLTPEQNAGMIPAEPGE

AVLRLTSSAGVLSCAEDLQQILPSANETRSLTTCGTYNIIDGCAEDLQQILPSANETRS

LTTCGTYNIIDGCLRHGFVQVVNNNYERWGSYALGGSAGPTILLRHGFVQVVNNNYERW

GSYALGGSAGPTIL

K4L (SEQ ID No. 38):
LRHGFVQVVNNNYERWGSYALGGSAGPTILLRHGFVQVVNNNYERWGSYALGGSAGPTI

LAEDLQQILPSANETRSLTTSGTYNIIDGSAEDLQQILPSANETRSLTTSGTYNIIDGS

VDPVLTPEQNAGMIPAEPGEAVLRLTSSAGVLSSVDPVLTPEQNAGMIPAEPGEAVLRL

ISSAGVLSSGGWSSKPRKGMGTNLSVPNPLGFFPDHQLDPAFGANSNNPDWDFNPIKDH

WPAANQVGVGAFGPGLTPPHGGILGWSPQAQGILTTVSTIPPPASTNRQSGRQPTPISP

PLRDSHPQAMQWNSTAFHQALQDPRVRGLYFPAGGSSSGTVNPAPNIASHISSISARTG

DPVTNVDPVLTPEQNAGMIPAEPGEAVLRLTSSAGVLSSVDPVLTPEQNAGMIPAEPGE

AVLRLTSSAGVLSSAEDLQQILPSANETRSLTTSGTYNIIDGSAEDLQQILPSANETRS

LTTSGTYNIIDGSLRHGFVQVVNNNYERWGSYALGGSAGPTILLRHGFVQVVNNNYERW

GSYALGGSAGPTIL

K4M (SEQ ID No. 39):
CRFGFFQVVNNNYDRWGTYAIGGSSAPTILCRFGFFQVVNNNYDRWGTYAIGGSSAPTI

LAEDVEEFLPSANETRRSLKACEAHNIIDKCAEDVEEFLPSANETRRSLKACEAHNIID

KCSDPVLTPEQKAGMIPAEPGEAVLRLTSSAGVLSCSDPVLTPEQKAGMIPAEPGEAVL

RLTSSAGVLSCGGWSSKPRKGMGTNLSVPNPLGFFPDHQLDPAFGANSNNPDWDFNPIK

DHWPAANQVGVGAFGPGLTPPHGGILGWSPQAQGILTTVSTIPPPASTNRQSGRQPTPI

SPPLRDSHPQAMQWNSTAFHQALQDPRVRGLYFPAGGSSSGTVNPAPNIASHISSISAR

TGDPVTNSDPVLTPEQKAGMIPAEPGEAVLRLTSSAGVLSCSDPVLTPEQKAGMIPAEP

GEAVLRLTSSAGVLSCAEDVEEFLPSANETRRSLKACEAHNIIDKCAEDVEEFLPSANE

TRRSLKACEAHNIIDKCCRFGFFQVVNNNYDRWGTYAIGGSSAPTILCRFGFFQVVNNN

YDRWGTYAIGGSSAPTIL

K4N (SEQ ID No. 40):
SRFGFFQVVNNNYDRWGTYAIGGSSAPTILSRFGFFQVVNNNYDRWGTYAIGGSSAPTI

LAEDVEEFLPSANETRRSLKASEAHNIIDKSAEDVEEFLPSANETRRSLKACEAHNIID

KSSDPVLTPEQKAGMIPAEPGEAVLRLTSSAGVLSSSDPVLTPEQKAGMIPAEPGEAVL

-continued

RLTSSAGVLSSGGWSSKPRKGMGTNLSVPNPLGFFPDHQLDPAFGANSNNPDWDFNPIK
DHWPAANQVGVGAFGPGLTPPHGGILGWSPQAQGILTTVSTIPPPASTNRQSGRQPTPI
SPPLRDSHPQAMQWNSTAFHQALQDPRVRGLYFPAGGSSSGTVNPAPNIASHISSISAR
TGDPVTNSDPVLTPEQKAGMIPAEPGEAVLRLTSSAGVLSSSDPVLTPEQKAGMIPAEP
GEAVLRLTSSAGVLSSAEDVEEFLPSANETRRSLKASEAHNIIDKSAEDVEEFLPSANE
TRRSLKASEAHNIIDKSSRFGFFQVVNNNYDRWGTYAIGGSSAPTILSRFGFFQVVNNN
YDRWGTYAIGGSSAPTIL

K40 (SEQ ID No. 41):
PLWIIFKNDMVINLNQELVVNSDKTIDGRGPLWIIFKNDMVINLNQELVVNSDKTIDGR
GPLWIIFKNDMVINLNQELVVNSDKTIDGRGSDPVLTPVQSAGMIPAEPGEAAIKLTSS
AGVLSCSDPVLTPVQSAGMIPAEPGEAAIKLTSSAGVLSCSDPVLTPVQSAGMIPAEPG
EAAIKLTSSAGVLSCGGWSSKPRKGMGTNLSVPNPLGFFPDHQLDPAFGANSNNPDWDF
NPIKDHWPAANQVGVGAFGPGLTPPHGGILGWSPQAQGILTTVSTIPPPASTNRQSGRQ
PTPISPPLRDSHPQAMQWNSTAFHQALQDPRVRGLYFPAGGSSSGTVNPAPNIASHISS
ISARTGDPVTCRFGFFQVVNNNYDRWGTYAIGGSSAPTILCRFGFFQVVNNNYDRWGTY
AIGGSSAPTILCRFGFFQVVNNNYDRWGTYAIGGSSAPTILAEGVGEILPSVNETRSLQ
ACEAYNIIDKCAEGVGEILPSVNETRSLQACEAYNIIDKCAEGVGEILPSVNETRSLQA
CEAYNIIDKC

K4P (SEQ ID No. 42):
PLWIIFKNDMVINLNQELVVNSDKTIDGRGPLWIIFKNDMVINLNQELVVNSDKTIDGR
GPLWIIFKNDMVINLNQELVVNSDKTIDGRGCRFGFFQVVNNNYDRWGTYAIGGSSAPT
ILCRFGFFQVVNNNYDRWGTYAIGGSSAPTILCRFGFFQVVNNNYDRWGTYAIGGSSAP
TILGGWSSKPRKGMGTNLSVPNPLGFFPDHQLDPAFGANSNNPDWDFNPIKDHWPAANQ
VGVGAFGPGLTPPHGGILGWSPQAQGILTTVSTIPPPASTNRQSGRQPTPISPPLRDSH
PQAMQWNSTAFHQALQDPRVRGLYFPAGGSSSGTVNPAPNIASHISSISARTGDPVTSD
PVLTPVQSAGMIPAEPGEAAIKLTSSAGVLSCSDPVLTPVQSAGMIPAEPGEAAIKLTS
SAGVLSCSDPVLTPVQSAGMIPAEPGEAAIKLTSSAGVLSCAEGVGEILPSVNETRSLQ
ACEAYNIIDKCAEGVGEILPSVNETRSLQACEAYNIIDKCAEGVGEILPSVNETRSLQA
CEAYNIIDKC

K4Q (SEQ ID No. 43):
SRHGFFQVVNNNYDKWGSYAIGGSASPTILSRFGFFQVVNNNYDRWGTYAIGGSSAPTI
LAEDLQEILPVNETRRLTTSGAYNIIDGSAEDVEEFLPSANETRRSLKACEAHNIIDKC
VDPVLTPEQSAGMIPAEPGESALSLTSSAGVLSSSDPVLTPEQKAGMIPAEPGEAVLRL
ISSAGVLSCGGWSSKPRKGMGTNLSVPNPLGFFPDHQLDPAFGANSNNPDWDFNPIKDH
WPAANQVGVGAFGPGLTPPHGGILGWSPQAQGILTTVSTIPPPASTNRQSGRQPTPISP
PLRDSHPQAMQWNSTAFHQALQDPRVRGLYFPAGGSSSGTVNPAPNIASHISSISARTG
DPVTNSDPVLTPVQSAGMIPAEPGEAAIKLTSSAGVLSCVDPVLTPEQNAGMIPAEPGE
AVLRLTSSAGVLSCAEGVGEILPSVNETRSLQACEAYNIIDKCAEDLQQILPSANETRS
LTTCGTYNIIDGCCRFGFFQVVNNNYDRWGTYAIGGSSAPTILLRHGFVQVVNNNYERW
GSYALGGSAGPTIL

K4R (SEQ ID No. 44):
SRHGFFQVVNNNYDKWGSYAIGGSASPTILSRFGFFQVVNNNYDRWGTYAIGGSSAPTI
LAEDLQEILPVNETRRLTTSGAYNIIDGSAEDVEEFLPSANETRRSLKACEAHNIIDKS
VDPVLTPEQSAGMIPAEPGESALSLTSSAGVLSSSDPVLTPEQKAGMIPAEPGEAVLRL
ISSAGVLSSGGWSSKPRKGMGTNLSVPNPLGFFPDHQLDPAFGANSNNPDWDFNPIKDH
WPAANQVGVGAFGPGLTPPHGGILGWSPQAQGILTTVSTIPPPASTNRQSGRQPTPISP
PLRDSHPQAMQWNSTAFHQALQDPRVRGLYFPAGGSSSGTVNPAPNIASHISSISARTG
DPVTNSDPVLTPVQSAGMIPAEPGEAAIKLTSSAGVLSSVDPVLTPEQNAGMIPAEPGE
AVLRLTSSAGVLSSAEGVGEILPSVNETRSLQASEAYNIIDKSAEDLQQILPSANETRS
LTTSGTYNIIDGSSRFGFFQVVNNNYDRWGTYAIGGSSAPTILLRHGFVQVVNNNYERW
GSYALGGSAGPTIL

K4S (SEQ ID No. 67):
AEDLQEILPVNETRRLTTSGAYNIIDGCCRHGFFQVVNNNYDKWGSYAIGGSASPTILC
RHGFFQVVNNNYDKWGSYAIGGSASPTILAEDLQEILPVNETRRLTTSGAYNIIDGCAE
DLQEILPVNETRRLTTSGAYNIIDGCVDPVLTPEQSAGMIPAEPGESALSLTSSAGVLS
CVDPVLTPEQSAGMIPAEPGESALSLTSSAGVLSCGGWSSKPRKGMGTNLSVPNPLGFF
PDHQLDPAFGANSNNPDWDFNPIKDHWPAANQVGVGAFGPGLTPPHGGILGWSPQAQGI
LTTVSTIPPPASTNRQSGRQPTPISPPLRDSHPQAMQWNSTAFHQALQDPRVRGLYFPA
GGSSSGTVNPAPNIASHISSISARTGDPVTNVDPVLTPEQSAGMIPAEPGESALSLTSS
AGVLSCVDPVLTPEQSAGMIPAEPGESALSLTSSAGVLSCAEDLQEILPVNETRRLTTS
GAYNIIDGCAEDLQEILPVNETRRLTTSGAYNIIDGCCRHGFFQVVNNNYDKWGSYAIG
GSASPTILCRHGFFQVVNNNYDKWGSYAIGGSASPTILAEDLQEILPVNETRRLTTSGA
YNIIDGC

K4SHis (SEQ ID No. 68):
AEDLQEILPVNETRRLTTSGAYNIIDGCCRHGFFQVVNNNYDKWGSYAIGGSASPTILC
RHGFFQVVNNNYDKWGSYAIGGSASPTILAEDLQEILPVNETRRLTTSGAYNIIDGCAE
DLQEILPVNETRRLTTSGAYNIIDGCVDPVLTPEQSAGMIPAEPGESALSLTSSAGVLS
CVDPVLTPEQSAGMIPAEPGESALSLTSSAGVLSCGGWSSKPRKGMGTNLSVPNPLGFF
PDHQLDPAFGANSNNPDWDFNPIKDHWPAANQVGVGAFGPGLTPPHGGILGWSPQAQGI
LTTVSTIPPPASTNRQSGRQPTPISPPLRDSHPQAMQWNSTAFHQALQDPRVRGLYFPA
GGSSSGTVNPAPNIASHISSISARTGDPVTNVDPVLTPEQSAGMIPAEPGESALSLTSS
AGVLSCVDPVLTPEQSAGMIPAEPGESALSLTSSAGVLSCAEDLQEILPVNETRRLTTS
GAYNIIDGCAEDLQEILPVNETRRLTTSGAYNIIDGCCRHGFFQVVNNNYDKWGSYAIG
GSASPTILCRHGFFQVVNNNYDKWGSYAIGGSASPTILAEDLQEILPVNETRRLTTSGA
YNIIDGCHHHHHH

K4T (SEQ ID No. 69):
AEDLQEILPVNETRRLTTSGAYNIIDGSSRHGFFQVVNNNYDKWGSYAIGGSASPTILS
RHGFFQVVNNNYDKWGSYAIGGSASPTILAEDLQEILPVNETRRLTTSGAYNIIDGSAE
DLQEILPVNETRRLTTSGAYNIIDGSVDPVLTPEQSAGMIPAEPGESALSLTSSAGVLS
SVDPVLTPEQSAGMIPAEPGESALSLTSSAGVLSSGGWSSKPRKGMGTNLSVPNPLGFF
PDHQLDPAFGANSNNPDWDFNPIKDHWPAANQVGVGAFGPGLTPPHGGILGWSPQAQGI
LTTVSTIPPPASTNRQSGRQPTPISPPLRDSHPQAMQWNSTAFHQALQDPRVRGLYFPA

-continued
```
GGSSSGTVNPAPNIASHISSISARTGDPVTNVDPVLTPEQSAGMIPAEPGESALSLTSS

AGVLSSVDPVLTPEQSAGMIPAEPGESALSLTSSAGVLSSAEDLQEILPVNETRRLTTS

GAYNIIDGSAEDLQEILPVNETRRLTTSGAYNIIDGSSRHGFFQVVNNNYDKWGSYAIG

GSASPTILSRHGFFQVVNNNYDKWGSYAIGGSASPTILAEDLQEILPVNETRRLTTSGA

YNIIDGS

K4THis (SEQ ID No. 70):
AEDLQEILPVNETRRLTTSGAYNIIDGSSRHGFFQVVNNNYDKWGSYAIGGSASPTILS

RHGFFQVVNNNYDKWGSYAIGGSASPTILAEDLQEILPVNETRRLTTSGAYNIIDGSAE

DLQEILPVNETRRLTTSGAYNIIDGSVDPVLTPEQSAGMIPAEPGESALSLTSSAGVLS

SVDPVLTPEQSAGMIPAEPGESALSLTSSAGVLSSGGWSSKPRKGMGTNLSVPNPLGFF

PDHQLDPAFGANSNNPDWDFNPIKDHWPAANQVGVGAFGPGLTPPHGGILGWSPQAQGI

LTTVSTIPPPASTNRQSGRQPTPISPPLRDSHPQAMQWNSTAFHQALQDPRVRGLYFPA

GGSSSGTVNPAPNIASHISSISARTGDPVTNVDPVLTPEQSAGMIPAEPGESALSLTSS

AGVLSSVDPVLTPEQSAGMIPAEPGESALSLTSSAGVLSSAEDLQEILPVNETRRLTTS

GAYNIIDGSAEDLQEILPVNETRRLTTSGAYNIIDGSSRHGFFQVVNNNYDKWGSYAIG

GSASPTILSRHGFFQVVNNNYDKWGSYAIGGSASPTILAEDLQEILPVNETRRLTTSGA

YNIIDGSHHHHHH
```

According to a particular preferred embodiment of the present invention the polypeptide construct of the present invention is used in the prevention or treatment of a ragweed pollen allergy, preferably caused by an allergen derived from an allergen of the Amb a 1 family of *Ambrosia artemisiifolia*.

Another aspect of the present invention relates to a nucleic acid molecule encoding a polypeptide construct as defined herein, wherein the at least two fragments are fused to a carrier protein.

The nucleic acid molecule of the present invention can be an RNA or a DNA molecule. The nucleic acid molecule may be part of a vector (e.g. protein expression vector, integration vector, cloning vector) which can be transfected or introduced in any kind of biological cell. Preferred cells include bacterial cells such as *Escherichia coli*, yeast cells such as *Pichia pastoris* or *Saccharomyces cerevisiae*, plant cells, mammal cells and insect cells. Means and methods for obtaining such nucleic acid molecules, vectors and cells are well known to the person skilled in the art.

A further aspect of the present invention relates to a vector comprising a nucleic acid molecule according to the present invention.

According to a preferred embodiment of the present invention said vector is an expression or a cloning vector.

According to a further preferred embodiment of the present invention said vector is a bacterial, fungal, insect, viral or mammalian vector.

The vector of the present invention may preferably be employed for cloning and expression purposes in various hosts like bacteria, yeasts, filamentous fungi, mammalian cells, insect cells, plant cells or any other prokaryotic or eukaryotic cells. Therefore, said vector comprises besides a nucleic acid encoding for a hypoallergenic molecule or fusion protein according to the present invention host specific regulatory sequences.

Another aspect of the present invention relates to a host cell comprising a nucleic acid molecule or a vector according to the present invention.

A further aspect of the present invention relates to a vaccine formulation comprising at least one polypeptide construct, a nucleic acid molecule or a vector according to the present invention.

According to a preferred embodiment of the present invention the vaccine formulation as well as the polypeptide construct described herein is used in the treatment or prevention of a ragweed pollen allergy.

The terms "preventing" and "prevention", as used herein, refer to the prevention or inhibition of the recurrence, onset and development of an allergy or a symptom thereof in a subject resulting from the administration of the polypeptide construct or pharmaceutical preparation according to the present invention. In some embodiments "preventing" and "prevention" refers to the reduction of the risk to develop an allergy against specific allergens. The term "preventing" covers measures not only to prevent the occurrence of an allergy, but also to arrest its progress and reduce its consequences once established.

The terms "treatment" and "treating", as used herein, refer to the reduction or inhibition of the progression and duration of an allergy, the reduction or amelioration of the severity of the allergy and the amelioration of one or more symptoms thereof. "Treatment" encompasses also the improvement and/or reversal of the symptoms of an allergy or allergic reactions. A polypeptide construct which causes an improvement in any parameter associated with allergy may be identified as a therapeutic fusion protein or conjugate. The term "treatment" refers to both therapeutic treatment and prophylactic measures. For example, those who may benefit from treatment with compositions and methods of the present invention include those already with an allergy as well as those in which the allergy is to be prevented.

According to a further preferred embodiment of the present invention said formulation comprises 10 ng to 1 g, preferably 100 ng to 10 mg, especially 0.5 µg to 200 µg of said polypeptide, nucleic acid molecule or vector.

According to a particularly preferred embodiment of the present invention the polypeptide construct of the present invention is administered to an individual at least once in an amount of 0.01 µg/kg body weight to 5 mg/kg body weight, preferably 0.1 µg/kg body weight to 2 mg/kg body weight. According to further preferred embodiment of the present invention the polypeptide construct is administered to a patient in an amount of 5 to 100 µg, preferably 10 to 80 µg, more preferably 15 to 30 µg, either independent from the body weight (i.e. a dose may comprise 15, 20, 25, 30, or 80 µg) or per kg body weight.

The amount of polypeptide construct that may be combined with excipients to produce a single dosage form will vary depending upon the host treated and the particular mode of administration. The dose of the polypeptide construct may vary according to factors such as the disease state, age, sex and weight of the individual, and the ability to elicit the desired antibody response in the individual. Dosage regime may be adjusted to provide the optimum therapeutic response. For example, several divided doses may be administered daily or the dose may be proportionally reduced as indicated by the exigencies of the therapeutic situation. The dose of the polypeptide construct may also be varied to provide optimum preventative dose response depending upon the circumstances. For instance, the polypeptide construct of the present invention may be administered to an individual at intervals of several days, one or two weeks or even months depending always on the level of Amb a 1 specific IgG induction.

In a preferred embodiment of the present invention the polypeptide construct and the vaccine formulation of the present invention are applied between 2 and 10, preferably between 2 and 7, even more preferably up to 5 and most preferably up to 3 times. In a particularly preferred embodiment the time interval between the subsequent vaccinations is chosen to be between 2 weeks and 5 years, preferably between 1 month and up to 3 years, more preferably between 2 months and 1.5 years. The repeated administration of the fusion protein of the present invention may maximize the final effect of the treatment.

According to another preferred embodiment of the present invention said formulation further comprises at least one adjuvant, pharmaceutical acceptable excipient and/or preservative.

The polypeptide construct and the vaccine formulation of the present invention can be administrated subcutaneously, intramuscularly, intravenously, mucosally etc. Depending on the dosage form and administration route the polypeptide construct of the present invention may be combined with excipients, diluents, adjuvants and/or carriers. A preferred adjuvant is aluminum hydroxide. Suitable protocols for the production of vaccine formulations are known to the person skilled in the art and can be found e.g. in "Vaccine Protocols" (A. Robinson, M. P. Cranage, M. Hudson; Humana Press Inc., U.S.; 2nd edition 2003).

The polypeptide construct of the present invention may be formulated also with other adjuvants regularly used in vaccines. For instance, suitable adjuvants may be MF59, aluminum phosphate, calcium phosphate, cytokines (e.g. IL-2, IL-12, GM-CSF), saponins (e.g. QS21), MDP derivatives, CpG oligonucleotides, LPS, MPL, polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes. Suitable adjuvants are commercially available as, for example, AS01B (MPL and QS21 in a liposome formulation), AS02A, AS15, AS-2, AS-03 and derivatives thereof (GlaxoSmithKline, USA); CWS (cell-wall skeleton), TDM (trehalose-6,6'-dimycolate), LeIF (Leishmania elongation initiation factor), aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7 or -12 may also be used as adjuvants. Preferred adjuvants for use in eliciting a predominantly Th1-type response include, for example, a combination of monophosphoryl lipid A, preferably 3-O-deacylated monophosphoryl lipid A (3D-MPL), optionally with an aluminum salt. Aqueous formulations comprising monophosphoryl lipid A and a surfactant have been described in WO 98/43670.

Another preferred adjuvant is a saponin or saponin mimetics or derivatives, preferably QS21 (Aquila Biopharmaceuticals Inc.), which may be used alone or in combination with other adjuvants. For example, an enhanced system involves the combination of a monophosphoryl lipid A and saponin derivative, such as the combination of QS21 and 3D-MPL. Other preferred formulations comprise an oil-in-water emulsion and tocopherol. A particularly potent adjuvant formulation is QS21, 3D-MPL and tocopherol in an oil-in-water emulsion. Additional saponin adjuvants for use in the present invention include QS7 (described in WO 96/33739 and WO 96/11711) and QS17 (described in U.S. Pat. No. 5,057,540 and EP 0 362 279 B1).

The vaccine formulation of the present invention comprises most preferably alum as adjuvant.

The present invention is further illustrated by the following figures and examples, however, without being restricted thereto.

EXAMPLES

Methods:

I) ELISA Methods Used to Test and Characterize Amb a 1 Fragments of Example 1 and Fusion Proteins of Examples 3, and 4

(a) IgE ELISA to Test the IgE Reactivity of Amb a 1 Fragments and Fusion Proteins:

The aim of this test is to evaluate whether an Amb a 1 fragment or fusion protein is hypoallergenic. For this purpose, the binding of IgE from sera of ragweed allergic individuals to the fragment or fusion protein is compared to the binding of these IgE to wild-type Amb a 1 which is used as a reference.

Wild-type Amb a 1 in the context of this application means that with respect to IgE reactivity, allergenicity, and T-cell reactivity, the Amb a 1 is essentially as occurring in the ragweed pollen. The term "wild-type Amb a 1" (also referred to as "Amb a 1"), can refer to recombinantly produced Amb a 1 (rAmb a 1), which contains a single Amb a 1 isoform, or to the natural Amb a 1 (nAmb a 1) of Example 4, which is purified from ragweed pollen and therefore comprises a variety of Amb a 1 isoforms.

The following ELISA protocol was used to test the IgE reactivity: Maxisorp ELISA plates were coated overnight at 4° C. with 0.5 µg per well of fusion-protein, Amb a 1 fragment and the reference allergen (rAmb a 1 and/or nAmb a 1), all diluted with coating puffer (3.9 g Na2CO3+5.3 g NaHCO3 in 1 L Aqua deion pH 9.6). Plates were then washed twice with 250 µL PBST, containing 0.05%

Tween20 and further blocked with blocking buffer (PBST containing 1% BSA) at 37° C. for 2 hours. Multiple patient sera from ragweed allergic patients and at least one of a non ragweed allergic patient were diluted (1:5) with dilution buffer (PBST, containing 0.5% BSA), added on the coated plates (100 µl per well) and incubated overnight at 4° C. Plates were washed five times with PBST (250 µl) and for detection 100 µl of 1:10000 diluted horseradish peroxidase-conjugated goat anti-human IgE antibody (KPL, Catalog No. 074-1004) was incubated for 2 h at 37° C. Plates were washed five times with PBST (250 µl per well). Finally 100 µL TMB (BD) was added onto the plate and the colour-reaction was stopped after 10-20 min with 50 µL 2N $H_2SO_4$ and measured at OD 450 (reference 650 nm) using a TECAN ELISA reader. Calculation of IgE reactivity in percent relative to the reference allergens.

% IgE reactivity=$(100/OD_{ref})*OD_{pat}$ $OD_{ref}$ represents the OD-value of patient's IgE bound to the reference allergen whereas the $OD_{pat}$ value represents the patients IgE bound to the tested fusion-protein or fragment.

(b) IgG ELISA to Evaluate the Induction of IgG Responses in Rabbits:

The aim of this test is to determine the in vivo immunogenicity after immunization of rabbits with fusion proteins or Amb a 1 fragments.

The following ELISA protocol was used to measure IgG levels in rabbit sera: ELISA plates were coated with 100 µL of wild-type Amb a 1 (rAmb a 1 and/or nAmb a 1) which was diluted to 2 µg per mL in 0.1 M bicarbonate buffer and incubated overnight at 4° C. Plates were washed 5 times with 250 µL PBS with 0.05% Tween 20 (PBST) using the TECAN ELISA washer and blocked with 200 µL PBST containing 1% BSA for 2 hours at RT. Then, serial dilutions of rabbit sera (dilutions prepared in PBST containing 0.5% BSA) were added to the plate (100 µL per well) and incubated overnight at 4° C. Again, plates were washed 5 times with 250 µL PBST using the TECAN ELISA washer. For the detection 100 µL of HRP labeled donkey anti-rabbit IgG detection antibody (GE Healthcare, Catalog No. NA934) diluted 1:25000 in PBST containing 0.5% BSA was added and incubated for 2 hours at 37° C. Plates were washed and finally 100 µl TMB was added onto the plate. The colour-reaction was stopped after 10-20 min with 50 µL 2N $H_2SO_4$ and measured at OD 450 (reference 650 nm) with a TECAN ELISA reader.

(c) IgE Inhibition ELISA for Detection of Blocking Antibodies in Rabbit Sera

It is desirable that an allergy vaccine induces blocking antibodies upon immunization. Aim of this test is to study the ability of IgG induced by immunization with the different fusion proteins or Amb a 1 fragments to function as blocking antibodies, thus inhibiting the interaction of IgE present in the serum of ragweed allergic individuals with wild-type Amb a 1.

The following inhibition ELISA protocol was used:

First, Maxisorp ELISA plates were coated for 2 h at 37° C. with 0.2 µg per well of wild-type Amb a 1 (nAmb a 1 and/or rAmb a 1) in 0.1 M bicarbonate buffer. Plates were washed twice with 250 µL PBS with 0.05% Tween 20 (PBST) using the TECAN ELISA washer and blocked for 2 h at 37° C. with 200 µL PBST containing 1% BSA.

In a second step, 100 µl of the rabbit sera obtained by immunization with fusion proteins, Amb a 1 fragments, or wild-type Amb a 1 (as control), and 100 µL of the corresponding preimmune sera were incubated with the coated plate overnight at 4° C. The rabbit sera were applied in different dilutions ranging from 1:10-1:100 in PBST 0.5% BSA. Mixes of anti-peptide sera were applied without further dilution. Plates were washed five times with 250 µl PBST.

In a third step, the plates were incubated with 100 µL of sera from patients with ragweed allergy (diluted 1:5 in PBST containing 0.5% BSA) for 2 h at 37° C.

Finally, bound human IgE antibodies were detected with 100 µL 1:10000 diluted (in PBST 0.5% BSA) HRP labeled goat anti-human IgE detection antibody (KPL, Catalog No. 074-1004) which was incubated for 2 hours at 37° C. Plates were washed 5 times with PBST. 100 µL TMB (BD) was added onto the plate and the colour-reaction was stopped after 10-20 min with 50 µL 2N $H_2SO_4$ and measured at OD 450 (reference 650 nm) with TECAN ELISA reader.

The inhibition rate of IgE binding in percentage was calculated according to the following formula:

IgE inhibition %=100−(ODs/ODp)×100 (according to Chen et al. Allergy Eur. J. Allergy Clin. Immunol. 67, 609-621 (2012)). ODs and ODp represent the extinctions after preincubation with the rabbit immune serum (ODs) and preimmune serum (ODp), respectively.

II) Basophil Activation Assay (BAT)

100 µl whole blood samples from ragweed allergic individuals were mixed with 20 µl of different stimuli (positive control (anti-IgE), positive control (fMLP), Amb a 1 and fusion proteins) diluted in Hepes Calcium Buffer containing 2 ng/ml IL-3 and incubated 15 min at 37° C. 10 µl Hepes/EDTA buffer was added and after 5 min incubation at RT 20 µl antibody solution (FACS-buffer, anti-CD63-PE, anti-CD123-FITC and anti-CCR3-APC) was added and incubated for 15 min in the dark. After lysing the erythrocytes and centrifugation the cells were solved in 0.5 ml FACS-buffer, centrifuged and fixed with 250 µl FACS-buffer containing 2% formaldehyde and measured with flow cytometry. The gates were set for $CD123^+/CCR3^+$ and 1000 cells were recorded.

Example 1: Design of Amb a 1.0305 Peptides

The following fragments have been designed. The indicated amino acid positions refer to the sequence of the mature Amb a 1.0305 (see FIG. 1).

| Peptide/ Fragment No. | AA Position | Sequence | SEQ ID No. |
|---|---|---|---|
| 1 | 1-29 | AEGVGEILPSVNETRSLQACEAYNIIDKC | 45 |
| 2 | 30-59 | WRGKADWENNRQALADCAQGFAKGTYGGKWC | 46 |
| 3 | 60-89 | GDVYTVTSNLDDDVANPKEGTLRFAAAQNRC | 47 |

| Peptide/ Fragment No. | AA Position | Sequence | SEQ ID No. |
|---|---|---|---|
| 4 | 90-119 | PLWIIFKNDMVINLNQELVVNSDKTIDGRGC | 48 |
| 5 | 120-152 | VKVEIINGGLTLMNVKNIIIHNINIHDVKVLPGC | 49 |
| 6 | 153-186 | GMIKSNDGPPILRQASDGDTINVAGSSQIWIDHC | 50 |
| 7 | 192-222 | CFDGLVDVTLGSTHVTISNCKFTQQSKAILLG | 51 |
| 8 | 223-252 | CADDTHVQDKGMLATVAFNMFTDNVDQRMPR | 52 |
| 9 | 253-282 | CRFGFFQVVNNNYDRWGTYAIGGSSAPTIL | 53 |
| 10 | 283-317 | CQGNRFLAPDDQIKKNVLARTGTGAAESMAWNWRS | 54 |
| 11 | 333-366 | SDPVLTPVQSAGMIPAEPGEAAIKLTSSAGVLSC | 55 |

These peptides have been chemically synthesized and used for further testing (Examples 5-7) in order to identify allergen fragments which are suitable for the construction of polypeptides of -continued VPNPLGFFPDHQLDPAFGANSNNPDWDFNPIKDHWPAANQVGVGAFGPGLTPPHGGILG
WSPQAQGILTTVSTIPPPASTNRQSGRQPTPISPPLRDSHPQAMQWNSTAFHQALQDPR
VRGLYFPAGGSSSGTVNPAPNIASHISSISARTGDPVTNCRFGFFQVVNNNYDRWGTYA
IGGSSAPTILCRFGFFQVVNNNYDRWGTYAIGGSSAPTILCRFGFFQVVNNNYDRWGTY
AIGGSSAPTIL K4 (SEQ ID No. 59):
CRFGFFQVVNNNYDRWGTYAIGGSSAPTILCRFGFFQVVNNNYDRWGTYAIGGSSAPTI
LAEGVGEILPSVNETRSLQACEAYNIIDKCAEGVGEILPSVNETRSLQACEAYNIIDKC
SDPVLTPVQSAGMIPAEPGEAAIKLTSSAGVLSCSDPVLTPVQSAGMIPAEPGEAAIKL
TSSAGVLSCGGWSSKPRKGMGTNLSVPNPLGFFPDHQLDPAFGANSNNPDWDFNPIKDH
WPAANQVGVGAFGPGLTPPHGGILGWSPQAQGILTTVSTIPPPASTNRQSGRQPTPISP
PLRDSHPQAMQWNSTAFHQALQDPRVRGLYFPAGGSSSGTVNPAPNIASHISSISARTG
DPVTNSDPVLTPVQSAGMIPAEPGEAAIKLTSSAGVLSCSDPVLTPVQSAGMIPAEPGE
AAIKLTSSAGVLSCAEGVGEILPSVNETRSLQACEAYNIIDKCAEGVGEILPSVNETRS
LQACEAYNIIDKCCRFGFFQVVNNNYDRWGTYAIGGSSAPTILCRFGFFQVVNNNYDRW
GTYAIGGSSAPTIL K5 (SEQ ID No. 60):
WRGKADWENNRQALADCAQGFAKGTYGGKWWRGKADWENNRQALADCAQGFAKGTYGGKW
ADDTHVQDKGMLATVAFNMFTDNVDQRMPRADDTHVQDKGMLATVAFNMFTDNVDQRMPR
AEGVGEILPSVNETRSLQACEAYNIIDKCAEGVGEILPSVNETRSLQACEAYNIIDKCGG
WSSKPRKGMGTNLSVPNPLGFFPDHQLDPAFGANSNNPDWDFNPIKDHWPAANQVGVGAF
GPGLTPPHGGILGWSPQAQGILTTVSTIPPPASTNRQSGRQPTPISPPLRDSHPQAMQWN
STAFHQALQDPRVRGLYFPAGGSSSGTVNPAPNIASHISSISARTGDPVTNWRGKADWEN
NRQALADCAQGFAKGTYGGKWWRGKADWENNRQALADCAQGFAKGTYGGKWADDTHVQDK
GMLATVAFNMFTDNVDQRMPRADDTHVQDKGMLATVAFNMFTDNVDQRMPRAEGVGEILP
SVNETRSLQACEAYNIIDKCAEGVGEILPSVNETRSLQACEAYNIIDKC K6 (SEQ ID No. 61):
ADDTHVQDKGMLATVAFNMFTDNVDQRMPRADDTHVQDKGMLATVAFNMFTDNVDQRMPR
ADDTHVQDKGMLATVAFNMFTDNVDQRMPRSDPVLTPVQSAGMIPAEPGEAAIKLTSSAG
VLSCSDPVLTPVQSAGMIPAEPGEAAIKLTSSAGVLSCSDPVLTPVQSAGMIPAEPGEAA
IKLTSSAGVLSCGGWSSKPRKGMGTNLSVPNPLGFFPDHQLDPAFGANSNNPDWDFNPIK
DHWPAANQVGVGAFGPGLTPPHGGILGWSPQAQGILTTVSTIPPPASTNRQSGRQPTPIS
PPLRDSHPQAMQWNSTAFHQALQDPRVRGLYFPAGGSSSGTVNPAPNIASHISSISARTG
DPVTNAEGVGEILPSVNETRSLQACEAYNIIDKCAEGVGEILPSVNETRSLQACEAYNII
DKCAEGVGEILPSVNETRSLQACEAYNIIDKCCRFGFFQVVNNNYDRWGTYAIGGSSAPT
ILCRFGFFQVVNNNYDRWGTYAIGGSSAPTILCRFGFFQVVNNNYDRWGTYAIGGSSAPT
ILWRGKADWENNRQALADCAQGFAKGTYGGKWWRGKADWENNRQALADCAQGFAKGTYGG
KWWRGKADWENNRQALADCAQGFAKGTYGGKW K4A-Variant of K4 without terminal cysteine residues
of the fragments (SEQ ID No. 62):
RFGFFQVVNNNYDRWGTYAIGGSSAPTILRFGFFQVVNNNYDRWGTYAIGGSSAPTILAE
GVGEILPSVNETRSLQACEAYNIIDKAEGVGEILPSVNETRSLQACEAYNIIDKSDPVLT
PVQSAGMIPAEPGEAAIKLTSSAGVLSSDPVLTPVQSAGMIPAEPGEAAIKLTSSAGVLS -continued

```
GGWSSKPRKGMGTNLSVPNPLGFFPDHQLDPAFGANSNNPDWDFNPIKDHWPAANQVGVG

AFGPGLTPPHGGILGWSPQAQGILTTVSTIPPPASTNRQSGRQPTPISPPLRDSHPQAMQ

WNSTAFHQALQDPRVRGLYFPAGGSSSGTVNPAPNIASHISSISARTGDPVTNSDPVLTP

VQSAGMIPAEPGEAAIKLTSSAGVLSSDPVLTPVQSAGMIPAEPGEAAIKLTSSAGVLSA

EGVGEILPSVNETRSLQACEAYNIIDKAEGVGEILPSVNETRSLQACEAYNIIDKRFGFF

QVVNNNYDRWGTYAIGGSSAPTILRFGFFQVVNNNYDRWGTYAIGGSSAPTIL
```

K4B-Variant of K4, wherein cysteine residues have
been exchanged with serine residues (SEQ ID No. 63):

```
SRFGFFQVVNNNYDRWGTYAIGGSSAPTILSRFGFFQVVNNNYDRWGTYAIGGSSAPTI

LAEGVGEILPSVNETRSLQASEAYNIIDKSAEGVGEILPSVNETRSLQASEAYNIIDKS

SDPVLTPVQSAGMIPAEPGEAAIKLTSSAGVLSSSDPVLTPVQSAGMIPAEPGEAAIKL

TSSAGVLSSGGWSSKPRKGMGTNLSVPNPLGFFPDHQLDPAFGANSNNPDWDFNPIKDH

WPAANQVGVGAFGPGLTPPHGGILGWSPQAQGILTTVSTIPPPASTNRQSGRQPTPISP

PLRDSHPQAMQWNSTAFHQALQDPRVRGLYFPAGGSSSGTVNPAPNIASHISSISARTG

DPVTNSDPVLTPVQSAGMIPAEPGEAAIKLTSSAGVLSSSDPVLTPVQSAGMIPAEPGE

AAIKLTSSAGVLSSAEGVGEILPSVNETRSLQASEAYNIIDKSAEGVGEILPSVNETRS

LQASEAYNIIDKSSRFGFFQVVNNNYDRWGTYAIGGSSAPTILSRFGFFQVVNNNYDRW

GTYAIGGSSAPTIL
```

K4C (SEQ ID No. 64):

```
CRHGFFQVVNNNYDKWGSYAIGGSASPTILCRHGFFQVVNNNYDKWGSYAIGGSASPTIL

AEDLQEILPVNETRRLTTSGAYNIIDGCAEDLQEILPVNETRRLTTSGAYNIIDGCVDPV

LTPEQSAGMIPAEPGESALSLTSSAGVLSCVDPVLTPEQSAGMIPAEPGESALSLTSSAG

VLSCGGWSSKPRKGMGTNLSVPNPLGFFPDHQLDPAFGANSNNPDWDFNPIKDHWPAANQ

VGVGAFGPGLTPPHGGILGWSPQAQGILTTVSTIPPPASTNRQSGRQPTPISPPLRDSHP

QAMQWNSTAFHQALQDPRVRGLYFPAGGSSSGTVNPAPNIASHISSISARTGDPVTNVDP

VLTPEQSAGMIPAEPGESALSLTSSAGVLSCVDPVLTPEQSAGMIPAEPGESALSLTSSA

GVLSCAEDLQEILPVNETRRLTTSGAYNIIDGCAEDLQEILPVNETRRLTTSGAYNIIDG

CCRHGFFQVVNNNYDKWGSYAIGGSASPTILCRHGFFQVVNNNYDKWGSYAIGGSASP11

L
```

K4D (SEQ ID No. 65):

```
CRHGFFQVVNNNYDKWGSYAIGGSASPTILCRHGFFQVVNNNYDKWGSYAIGGSASPTIL

AEDLQEILPVNETRRLTTSGAYNIIDGCAEDLQEILPVNETRRLTTSGAYNIIDGCVDPV

LTPEQSAGMIPAEPGESALSLTSSAGVLSCVDPVLTPEQSAGMIPAEPGESALSLTSSAG

VLSCGGWSSKPRKGMGTNLSVPNPLGFFPDHQLDPAFGANSNNPDWDFNPIKDHWPAANQ

VGVGAFGPGLTPPHGGILGWSPQAQGILTTVSTIPPPASTNRQSGRQPTPISPPLRDSHP

QAMQWNSTAFHQALQDPRVRGLYFPAGGSSSGTVNPAPNIASHISSISARTGDPVTNSDP

VLTPVQSAGMIPAEPGEAAIKLTSSAGVLSCSDPVLTPVQSAGMIPAEPGEAAIKLTSSA

GVLSCAEGVGEILPSVNETRSLQACEAYNIIDKCAEGVGEILPSVNETRSLQACEAYNII

DKCCRFGFFQVVNNNYDRWGTYAIGGSSAPTILCRFGFFQVVNNNYDRWGTYAIGGSSAP

TIL
```

K4E (SEQ ID No. 66):

```
CRHGFFQVVNNNYDKWGSYAIGGSASPTILCRFGFFQVVNNNYDRWGTYAIGGSSAPTIL

AEDLQEILPVNETRRLTTSGAYNIIDGCAEGVGEILPSVNETRSLQACEAYNIIDKCVDP
```

-continued

```
VLTPEQSAGMIPAEPGESALSLTSSAGVLSCSDPVLTPVQSAGMIPAEPGEAAIKLTSSA

GVLSCGGWSSKPRKGMGTNLSVPNPLGFFPDHQLDPAFGANSNNPDWDFNPIKDHWPAAN

QVGVGAFGPGLTPPHGGILGWSPQAQGILTTVSTIPPPASTNRQSGRQPTPISPPLRDSH

PQAMQWNSTAFHQALQDPRVRGLYFPAGGSSSGTVNPAPNIASHISSISARTGDPVTNVD

PVLTPEQSAGMIPAEPGESALSLTSSAGVLSCSDPVLTPVQSAGMIPAEPGEAAIKLTSS

AGVLSCAEDLQEILPVNETRRLTTSGAYNIIDGCAEGVGEILPSVNETRSLQACEAYNII

DKCCRHGFFQVVNNNYDKWGSYAIGGSASPTILCRFGFFQVVNNNYDRWGTYAIGGSSAP

TIL
```

The nucleic acid molecules encoding said fusion proteins have been introduced in chemically competent E. coli BL21 (DE3) (Novagen, USA) via the expression vector pET-27b (+) (Merck/Novagen) using heat shock transformation. In order to facilitate purification of the recombinantly ex pressed fusion proteins, a His-tag comprising six contiguous histidine residues has been introduced at the C-terminus of the fusion proteins.

For the recombinant expression of the fusion proteins 1.25 mL of an overnight culture was inoculated in a 250 mL LB-medium containing kanamycin to reach a cell density expressed as OD (optical density) of 0.6 measured at a wavelength of 600 nm using a photometer (Eppendorf). In order to induce the expression of the fusion proteins 1 mM IPTG (isopropyl β-D-1-thiogalactopyranoside) was added to the cell culture. After 3 to 4 hours the cells were harvested by centrifugation for 20 min at 7000 rpm. The supernatant was discarded and the pellet was frozen at −20° C.

Example 3: Isolation and Purification of Fusion Proteins

The E. coli pellets of example 2 comprising the fusion proteins were dissolved in 15 mL Lysis buffer (25 mM Imidazole; 0.1% TritonX100; pH 7.4). The resulting suspensions were stirred for 20 min at room temperature. The cells were disrupted and homogenized by using a dispersing device (Ultraturrax; IKA). DNA was removed by adding 4 μL DNAse (1 mg/mL) and stirring for 10 min. DNAse activity was decreased by addition of 10 mM NaCl. The pellets comprising the fusion proteins were harvested by centrifugation.

In order to isolate the fusion proteins from the pellets, the pellets were dissolved by using denaturing buffers (pH 8) comprising either 6 M GHC1 (guanidine hydrochloride) or 8 M urea. After dissolving the pellets with one of these buffers the solution was centrifuged and the clear supernatant was contacted with a Ni-NTA matrix (Quiagen). This matrix was transferred in a polypropylene column (Quiagen) and the column washed two times with a buffer (pH 6.3) comprising 6 M GHC1 or 8 M urea. Finally, the fusion proteins were eluted from the column by applying a buffer (pH 4.5) comprising 6 M GHC1 or 8 M urea. The purification procedure was monitored by analyzing samples from various steps with SDS-PAGE.

After the isolation and purification steps the fusion proteins dissolved in a buffer comprising 6 M GHC1 or 8 M urea were dialyzed to remove GHC1 or urea.

Example 4: Isolation and Purification of Natural Amb a 1 (nAmb a 1) from Ragweed Pollen Extract For the preparation of Ragweed pollen crude extract (CE) and subsequent precipitation with ammonium sulphate a modified protocol of Hiroshi Yasueda, et al. 1983 (J ALLERGY OLIN IMMUNOL 71:77, 1983.) was used.

Briefly, pollen was obtained from Ambrosia artemisiifolia and 10 g were defatted with ether and extracted in 200 ml of 0.125 M ammonium bicarbonate (pH=8.0) at 20° C. for 48 h. After extraction, the pollen was separated from the supernatant by centrifugation (10,000×g) and was extracted in 120 ml of 0.125 M ammonium bicarbonate over a 24 h period. The combined supernatants were dialyzed against 5 mM ammonium bicarbonate and lyophilized.

Extract obtained from 10 g of dry pollen was dissolved in 30 ml of 0.05M Tris-HCl (pH 7.8) and solid ammonium sulphate was added with stirring to 80% saturation. After stirring overnight at 4° C., the precipitate was collected by centrifugation. The resulting yellow precipitate was dissolved in 10 ml of 0.02M Tris-HCl (pH 7.8) and dialyzed against the same Tris-buffer.

For purification of nAmb a 1 three chromatography steps, including 2 Anion Exchange Chromatographies (AEC I and ACE II) and one Hydrophobic Interaction Chromatography (HIC) steps were performed.

The supernatant containing the ammonium sulfate precipitate in 10 ml of 0.02M Tris-HCl (pH 7.8) was captured using cation exchange chromatography (SP Sepharose FF, GE Health Care). High molecular weight impurities were depleted because those impurities passed the column without binding. Elution of nAmb a 1 protein was performed by gradient elution and the product eluted by using buffer A (20 mM Tris-HCl, 1 mM EDTA, pH 8) and buffer B (50 mM Tris-HCl, 1 mM EDTA, pH 8). Fractions containing nAmb a 1 were pooled according to reduced SDS-PAGE analysis, resulting in 2 pools (P1 and P2). Capture pool 2 was further processed by hydrophobic interaction chromatography (Phenyl Sepharose FF).

Pool 2 from the column was mixed with 2.5 M sodium chloride, adjusted to pH 10 and loaded to the HIC column (binding mode). Elution was performed by gradient elution using a low salt buffer. The product eluted between 30% and 60% of elution buffer A (20 mM NaHCO₃, 1 mM EDTA, 2.5 M NaCL, pH 10) and buffer B (5 mM TriHCl, 1 mM EDTA, 4% Isopropanol (pH 8.0).

Fractions were pooled according to reduced SDS-PAGE analysis and the resulting HIC pool was concentrated and diafiltrated. Finally the highly purified nAmb a 1 protein was sterile filtered (0.22 μm], the protein concentration was measured by using Bradford assay, confirmed by Western blot (WB), aliquoted and frozen at 20° C.

Purified nAmb a 1 tested positive in an Immunoblot with a specific Amb a 1-reactive Antibody.

Example 5: The IgE Reactivity of Amb a 1 Fragments is Strongly Reduced Compared to Wild-Type Amb a 1

The IgE binding capacity of the eleven Amb a 1 peptides of example 1 was compared to those of the wild-type Amb a 1 (nAmb a 1 and/or rAmb a 1) by use of the IgE ELISA described under Method I(a). The resulting OD levels in this ELISA correspond to IgE levels—the higher the OD value the more IgE has been bound by the coated antigen indicating a higher IgE reactivity. In total, sera from 23 highly ragweed allergic patients and one non allergic patient (as negative control) were selected and used for testing the Amb a 1 fragments. The IgE reactivity of the peptides was compared to that of the wild-type Amb a 1 which was used as a reference for each patient and set to 100% IgE reactivity. The percentage of IgE reactivity of the fragments was then calculated in relation to those 100% for wild-type Amb a 1 for each patient. The results are summarized in FIG. 2.

Example 6: Immunization with KLH-Coupled Amb a 1 Fragments and Fusion Proteins Induces Amb a 1-Specific IgG Antibodies To evaluate the amount of Amb a 1-specific IgG antibodies and the in vivo immunogenicity of Amb a 1 fragments of Example 1 or the fusion proteins of Examples 2 and 3 and compare it to the immunogenicity of wild-type Amb a 1 (purified natural or recombinant Amb a 1) an immunization study was carried out in rabbits. For this purpose, KLH-coupled fragments, wild-type Amb a 1 (nAmb a 1 and rAmb a 1) or fusion proteins were adsorbed to aluminum hydroxide (Alum) and administered to rabbits subcutaneously. Three rabbits were immunized with each antigen. Blood samples were obtained before and after the immunization.

To evaluate the induction of Amb a 1-specific IgG titers, serial dilutions (1/10-1/1280) of the rabbit sera obtained after immunization were tested using the IgG ELISA described under Method 5(b). The level of allergen specific IgG due to immunization with wild-type Amb a 1 (nAmb a 1 and rAmb a 1) served on the one hand as a positive control and on the other hand as a reference for optimal immunogenicity. Thus the IgG levels induced by the wild-type Amb a 1 allergens were high in comparison to those induced by the pep tides. As shown in FIGS. 3A and 3B, Peptide 11 induced by far the highest amount of Amb a 1 specific IgG antibodies and exhibit therefore the highest immunogenicity, the other peptides induced lower IgG titers. The antibody levels shown in FIGS. 3A and 3B represent the average of these 3 rabbits.

Fusion proteins were used for immunization of rabbits and the resulting anti-sera were tested in the same way.

Example 7: Immunization of Rabbits with Peptides/Amb a 1 Fragments 1 to 5 and 7 to 11 of Example 1 Induce Blocking Antibodies which Inhibit Binding of Allergic Patient's IgE to Wild-Type Amb a 1

Using method Ic) as described above the IgE inhibition potential of antibodies induced by immunization with peptides/Amb a 1 fragments 1 to 5 and 7 to 11 (see example 1) and mixtures of said peptides/fragments was evaluated.

Figure 11B:
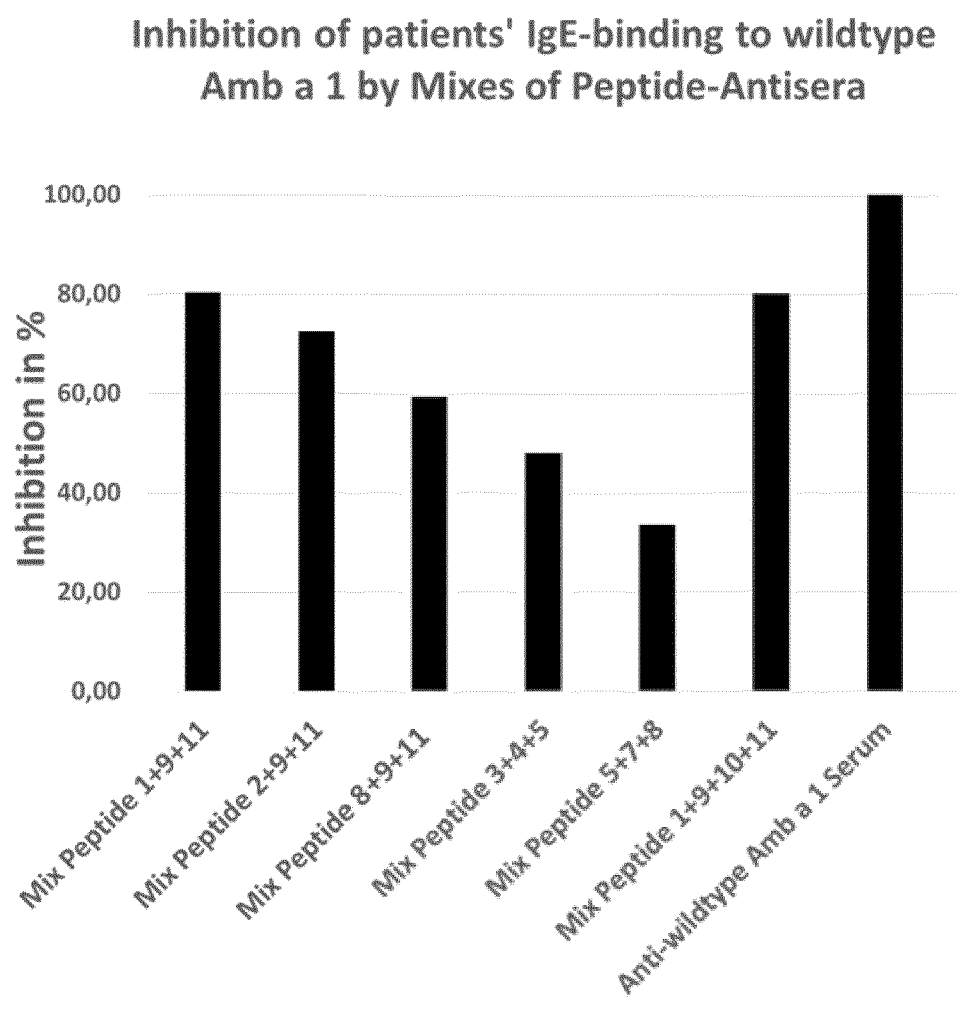

Sera obtained by immunization with the Amb a 1 peptides/fragments 1 to 5 and 7 to 11 showed that peptides/fragments 9, 10 and 11 reached a level of at least 50% IgE binding inhibition, whereas the inhibition levels obtained with peptides 1 to 5, 7 and 8 were below 50% (see FIG. 11A). Surprisingly mixtures of said sera comprising antibodies directed to three or four peptides/fragments (i.e. mixtures containing peptides 1+9+11, 2+9+11, 8+9+11, 3+4+5, 5+7+8, 1+9+10+11) revealed that mixtures containing antibodies directed to at least one fragment derived from the N-terminus of a mature allergen (i.e. amino acid residues 1 to 50 of a mature allergen) and antibodies directed to at least one fragment derived from the C-terminus of a mature allergen (i.e. amino acid residues 240 to the C-terminal end of a mature allergen) show the highest IgE inhibition reactivity (see FIG. 11B). Mixtures of sera comprising antibodies directed to two fragments of Amb a 1 (peptides/fragments 2+11, 1+2, 1+8 and 1+11) showed in IgE inhibitions assays also that a combination of antibodies directed to at least one fragment derived from the N-terminus of a mature allergen and antibodies directed to at least one fragment derived from the C-terminus of a mature allergen results in a high inhibition rate (see FIG. 11C).

Example 8: The IgE Reactivity of the Fusion Proteins is Strongly Reduced Compared to Wild-Type Amb a 1

Figure 4B:
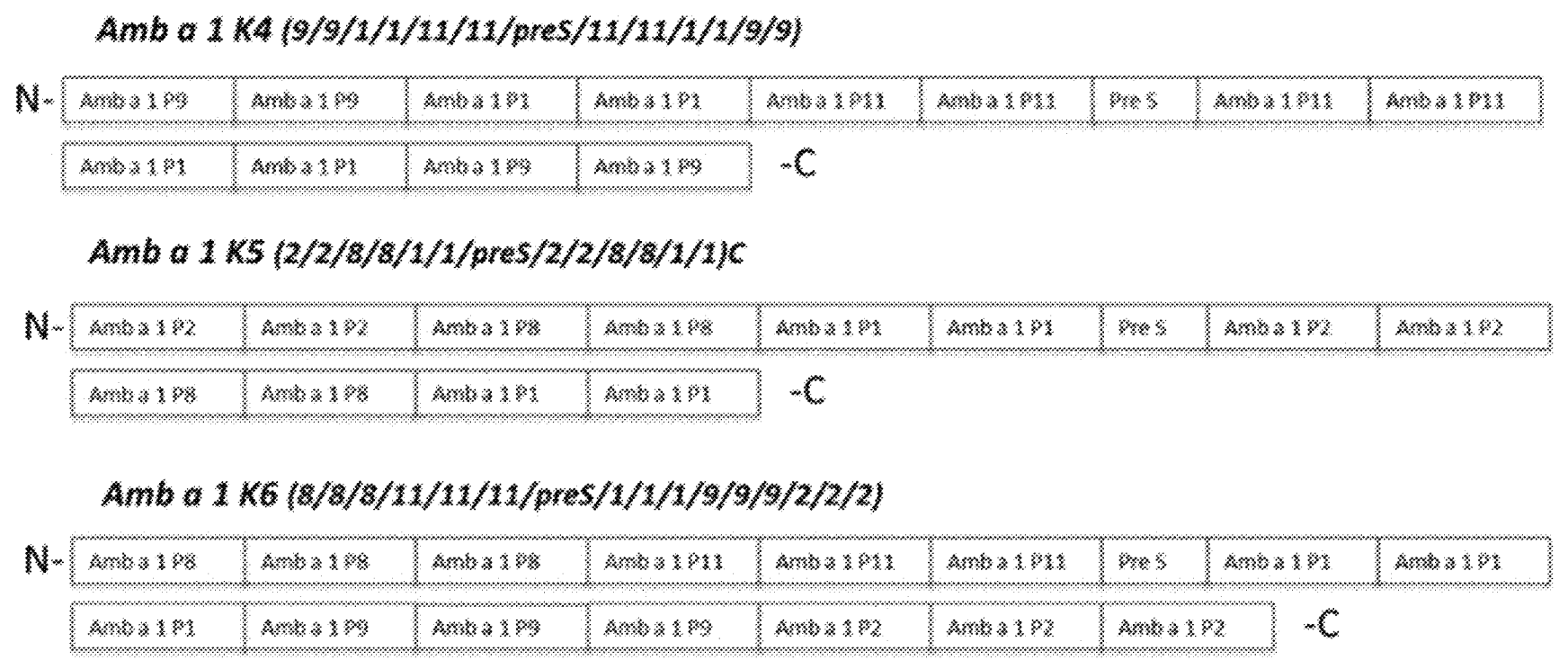

The IgE binding capacity of the Amb a 1 specific fusion proteins (see example 2; FIGS. 4A and 4B) was compared to those of the natural Amb a 1 by use of the IgE ELISA described under Method I(a). Again, a high OD value means that more IgE could be bound by the coated fusion protein or wild-type Amb a 1, indicating a high IgE reactivity. In total, sera of 19 ragweed allergic patients were used and one non allergic patient for negative control were tested.

The IgE reactivity of the natural Amb a 1 was used as a reference. It was defined as the maximal IgE reactivity and therefore set to 100% IgE reactivity for each individual patient and the IgE reactivity of the fusion proteins was calculated in correlation to that of Amb a 1 for each patient. The ELISA results shown in FIGS. 5 and 8 indicated that none of the fusion proteins exhibited a relevant IgE reactivity in comparison to wild-type Amb a 1.

Figure 10:
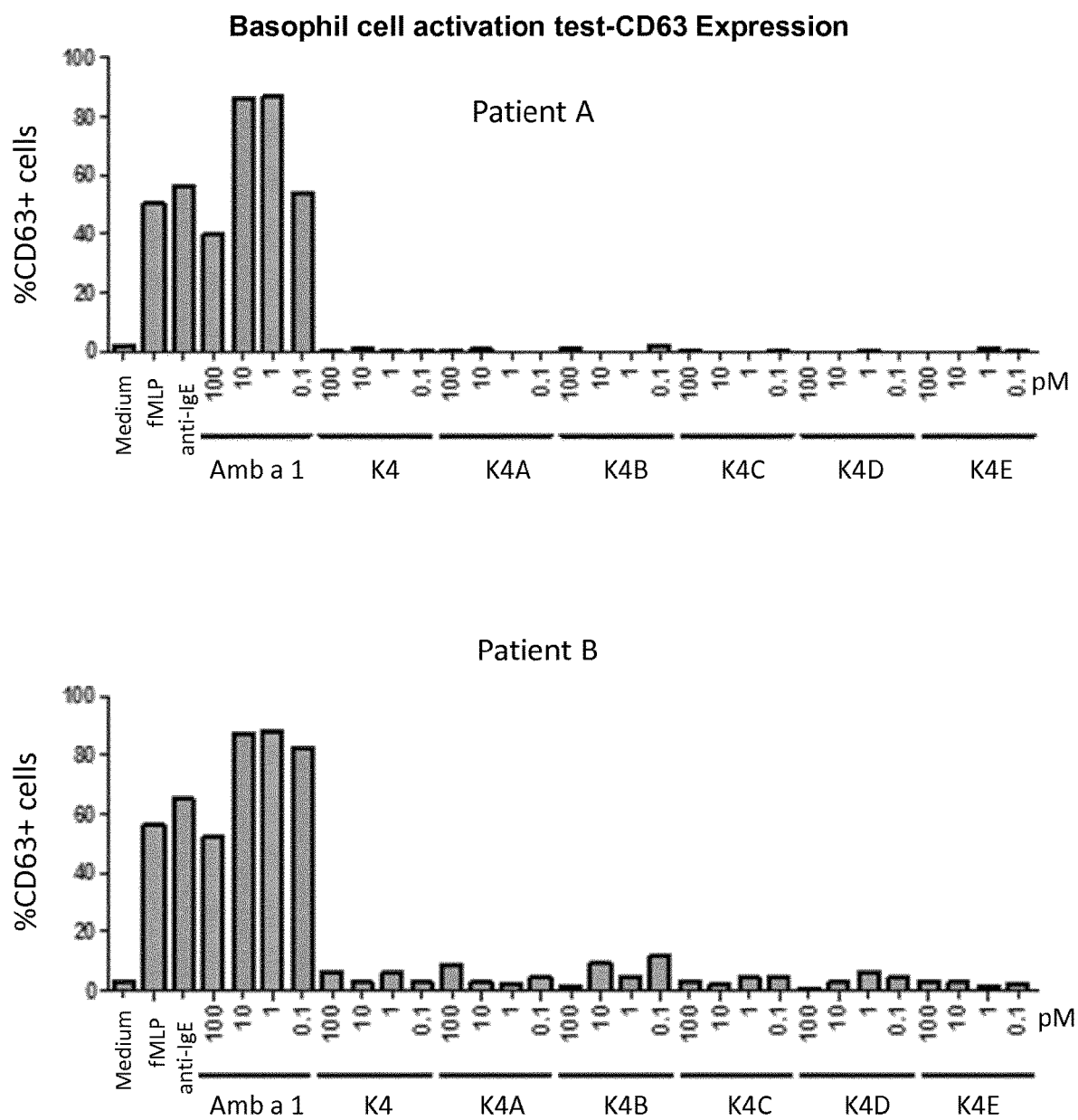
FIG. 10 shows the results of basophil activation assays (BAT assay) testing the allergenic potential of polypeptide constructs K2, K3, K4, K5, and K6, as well as constructs K4A, K4B, K4C, K4D, and K4E in comparison to wild-type Amb a 1.

IgE reactivity and potential to elicit allergic reactions in ragweed allergic individuals was further measured with a basophil activation test (BAT assay). Fresh blood from ragweed allergic patients was used. The IgE-reactivity of the fusion proteins was very low compared to the positive controls and wild-type Amb a 1, see FIG. 10. A detailed description of the experimental protocol for the BAT Assay is provided under Method II.

Example 9: Immunization of Rabbits with Fusion Proteins K1 to K6 Induce Blocking Antibodies which Inhibit Binding of Allergic Patient's IgE to Wild-Type Amb a 1

Figure 6:
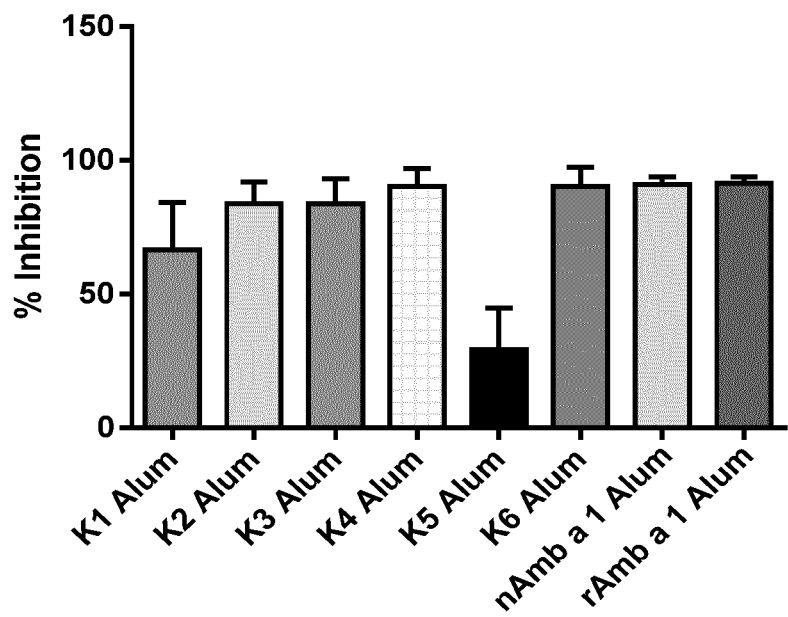
FIG. 6 shows the results of an inhibition ELISA. Antibodies comprised within sera of rabbits immunized with polypeptide constructs of FIGS. 4A and 4B adjuvanted with aluminum hydroxide (Alum) are able to inhibit binding of allergen specific IgE from ragweed allergic individuals to Amb a 1, if used as inhibitor in an inhibition ELISA with molecules. The inhibition of IgE binding obtained with sera from rabbits immunized with wild-type Amb a 1 (rAmb a 1, nAmb a 1) was included in the experiment as a control.

To evaluate the IgE inhibition potential of antibodies induced by immunization with Amb a 1 fusion proteins K1 to K6, ELISA plates coated with wild-type Amb a 1 were incubated with sera obtained from rabbits immunized with fusion proteins K1 to K6 followed by 26 sera from different ragweed allergic patients. The detailed protocol of the inhibition ELISA is described under Methods I(c). The results are shown in FIG. 6. Sera obtained by immunization with the Amb a 1 specific fusion protein K2, K3, K4, and K6 reached 80-90% levels of inhibition which was in the same range (90-92%) as determined for wild-type Amb a 1 used as reference and positive controls (nAmb a 1 and rAmb a 1). In contrast, IgG antibodies induced by Amb a 1 fusion proteins K1 and K5 showed lower levels of inhibition (60% and 23%).

In addition, the rabbit sera were diluted 1:10, 1:25, 1:50 and 1:100 with PBS and the IgE inhibition was tested again as described above. It turned out that the serum obtained from rabbits immunized with fusion protein K4 showed the highest inhibition rate (see FIG. 7). Serum from rabbits immunized with fusion protein K5 had shown a low IgE inhibition reactivity in the previous experiments so it was not further tested in different dilutions.

Example 10: Immunization of Rabbits with Fusion Proteins Induce Blocking Antibodies which Inhibit Binding of Allergic Patient's IgE to Clinically Relevant Isoforms of Amb a 1

Figure 9A:
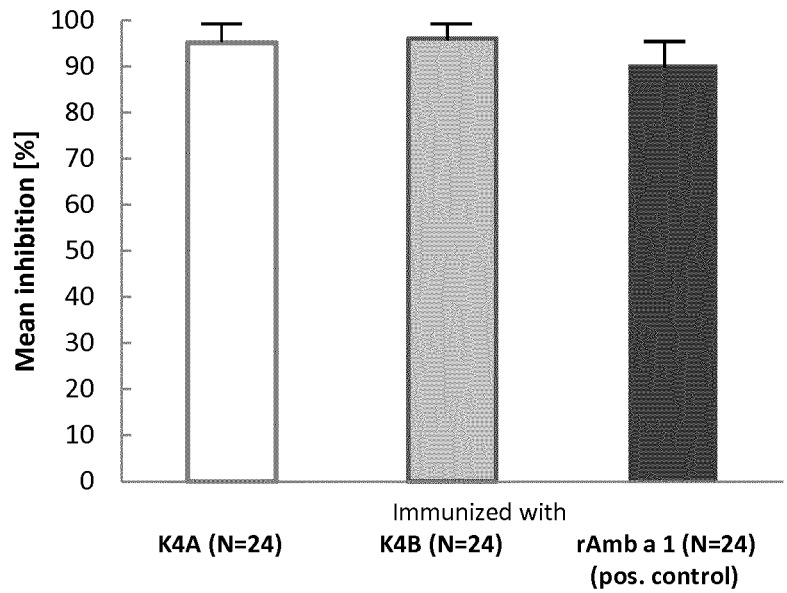
FIG. 9 shows the capability of sera obtained from rabbits immunized with the polypeptide contructs K4A, and K4B to inhibit the binding of ragweed allergic patient's IgE to isoforms Amb a 1.0305 (FIG. 9A) as well as Amb a 1.0101 and 1.0401 (FIG. 9B).
Figure 9B:
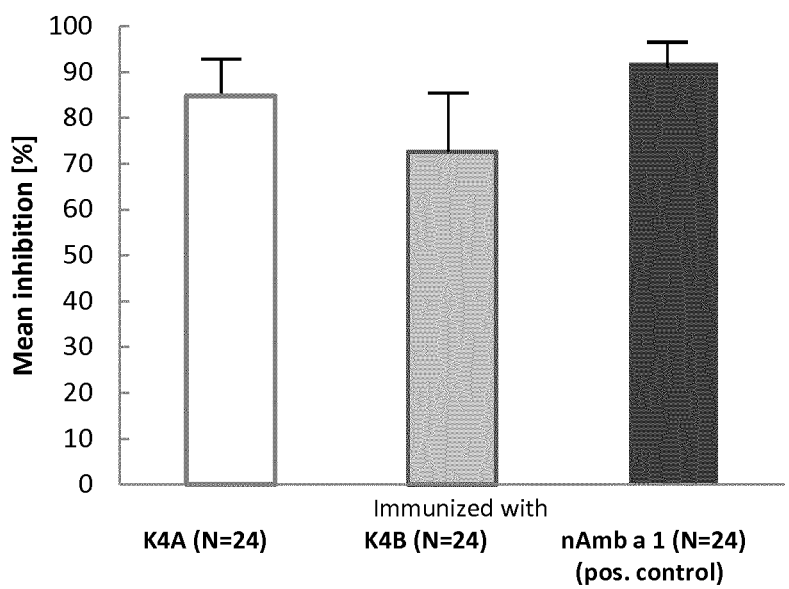

To evaluate the IgE inhibition potential of antibodies induced by immunization with Amb a 1 fusion proteins against different isoforms of Amb a 1, the inhibition ELISA of Example 9 was carried out with ELISA plates coated with rAmb a 1 (single isoform Amb a 1.0305) and nAmb a 1 (predominantly isoforms Amb a 1.0101 and Amb a 1.0401 as confirmed by mass spectroscopy), respectively. The coated ELISA plates were incubated with sera obtained from rabbits immunized with fusion proteins K4A and K4B followed by 26 sera from different ragweed allergic patients. The results are shown in FIGS. 9A and 9B. Antibodies induced by K4A and K4B were able to inhibit IgE binding to Amb a 1 isoforms 1.0305, as well as a mixture of isoforms 1.0101 and 1.0401.

---

The invention claimed is:

1. A polypeptide construct comprising at least a first and a second fragment of a mature allergen derived from an allergen of the Amb a 1 family of *Ambrosia artemisiifolia*, wherein the first and second fragments are not located adjacent to each other in the mature allergen, wherein each of the first and second fragments consists of up to 50 amino acid residues, wherein a. the first fragment is derived from the N-terminus of the mature allergen, wherein:

the first fragment comprises a sequence selected from the group consisting of AEDLQEILPVNETRRLTTSGAYNIIDG$X_1$(SEQ ID No. 2); AEDLQQILPSANETRSLTT$X_2$GTYNIIDG$X_1$ (SEQ ID No. 3); AEGVGEILPSVNETRSLQA$X_2$EAYNIIDK$X_1$ (SEQ ID No. 4); and AEDVEEFLPSANETRRSLKA$X_2$EAHNIIDK$X_1$ (SEQ ID No. 5);

wherein $X_1$ is cysteine, serine or no amino acid residue and $X_2$ is cysteine or serine, and b. the second fragment is derived from the C-terminus of the mature allergen, wherein:

the second fragment comprises a sequence selected from the group consisting of $X_3$R$X_4$GF$X_5$QVVNNNY$X_6X_7$WG$X_8$YA$X_9$GGS$X_{10}X_{11}$PTIL (SEQ ID No. 6);

$X_{12}$DPVLTP$X_{13}$Q$X_{14}$AGMIPAEPGE$X_{15}X_{16}X_{17}X_{18}$LTSSAGVLS $X_{19}$ (SEQ ID No. 7);

$X_{20}$RHGFFQVVNNNYDKWGSYAIGGSASPTIL (SEQ ID No. 8); $X_{21}$RFGFFQVVNNNYDRWGTYAIGGSSAPTIL (SEQ ID No. 9); VDPVLTPEQSAGMIPAEPGESALSLTSSAGVLS$X_{22}$ (SEQ ID No. 10); and SDPVLTPVQSAGMIPAEPGEAAIKLTSSAGVLS$X_{23}$ (SEQ ID No. 11), wherein $X_3$ is cysteine, serine, leucine or no amino acid residue, $X_4$ is histidine or phenylalanine, $X_5$ is phenylalanine or valine, $X_6$ is aspartic acid or glutamic acid, $X_7$ is arginine or lysine, $X_8$ is threonine or serine, $X_9$ is isoleucine or leucine, $X_{10}$ is serine or alanine and $X_{11}$ is glycine, serine or alanine, $X_{12}$ is serine or valine, $X_{13}$ is valine or glutamic acid, $X_{14}$ is serine, lysine or asparagine, $X_{15}$ is alanine or serine, $X_{16}$ is valine or alanine, $X_{17}$ is leucine or isoleucine, $X_{18}$ is serine, lysine or arginine and $X_{19}$ is cysteine, serine or no amino acid residue, $X_{20}$ and $X_{21}$ are independently cysteine, leucine, serine or no amino acid residue, $X_{22}$ and $X_{23}$ are independently cysteine, serine or no amino acid residue, wherein the first and second fragments are fused or conjugated to a carrier protein, wherein at least one of the first or second fragments is fused to the N-terminus of the carrier protein and at least one of the first or second fragments is fused to the C-terminus of the carrier protein.

2. The polypeptide construct according to claim 1, wherein the allergen of the Amb a 1 family is selected from the group consisting of Amb a 1.0101, Amb a 1.0201, Amb a 1.0202, Amb a 1.0301, Amb a 1.0302, Amb a 1.0303, Amb a 1.0304, Amb a 1.0305, Amb a 1.0401, Amb a 1.0402, Amb a 1.0501 and Amb a 1.0502.

3. The polypeptide construct according to claim 2, wherein the allergen of the Amb a 1 family is Amb a 1.0101, Amb a 1.0201, Amb a 1.0305 or Amb a 1.0401.

4. The polypeptide construct according to claim 1, wherein the first fragment comprises amino acid residues 1 to 20-40 of the mature allergen according to SEQ ID No. 1.

5. The polypeptide construct according to claim 1, wherein the first and second fragments consist of 25 to 45 amino acid residues.

6. The polypeptide construct according to claim 1, wherein the polypeptide construct comprises the second fragment comprising $X_3$R$X_4$GF$X_5$QVVNNNY$X_6X_7$WG$X_8$YA$X_9$GGS$X_{10}X_{11}$PTIL (SEQ ID No. 6).

7. The polypeptide construct according to claim 1, wherein the polypeptide construct comprises the second fragment comprising $X_{12}$DPVLTP$X_{13}$Q$X_{14}$AGMIPAEPGE$X_{15}X_{16}X_{18}$LTSSAGVLS$X_{19}$ (SEQ ID No. 7).

8. The polypeptide construct according to claim 1, wherein the second fragment comprises $X_{20}$RHGFFQVVNNNYDKWGSYAIGGSASPTIL (SEQ ID No. 8), $X_{21}$RFGFFQVVNNNYDRWGTYAIGGSSAPTIL (SEQ ID No. 9), VDPVLTPEQSAGMIPAEPGESALSLTSSAGVLS$X_{22}$ (SEQ ID No. 10) or SDPVLTPVQSAGMIPAEPGEAAIKLTSSAGVLS$X_{23}$ (SEQ ID No. 11).

9. The polypeptide construct according to claim 1, wherein the carrier protein is a viral protein or a fragment thereof consisting of 50 to 300 amino acid residues.

10. The polypeptide construct according to claim 9, wherein the viral protein is a capsid protein.

11. The polypeptide construct according to claim 9, wherein the viral protein is derived from a virus of the hepadnaviridae family.

12. The polypeptide construct according to claim 11, wherein the virus of the hepadnaviridae family is a Hepatitis B virus.

13. The polypeptide construct according to claim 12, wherein the viral protein of the Hepatitis B virus is PreS, PreS1 or PreS2.

14. The polypeptide construct according to claim 1, wherein the first and second fragments are fused to the N-terminus and/or C-terminus of the carrier protein.

15. The polypeptide construct according to claim 1 for the use in the treatment of a ragweed pollen allergy.

16. A nucleic acid molecule encoding a polypeptide construct as defined in claim 1, wherein the first and second fragments are fused to a carrier protein.

17. A vector comprising a nucleic acid molecule according to claim 16.

18. The vector according to claim 17, wherein said vector is an expression vector.

19. The vector according to claim 17, wherein said vector is a bacterial, fungal, insect, viral or mammalian vector.

20. A host cell comprising a nucleic acid molecule according to claim 16.

21. An immunogenic formulation for treatment of a ragweed pollen allergy comprising at least one polypeptide construct according to claim 1.

22. The immunogenic formulation according to claim 21, wherein said formulation comprises 10 ng to 1 g of said polypeptide.

23. The immunogenic formulation according to claim 21, wherein said formulation further comprises at least one adjuvant, pharmaceutical acceptable excipient and/or preservative.

* * * * *